US012558132B2

(12) United States Patent

Bowling et al.

(10) Patent No.: US 12,558,132 B2

(45) Date of Patent: Feb. 24, 2026

(54) ROBOTIC SPINE SURGERY SYSTEM AND METHODS WITH HAPTIC INTERFACE

(71) Applicant: MAKO Surgical Corp., Weston, FL (US)

(72) Inventors: David Gene Bowling, Los Ranchos De Albuquerque, NM (US); Bojan Gospavic, Boca Raton, FL (US); Christopher W. Jones, Kokomo, IN (US); Greg McEwan, Mattawan, MI (US); Lucas Gsellman, Kalamazoo, MI (US); Kana Nishimura, Baden-Baden (DE); Weiyi Ding, Northville, MI (US)

(73) Assignee: MAKO Surgical Corp., Weston, FL (US)

( * ) Notice: Subject to any disclaimer, the term of this patent is extended or adjusted under 35 U.S.C. 154(b) by 832 days.

(21) Appl. No.: 17/214,392

(22) Filed: Mar. 26, 2021

(65) Prior Publication Data

US 2021/0298795 A1 Sep. 30, 2021

Related U.S. Application Data

(60) Provisional application No. 63/001,019, filed on Mar. 27, 2020.

(51) Int. Cl.
*A61B 17/70* (2006.01)
*A61B 34/00* (2016.01)
(Continued)

(52) U.S. Cl.
CPC .......... *A61B 17/7082* (2013.01); *A61B 34/10* (2016.02); *A61B 34/25* (2016.02);
(Continued)

(58) Field of Classification Search
CPC ......... A61B 34/10; A61B 34/25; A61B 34/30; A61B 34/76
See application file for complete search history.

(56) References Cited

U.S. PATENT DOCUMENTS 4,124,026 A 11/1978 Berner et al.
4,359,906 A 11/1982 Cordey
(Continued)

FOREIGN PATENT DOCUMENTS

CN 201422918 Y 3/2010
CN 201542641 U 8/2010
(Continued)

OTHER PUBLICATIONS

English language abstract and machine-assisted English translation for CN 101579269 extracted from espacenet.com database on Oct. 1, 2018, 11 pages.
(Continued)

*Primary Examiner* — Sameh R Boles
(74) *Attorney, Agent, or Firm* — Howard & Howard Attorneys PLLC

(57) ABSTRACT

Disclosed herein are techniques including a robotic manipulator including a surgical tool to interface with and rotate the screw about a rotational axis. A haptic device includes an actuator and a rotational interface coupled to the actuator and the rotational interface is manually manipulatable by a hand of an operator. One or more controllers control movement of the robotic manipulator to maintain the rotational axis of the surgical tool along a planned trajectory; autonomously control the surgical tool to rotate the screw at a rotational rate about the rotational axis and to linearly advance the screw at an advancement rate according to a known thread geometry of the screw; obtain a measurement indicative of a present interaction between the screw and the target site; and control the actuator of the haptic device to
(Continued)

enable the rotational interface to emulate the present interaction between the screw and the target site.

19 Claims, 21 Drawing Sheets

(51) Int. Cl.
    *A61B 34/10*           (2016.01)
    *A61B 34/30*           (2016.01)

(52) U.S. Cl.
    CPC .............. *A61B 34/30* (2016.02); *A61B 34/76* (2016.02); *A61B 2034/104* (2016.02); *A61B 2034/107* (2016.02)

(56) References Cited

U.S. PATENT DOCUMENTS

| | | | |
|---|---|---|---|
| 4,922,436 A | 5/1990 | Dohm et al. |
| 5,014,794 A | 5/1991 | Hansson |
| 5,320,115 A | 6/1994 | Kenna |
| 5,507,211 A | 4/1996 | Wagner |
| 5,799,055 A | 8/1998 | Peshkin et al. |
| 5,999,168 A | 12/1999 | Rosenberg et al. |
| 6,154,201 A | 11/2000 | Levin et al. |
| 6,228,089 B1 | 5/2001 | Wahrburg |
| 6,236,875 B1 | 5/2001 | Bucholz et al. |
| 6,246,200 B1 | 6/2001 | Blumenkranz et al. |
| 6,271,828 B1 | 8/2001 | Rosenberg et al. |
| 6,535,756 B1 | 3/2003 | Simon et al. |
| 6,680,595 B2 | 1/2004 | Ito |
| 6,711,432 B1 | 3/2004 | Krause et al. |
| 6,772,002 B2 | 8/2004 | Schmidt et al. |
| 6,785,572 B2 | 8/2004 | Yanof et al. |
| 6,823,207 B1 | 11/2004 | Jensen et al. |
| 6,837,892 B2 | 1/2005 | Shoham |
| 6,866,671 B2 | 3/2005 | Tierney et al. |
| 6,877,239 B2 | 4/2005 | Leitner et al. |
| 6,920,347 B2 | 7/2005 | Simon et al. |
| 6,947,786 B2 | 9/2005 | Simon et al. |
| 6,993,374 B2 | 1/2006 | Sasso |
| 7,001,393 B2 | 2/2006 | Schwenke et al. |
| 7,048,745 B2 | 5/2006 | Tierney et al. |
| 7,104,998 B2 | 9/2006 | Yoon et al. |
| 7,107,883 B2 | 9/2006 | Casutt |
| 7,188,626 B2 | 3/2007 | Foley et al. |
| 7,194,120 B2 | 3/2007 | Wicker et al. |
| 7,235,076 B2 | 6/2007 | Pacheco |
| 7,327,348 B2 | 2/2008 | Goldenberg et al. |
| 7,331,965 B2 | 2/2008 | Nielsen |
| 7,338,526 B2 | 3/2008 | Steinberg |
| 7,396,357 B2 | 7/2008 | Tornier et al. |
| 7,497,868 B2 | 3/2009 | Steinberg |
| 7,542,791 B2 | 6/2009 | Mire et al. |
| 7,570,791 B2 | 8/2009 | Frank et al. |
| 7,587,235 B2 | 9/2009 | Wist et al. |
| 7,607,238 B2 | 10/2009 | Kim et al. |
| 7,630,753 B2 | 12/2009 | Simon et al. |
| 7,637,929 B2 | 12/2009 | Auth |
| 7,670,343 B2 | 3/2010 | Meridew et al. |
| 7,699,877 B2 | 4/2010 | Davison |
| 7,722,530 B2 | 5/2010 | Davison |
| 7,725,162 B2 | 5/2010 | Malackowski et al. |
| 7,736,630 B2 | 6/2010 | Touitou et al. |
| 7,766,930 B2 | 8/2010 | DiPoto et al. |
| 7,799,036 B2 | 9/2010 | Davison et al. |
| 7,822,244 B2 | 10/2010 | Blumhofer |
| 7,831,292 B2 | 11/2010 | Quaid et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,843,158 B2 | 11/2010 | Prisco |
| 7,853,305 B2 | 12/2010 | Simon et al. |
| 7,887,567 B2 | 2/2011 | Shoham et al. |
| 7,900,524 B2 | 3/2011 | Calloway et al. |
| 8,010,177 B2 | 8/2011 | Csavoy et al. |
| 8,010,180 B2 | 8/2011 | Quaid et al. |
| 8,010,181 B2 | 8/2011 | Smith et al. |
| 8,016,835 B2 | 9/2011 | Birkmeyer et al. |
| 8,036,441 B2 | 10/2011 | Frank et al. |
| 8,046,054 B2 | 10/2011 | Kim et al. |
| 8,052,688 B2 | 11/2011 | Wolf, II |
| 8,057,407 B2 | 11/2011 | Martinelli et al. |
| 8,100,950 B2 | 1/2012 | St. Clair et al. |
| 8,133,234 B2 | 3/2012 | Meridew et al. |
| 8,167,823 B2 | 5/2012 | Nycz et al. |
| 8,182,469 B2 | 5/2012 | Anderson et al. |
| 8,182,470 B2 | 5/2012 | Devengenzo et al. |
| 8,182,491 B2 | 5/2012 | Selover et al. |
| 8,202,244 B2 | 6/2012 | Cohen et al. |
| 8,206,405 B2 | 6/2012 | Beverland et al. |
| 8,219,177 B2 | 7/2012 | Smith et al. |
| 8,219,178 B2 | 7/2012 | Smith et al. |
| 8,241,296 B2 | 8/2012 | Wasielewski |
| 8,271,066 B2 | 9/2012 | Sarin et al. |
| 8,277,491 B2 | 10/2012 | Selover et al. |
| 8,286,723 B2 | 10/2012 | Puzio et al. |
| 8,311,611 B2 | 11/2012 | Csavoy et al. |
| 8,328,852 B2 | 12/2012 | Zehavi et al. |
| 8,335,553 B2 | 12/2012 | Rubner et al. |
| 8,337,426 B2 | 12/2012 | Nycz |
| 8,394,144 B2 | 3/2013 | Zehavi et al. |
| 8,395,342 B2 | 3/2013 | Prisco |
| 8,419,717 B2 | 4/2013 | Diolaiti et al. |
| 8,425,522 B2 | 4/2013 | Bonutti |
| 8,442,677 B2 | 5/2013 | Shoham |
| 8,454,583 B2 | 6/2013 | Perez-Cruet et al. |
| 8,454,619 B1 | 6/2013 | Head |
| 8,469,963 B2 | 6/2013 | Shoham |
| 8,491,603 B2 | 7/2013 | Yeung et al. |
| 8,500,738 B2 | 8/2013 | Wolf, II |
| 8,509,503 B2 | 8/2013 | Nahum et al. |
| 8,518,051 B2 | 8/2013 | Shoham et al. |
| 8,571,638 B2 | 10/2013 | Shoham |
| 8,572,860 B2 | 11/2013 | Fritzinger |
| 8,615,288 B2 | 12/2013 | Govari et al. |
| 8,620,473 B2 | 12/2013 | Diolaiti et al. |
| 8,634,897 B2 | 1/2014 | Simon et al. |
| 8,657,829 B2 | 2/2014 | McCardel |
| 8,705,829 B2 | 4/2014 | Frank et al. |
| 8,706,185 B2 | 4/2014 | Foley et al. |
| 8,709,016 B2 | 4/2014 | Park et al. |
| 8,740,885 B2 | 6/2014 | Larkin et al. |
| 8,747,476 B2 | 6/2014 | Steinberg |
| 8,758,413 B2 | 6/2014 | Heiges et al. |
| 8,814,877 B2 | 8/2014 | Wasielewski |
| 8,814,914 B2 | 8/2014 | Miller et al. |
| 8,838,205 B2 | 9/2014 | Shoham et al. |
| 8,840,629 B2 | 9/2014 | Bonutti |
| 8,864,752 B2 | 10/2014 | Diolaiti et al. |
| 8,876,837 B2 | 11/2014 | Smith et al. |
| 8,900,244 B2 | 12/2014 | Meridew et al. |
| 8,911,429 B2 | 12/2014 | Olds et al. |
| 8,951,256 B2 | 2/2015 | Burroughs |
| 8,961,526 B2 | 2/2015 | Burroughs |
| 8,974,460 B2 | 3/2015 | De la Fuente Klein et al. |
| 8,979,859 B2 | 3/2015 | Leparmentier et al. |
| 8,992,580 B2 | 3/2015 | Bar et al. |
| 8,998,909 B2 | 4/2015 | Gillman et al. |
| 9,008,757 B2 | 4/2015 | Wu |
| 9,011,456 B2 | 4/2015 | Ranawat et al. |
| 9,017,313 B2 | 4/2015 | Steinberg |
| 9,042,960 B2 | 5/2015 | Neubardt |
| 9,044,190 B2 | 6/2015 | Rubner et al. |
| 9,050,108 B2 | 6/2015 | Grinberg et al. |
| 9,056,015 B2 | 6/2015 | Zehavi et al. |
| 9,066,751 B2 | 6/2015 | Sasso |
| 9,078,685 B2 | 7/2015 | Smith et al. |
| 9,101,443 B2 | 8/2015 | Bonutti |
| 9,107,721 B2 | 8/2015 | Plotkin |
| 9,125,556 B2 | 9/2015 | Zehavi et al. |
| 9,125,680 B2 | 9/2015 | Kostrzewski et al. |
| 9,131,986 B2 | 9/2015 | Greer et al. |
| 9,138,319 B2 | 9/2015 | Fanson et al. |

(56) References Cited

U.S. PATENT DOCUMENTS

| | | |
|---|---|---|
| 9,149,281 B2 | 10/2015 | Bonutti |
| 9,155,544 B2 | 10/2015 | Bonutti |
| 9,161,799 B2 | 10/2015 | Benson et al. |
| 9,168,154 B2 | 10/2015 | Behzadi |
| 9,192,395 B2 | 11/2015 | Bonutti |
| 9,198,714 B2 | 12/2015 | Worrell et al. |
| 9,198,731 B2 | 12/2015 | Balaji et al. |
| 9,211,128 B2 | 12/2015 | Gillman et al. |
| 9,211,160 B2 | 12/2015 | Pivotto et al. |
| 9,220,612 B2 | 12/2015 | Behzadi |
| 9,232,906 B2 | 1/2016 | Wolf, II |
| 9,237,861 B2 | 1/2016 | Nahum et al. |
| 9,240,046 B2 | 1/2016 | Carrell et al. |
| 9,241,771 B2 | 1/2016 | Kostrzewski et al. |
| 9,243,881 B2 | 1/2016 | Bourque et al. |
| 9,265,551 B2 | 2/2016 | Kust et al. |
| 9,271,741 B2 | 3/2016 | Bonutti |
| 9,271,779 B2 | 3/2016 | Bonutti |
| 9,283,048 B2 | 3/2016 | Kostrzewski et al. |
| 9,295,500 B2 | 3/2016 | Marigowda |
| 9,308,050 B2 | 4/2016 | Kostrzewski et al. |
| 9,333,042 B2 | 5/2016 | Diolaiti et al. |
| 9,339,278 B2 | 5/2016 | Meridew et al. |
| 9,339,345 B2 | 5/2016 | Song et al. |
| 9,345,387 B2 | 5/2016 | Larkin |
| 9,358,130 B2 | 6/2016 | Livorsi et al. |
| 9,398,962 B2 | 7/2016 | Steinberg |
| 9,439,675 B2 | 9/2016 | Penenberg |
| 9,452,019 B2 | 9/2016 | Schena et al. |
| 9,456,827 B2 | 10/2016 | Grinberg et al. |
| 9,462,943 B2 | 10/2016 | Brownell |
| 9,468,538 B2 | 10/2016 | Nycz et al. |
| 9,480,516 B2 | 11/2016 | Crawford et al. |
| 9,486,227 B2 | 11/2016 | Bonutti |
| 9,491,415 B2 | 11/2016 | Deitz et al. |
| 9,492,241 B2 | 11/2016 | Joskowicz et al. |
| 9,519,341 B2 | 12/2016 | Hasegawa et al. |
| 9,532,730 B2 | 1/2017 | Wasielewski |
| 9,532,849 B2 | 1/2017 | Anderson et al. |
| 9,536,309 B2 | 1/2017 | Sela et al. |
| 9,539,112 B2 | 1/2017 | Thornberry |
| 9,545,233 B2 | 1/2017 | Sirpad et al. |
| 9,545,280 B2 | 1/2017 | Crawford et al. |
| 9,549,781 B2 | 1/2017 | He et al. |
| 9,554,864 B2 | 1/2017 | Taylor et al. |
| 9,554,865 B2 | 1/2017 | Olds et al. |
| 9,561,082 B2 | 2/2017 | Yen et al. |
| 9,566,122 B2 | 2/2017 | Bowling et al. |
| 9,576,353 B2 | 2/2017 | Mahn et al. |
| 9,585,677 B2 | 3/2017 | Garcia et al. |
| 9,585,725 B2 | 3/2017 | Bonutti |
| 9,585,768 B2 | 3/2017 | Sherman et al. |
| 9,592,096 B2 | 3/2017 | Maillet et al. |
| 9,600,138 B2 | 3/2017 | Thomas et al. |
| 9,622,757 B2 | 4/2017 | Bourque et al. |
| 9,622,779 B2 | 4/2017 | Horton et al. |
| 9,629,687 B2 | 4/2017 | Bonutti |
| 9,636,162 B2 | 5/2017 | Crawford et al. |
| 9,649,096 B2 | 5/2017 | Sholev |
| 9,649,160 B2 | 5/2017 | van der Walt et al. |
| 9,649,202 B2 | 5/2017 | Behzadi et al. |
| 9,655,649 B2 | 5/2017 | Shoham |
| 9,662,160 B2 | 5/2017 | Beale et al. |
| 9,662,174 B2 | 5/2017 | Taylor et al. |
| 9,668,768 B2 | 6/2017 | Piron et al. |
| 9,668,875 B2 | 6/2017 | Steinberg |
| 9,675,272 B2 | 6/2017 | Selover et al. |
| 9,687,306 B2 | 6/2017 | Markey et al. |
| 9,693,878 B2 | 7/2017 | Kunz et al. |
| 9,713,499 B2 | 7/2017 | Bar et al. |
| 9,724,167 B2 | 8/2017 | Ziaei et al. |
| 9,734,632 B2 | 8/2017 | Thomas et al. |
| 9,737,326 B2 | 8/2017 | Worrell et al. |
| 9,743,971 B2 | 8/2017 | Belkoff et al. |
| 9,743,995 B2 | 8/2017 | Lohmeier et al. |
| 9,750,510 B2 | 9/2017 | Kostrzewski et al. |
| 9,750,545 B2 | 9/2017 | Cryder et al. |
| 9,750,577 B2 * | 9/2017 | Pacheco .................. A61B 8/12 |
| 9,757,087 B2 | 9/2017 | Simon et al. |
| 9,782,229 B2 | 10/2017 | Crawford et al. |
| 9,788,966 B2 | 10/2017 | Steinberg |
| 9,795,319 B2 | 10/2017 | Lavallee et al. |
| 9,795,394 B2 | 10/2017 | Bonutti |
| 9,808,318 B2 | 11/2017 | Bonutti |
| 9,811,066 B1 | 11/2017 | Linnell |
| 9,814,535 B2 | 11/2017 | Bar et al. |
| 9,815,206 B2 | 11/2017 | Balicki et al. |
| 9,833,292 B2 | 12/2017 | Kostrzewski et al. |
| 9,833,907 B1 | 12/2017 | Linnell et al. |
| 9,862,099 B1 | 1/2018 | Linnell et al. |
| 9,877,793 B2 | 1/2018 | Bonutti |
| 9,931,059 B2 | 4/2018 | Borja |
| 9,987,092 B2 | 6/2018 | Hladio et al. |
| 9,987,753 B1 | 6/2018 | Linnell et al. |
| 10,004,562 B2 | 6/2018 | Kostrzewski et al. |
| RE46,954 E | 7/2018 | Pedicini |
| 10,028,800 B2 | 7/2018 | Bourque et al. |
| 10,034,753 B2 | 7/2018 | Dressler et al. |
| 10,039,605 B2 | 8/2018 | Kostrzewski et al. |
| 10,076,385 B2 | 9/2018 | Shoham et al. |
| 10,080,509 B2 | 9/2018 | Wasielewski |
| 10,080,615 B2 | 9/2018 | Bartelme et al. |
| 10,085,786 B2 | 10/2018 | Chandanson et al. |
| 10,172,679 B2 | 1/2019 | Mewes et al. |
| 10,191,560 B2 | 1/2019 | Linnell |
| 10,201,391 B2 | 2/2019 | Bonutti |
| 10,201,903 B1 | 2/2019 | Linnell et al. |
| 10,206,731 B2 | 2/2019 | Kust et al. |
| 10,251,719 B2 | 4/2019 | Mahdi |
| 10,265,128 B2 | 4/2019 | Bonutti |
| 10,335,183 B2 | 7/2019 | Worrell et al. |
| 10,383,674 B2 | 8/2019 | Sexson et al. |
| 10,413,371 B2 | 9/2019 | Sweeney, II et al. |
| 2003/0173096 A1 | 9/2003 | Setton et al. |
| 2003/0181800 A1 | 9/2003 | Bonutti |
| 2005/0149050 A1 | 7/2005 | Stifter et al. |
| 2005/0171557 A1 | 8/2005 | Shoham |
| 2006/0036264 A1 | 2/2006 | Selover et al. |
| 2007/0058406 A1 | 3/2007 | Inoshita et al. |
| 2007/0093689 A1 | 4/2007 | Steinberg |
| 2007/0156157 A1 | 7/2007 | Nahum et al. |
| 2007/0250078 A1 | 10/2007 | Stuart |
| 2008/0004634 A1 | 1/2008 | Farritor et al. |
| 2008/0058837 A1 | 3/2008 | Steinberg |
| 2008/0071374 A1 | 3/2008 | Steinberg |
| 2008/0108994 A1 | 5/2008 | Steinberg |
| 2008/0114376 A1 | 5/2008 | Steinberg |
| 2008/0147188 A1 | 6/2008 | Steinberg |
| 2008/0249536 A1 | 10/2008 | Stahler et al. |
| 2008/0281332 A1 | 11/2008 | Taylor |
| 2009/0182348 A1 | 7/2009 | Nahapetian et al. |
| 2010/0137871 A1 | 6/2010 | Borja |
| 2010/0204714 A1 | 8/2010 | Shoham |
| 2010/0241129 A1 | 9/2010 | Markey et al. |
| 2011/0015649 A1 | 1/2011 | Anvari et al. |
| 2011/0066160 A1 | 3/2011 | Simaan et al. |
| 2011/0092859 A1 | 4/2011 | Neubardt |
| 2011/0210229 A1 | 9/2011 | Bonnet et al. |
| 2011/0306873 A1 | 12/2011 | Shenai et al. |
| 2012/0046665 A1 | 2/2012 | Kim |
| 2012/0071863 A1 | 3/2012 | Lee et al. |
| 2012/0143211 A1 | 6/2012 | Kishi |
| 2012/0209117 A1 | 8/2012 | Mozes et al. |
| 2012/0283747 A1 | 11/2012 | Popovic |
| 2013/0307955 A1 | 11/2013 | Deitz et al. |
| 2013/0345718 A1 | 12/2013 | Crawford et al. |
| 2014/0031722 A1 | 1/2014 | Li et al. |
| 2014/0052150 A1 | 2/2014 | Taylor et al. |
| 2014/0058406 A1 | 2/2014 | Tsekos |
| 2014/0112344 A1 | 4/2014 | Mineshita |
| 2014/0135791 A1 | 5/2014 | Nikou et al. |
| 2014/0135796 A1 | 5/2014 | Simon et al. |
| 2014/0180290 A1 | 6/2014 | Otto et al. |
| 2014/0222012 A1 | 8/2014 | Belkoff et al. |

(56) References Cited

U.S. PATENT DOCUMENTS

| | | |
|---|---|---|
| 2014/0257296 A1 | 9/2014 | Morgenstern Lopez |
| 2014/0275955 A1 | 9/2014 | Crawford et al. |
| 2014/0309560 A1 | 10/2014 | Bonutti |
| 2014/0316436 A1 | 10/2014 | Bar et al. |
| 2014/0360305 A1 | 12/2014 | Olds et al. |
| 2014/0371577 A1 | 12/2014 | Maillet et al. |
| 2014/0378999 A1 | 12/2014 | Crawford et al. |
| 2015/0031985 A1 | 1/2015 | Reddy et al. |
| 2015/0032164 A1 | 1/2015 | Crawford et al. |
| 2015/0100066 A1 | 4/2015 | Kostrzewski et al. |
| 2015/0112344 A1 | 4/2015 | Shoham et al. |
| 2015/0142372 A1 | 5/2015 | Singh |
| 2015/0182285 A1 | 7/2015 | Yen et al. |
| 2015/0196326 A1 | 7/2015 | Bar et al. |
| 2015/0196365 A1 | 7/2015 | Kostrzewski et al. |
| 2015/0202009 A1 | 7/2015 | Nussbaumer et al. |
| 2015/0209056 A1 | 7/2015 | Shoham et al. |
| 2015/0209119 A1 | 7/2015 | Theodore et al. |
| 2015/0223897 A1 | 8/2015 | Kostrzewski et al. |
| 2015/0223906 A1 | 8/2015 | O'Neill et al. |
| 2015/0238206 A1 | 8/2015 | Benson et al. |
| 2015/0272696 A1 | 10/2015 | Fry et al. |
| 2015/0289992 A1 | 10/2015 | Anglin et al. |
| 2015/0305817 A1 | 10/2015 | Kostrzewski |
| 2015/0313684 A1 | 11/2015 | Fanson et al. |
| 2015/0327948 A1 | 11/2015 | Schoepp et al. |
| 2015/0335386 A1 | 11/2015 | Smith et al. |
| 2015/0351860 A1 | 12/2015 | Piron et al. |
| 2015/0366624 A1 | 12/2015 | Kostrzewski et al. |
| 2016/0000512 A1 | 1/2016 | Gombert et al. |
| 2016/0008011 A1 | 1/2016 | Kostrzewski |
| 2016/0030117 A1 | 2/2016 | Mewes |
| 2016/0038238 A1 | 2/2016 | Kostrzewski et al. |
| 2016/0038242 A1 | 2/2016 | Lo Iacono et al. |
| 2016/0081753 A1 | 3/2016 | Kostrzewski |
| 2016/0081754 A1 | 3/2016 | Kostrzewski et al. |
| 2016/0081819 A1 | 3/2016 | Kelman et al. |
| 2016/0095631 A1 | 4/2016 | Stad |
| 2016/0095720 A1 | 4/2016 | Behzadi |
| 2016/0120612 A1 | 5/2016 | Yorimoto |
| 2016/0128789 A1 | 5/2016 | Kostrzewski et al. |
| 2016/0151120 A1 | 6/2016 | Kostrzewski et al. |
| 2016/0157941 A1 | 6/2016 | Anvari et al. |
| 2016/0175110 A1 | 6/2016 | Behzadi et al. |
| 2016/0206347 A1 | 7/2016 | Bar et al. |
| 2016/0220315 A1 | 8/2016 | Falardeau et al. |
| 2016/0220320 A1 | 8/2016 | Crawford et al. |
| 2016/0220385 A1 | 8/2016 | Falardeau et al. |
| 2016/0228133 A1 | 8/2016 | Meridew et al. |
| 2016/0235490 A1 | 8/2016 | Srivastava et al. |
| 2016/0235492 A1 | 8/2016 | Morard et al. |
| 2016/0235493 A1 | 8/2016 | LeBoeuf, II et al. |
| 2016/0242860 A1 | 8/2016 | Diolaiti et al. |
| 2016/0242934 A1 | 8/2016 | van der Walt et al. |
| 2016/0256225 A1 | 9/2016 | Crawford et al. |
| 2016/0278875 A1 | 9/2016 | Crawford et al. |
| 2016/0278941 A1 | 9/2016 | Livorsi et al. |
| 2016/0296266 A1 | 10/2016 | Chandanson et al. |
| 2016/0310218 A1 | 10/2016 | Ruckel et al. |
| 2016/0310221 A1 | 10/2016 | Bar et al. |
| 2016/0331479 A1 | 11/2016 | Crawford |
| 2016/0331481 A1 | 11/2016 | Bonutti |
| 2016/0374769 A1 | 12/2016 | Schena et al. |
| 2017/0000572 A1 | 1/2017 | Moctezuma de la Barrera et al. |
| 2017/0007334 A1 | 1/2017 | Crawford et al. |
| 2017/0020630 A1 | 1/2017 | Johnson et al. |
| 2017/0027652 A1 | 2/2017 | Johnson et al. |
| 2017/0042620 A1 | 2/2017 | Bartelme et al. |
| 2017/0055940 A1 | 3/2017 | Shoham |
| 2017/0056086 A1 | 3/2017 | Kostrzewski et al. |
| 2017/0056116 A1 | 3/2017 | Kostrzewski |
| 2017/0065428 A1 | 3/2017 | Behzadi |
| 2017/0065432 A1 | 3/2017 | Singh |
| 2017/0071682 A1 | 3/2017 | Bar et al. |
| 2017/0071685 A1 | 3/2017 | Crawford et al. |
| 2017/0071691 A1 | 3/2017 | Crawford et al. |
| 2017/0071759 A1 | 3/2017 | Behzadi et al. |
| 2017/0079727 A1 | 3/2017 | Crawford et al. |
| 2017/0086896 A1 | 3/2017 | Crawford et al. |
| 2017/0086927 A1 | 3/2017 | Auld et al. |
| 2017/0086928 A1 | 3/2017 | Auld et al. |
| 2017/0086932 A1 | 3/2017 | Auld et al. |
| 2017/0105846 A1 | 4/2017 | Behzadi |
| 2017/0108930 A1 | 4/2017 | Banerjee et al. |
| 2017/0119339 A1 | 5/2017 | Johnson et al. |
| 2017/0119472 A1 | 5/2017 | Herrmann et al. |
| 2017/0132789 A1 | 5/2017 | Deitz et al. |
| 2017/0143426 A1 | 5/2017 | Isaacs et al. |
| 2017/0143429 A1 | 5/2017 | Richmond et al. |
| 2017/0151025 A1 | 6/2017 | Mewes et al. |
| 2017/0156805 A1 | 6/2017 | Taylor et al. |
| 2017/0156816 A1 | 6/2017 | Ibrahim |
| 2017/0172669 A1 | 6/2017 | Berkowitz et al. |
| 2017/0172762 A1 | 6/2017 | Sherman et al. |
| 2017/0178349 A1 | 6/2017 | Ketcha et al. |
| 2017/0181774 A1 | 6/2017 | Cahill |
| 2017/0186180 A1 | 6/2017 | Piron et al. |
| 2017/0196506 A1 | 7/2017 | Behzadi |
| 2017/0196597 A1 | 7/2017 | Corbin et al. |
| 2017/0196599 A1 | 7/2017 | Kwon et al. |
| 2017/0196641 A1 | 7/2017 | Jagga et al. |
| 2017/0196701 A1 | 7/2017 | Behzadi et al. |
| 2017/0196705 A1 | 7/2017 | Behzadi |
| 2017/0196706 A1 | 7/2017 | Behzadi |
| 2017/0196708 A1 | 7/2017 | Behzadi et al. |
| 2017/0196710 A1 | 7/2017 | Behzadi |
| 2017/0196711 A1 | 7/2017 | Behzadi |
| 2017/0202628 A1 | 7/2017 | Dell et al. |
| 2017/0202629 A1 | 7/2017 | Maillet et al. |
| 2017/0202683 A1 | 7/2017 | Behzadi |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0224358 A1 | 8/2017 | Kostrzewski |
| 2017/0231702 A1 | 8/2017 | Crawford et al. |
| 2017/0239002 A1 | 8/2017 | Crawford et al. |
| 2017/0239003 A1 | 8/2017 | Crawford et al. |
| 2017/0239006 A1 | 8/2017 | Crawford et al. |
| 2017/0239007 A1 | 8/2017 | Crawford et al. |
| 2017/0239451 A1 | 8/2017 | Berkowitz |
| 2017/0239452 A1 | 8/2017 | Berkowitz et al. |
| 2017/0245951 A1 | 8/2017 | Crawford et al. |
| 2017/0252112 A1 | 9/2017 | Crawford et al. |
| 2017/0252114 A1 | 9/2017 | Crawford et al. |
| 2017/0258469 A1 | 9/2017 | Shelton, IV et al. |
| 2017/0258533 A1 | 9/2017 | Crawford et al. |
| 2017/0258535 A1 | 9/2017 | Crawford et al. |
| 2017/0261348 A1 | 9/2017 | LeBoeuf, II et al. |
| 2017/0265774 A1 | 9/2017 | Johnson et al. |
| 2017/0265872 A1 | 9/2017 | Otto et al. |
| 2017/0281145 A1 | 10/2017 | Crawford et al. |
| 2017/0290666 A1 | 10/2017 | Behzadi |
| 2017/0296274 A1 | 10/2017 | van der Walt et al. |
| 2017/0296276 A1 | 10/2017 | Bonutti |
| 2017/0312039 A1 | 11/2017 | Crawford et al. |
| 2017/0316561 A1 | 11/2017 | Helm et al. |
| 2017/0325892 A1 | 11/2017 | Aghazadeh |
| 2017/0333057 A1 | 11/2017 | Kostrzewski et al. |
| 2017/0333136 A1 | 11/2017 | Hladio et al. |
| 2017/0340448 A1 | 11/2017 | Behzadi |
| 2017/0340456 A1 | 11/2017 | Behzadi |
| 2017/0348037 A1 | 12/2017 | Sexson et al. |
| 2017/0354368 A1 | 12/2017 | Behzadi |
| 2017/0354468 A1 | 12/2017 | Johnson et al. |
| 2017/0360493 A1 | 12/2017 | Zucker et al. |
| 2017/0360575 A1 | 12/2017 | Behzadi et al. |
| 2017/0367847 A1 | 12/2017 | Piriou et al. |
| 2018/0000543 A1 | 1/2018 | Hibner |
| 2018/0008324 A1 | 1/2018 | Cryder et al. |
| 2018/0008353 A1 | 1/2018 | Kostrzewski et al. |
| 2018/0008358 A1 | 1/2018 | Kostrzewski et al. |
| 2018/0021058 A1 | 1/2018 | Meglan |
| 2018/0021096 A1 | 1/2018 | Kostrzewski et al. |
| 2018/0028270 A1 | 2/2018 | Itkowitz et al. |

(56)     References Cited

U.S. PATENT DOCUMENTS

| | | | |
|---|---|---|---|
| 2018/0042650 | A1 | 2/2018 | Gao et al. |
| 2018/0042684 | A1 | 2/2018 | Kostrzewski et al. |
| 2018/0049823 | A1 | 2/2018 | Shelton, IV et al. |
| 2018/0049832 | A1 | 2/2018 | Eckert et al. |
| 2018/0050454 | A1 | 2/2018 | Linnell et al. |
| 2018/0078201 | A1 | 3/2018 | Behzadi |
| 2018/0078266 | A1 | 3/2018 | Fry et al. |
| 2018/0092648 | A1 | 4/2018 | Sun et al. |
| 2018/0092757 | A1 | 4/2018 | Behzadi et al. |
| 2018/0110573 | A1 | 4/2018 | Kostrzewski |
| 2018/0111273 | A1 | 4/2018 | Linnell et al. |
| 2018/0147018 | A1 | 5/2018 | Crawford et al. |
| 2018/0168539 | A1 | 6/2018 | Singh et al. |
| 2018/0168747 | A1 | 6/2018 | Kopp et al. |
| 2018/0185100 | A1 | 7/2018 | Weinstein et al. |
| 2018/0185107 | A1 | 7/2018 | Nikou et al. |
| 2018/0193171 | A1 | 7/2018 | van der Walt et al. |
| 2018/0199951 | A1 | 7/2018 | Chappuis et al. |
| 2018/0199999 | A1 | 7/2018 | Syverson et al. |
| 2018/0200002 | A1 | 7/2018 | Kostrzewski et al. |
| 2018/0200016 | A1 | 7/2018 | Chappuis et al. |
| 2018/0214223 | A1 | 8/2018 | Turner |
| 2018/0221097 | A1 | 8/2018 | Bonutti |
| 2018/0250077 | A1 | 9/2018 | Xu et al. |
| 2018/0250086 | A1 | 9/2018 | Grubbs |
| 2018/0250144 | A1 | 9/2018 | Li et al. |
| 2018/0256259 | A1 | 9/2018 | Crawford |
| 2018/0263714 | A1 | 9/2018 | Kostrzewski et al. |
| 2018/0289432 | A1 | 10/2018 | Kostrzewski et al. |
| 2018/0325608 | A1* | 11/2018 | Kang ..................... A61B 34/20 |
| 2019/0090966 | A1* | 3/2019 | Kang ................. A61B 17/1671 |
| 2019/0159848 | A1 | 5/2019 | Quaid et al. |
| 2019/0187804 | A1 | 6/2019 | Linnell |
| 2019/0231447 | A1 | 8/2019 | Ebbitt et al. |
| 2020/0015917 | A1 | 1/2020 | Cavalier et al. |

FOREIGN PATENT DOCUMENTS

| | | |
|---|---|---|
| CN | 101700184 B | 1/2011 |
| CN | 101579269 B | 4/2011 |
| CN | 101853333 B | 11/2012 |
| EP | 0203370 A1 | 12/1986 |
| WO | 2003090974 A1 | 11/2003 |
| WO | 2009092164 A1 | 7/2009 |
| WO | 2011062910 A1 | 5/2011 |
| WO | 2011063715 A1 | 6/2011 |
| WO | 2013075500 A1 | 5/2013 |
| WO | 2013192598 A1 | 12/2013 |
| WO | 2014138916 A1 | 9/2014 |
| WO | 2014139023 A1 | 9/2014 |
| WO | 2014139024 A1 | 9/2014 |
| WO | 2015061638 A1 | 4/2015 |
| WO | 2015087335 A1 | 6/2015 |
| WO | 2015115807 A1 | 8/2015 |
| WO | 2015115809 A1 | 8/2015 |
| WO | 2015166487 A1 | 11/2015 |
| WO | 2015193479 A1 | 12/2015 |
| WO | 2016008880 A1 | 1/2016 |
| WO | 2016042152 A1 | 3/2016 |
| WO | 2016088130 A1 | 6/2016 |
| WO | 2016115243 A1 | 7/2016 |
| WO | 2016118744 A1 | 7/2016 |
| WO | 2017001851 A1 | 1/2017 |
| WO | 2017023825 A1 | 2/2017 |
| WO | 2017027331 A1 | 2/2017 |
| WO | 2017035592 A1 | 3/2017 |
| WO | 2017036340 A1 | 3/2017 |
| WO | 2017037113 A1 | 3/2017 |
| WO | 2017037127 A1 | 3/2017 |
| WO | 2017048736 A1 | 3/2017 |
| WO | 2017064719 A1 | 4/2017 |
| WO | 2017115227 A1 | 7/2017 |
| WO | 2017121874 A2 | 7/2017 |
| WO | 2017122202 A1 | 7/2017 |
| WO | 2017123506 A1 | 7/2017 |
| WO | 2017136550 A1 | 8/2017 |
| WO | 2017123506 A9 | 9/2017 |
| WO | 2017151607 A1 | 9/2017 |
| WO | 2017162981 A1 | 9/2017 |
| WO | 2017177046 A1 | 10/2017 |
| WO | 2017218423 A1 | 12/2017 |
| WO | 2017219207 A1 | 12/2017 |
| WO | 2017219208 A1 | 12/2017 |
| WO | 2018031752 A1 | 2/2018 |
| WO | 2018067784 A1 | 4/2018 |
| WO | 2018072003 A1 | 4/2018 |
| WO | 2019100148 A1 | 5/2019 |

OTHER PUBLICATIONS

English language abstract and machine-assisted English translation for CN 101700184 extracted from espacenet.com database on Oct. 1, 2018, 15 pages.

English language abstract and machine-assisted English translation for CN 101853333 extracted from espacenet.com database on Oct. 1, 2018, 13 pages.

English language abstract and machine-assisted English translation for CN 201422918 extracted from espacenet.com database on Oct. 1, 2018, 11 pages.

English language abstract and machine-assisted English translation for CN 201542641 extracted from espacenet.com database on Oct. 1, 2018, 15 pages.

English language abstract and machine-assisted English translation for EP 0 203 370 A1 extracted from espacenet.com database on Apr. 5, 2021, 10 pages.

English language abstract and machine-assisted English translation for WO 2015/115807 A1 extracted from espacenet.com database on Apr. 5, 2021, 9 pages.

English language abstract and machine-assisted English translation for WO 2015/115809 extracted from espacenet.com database on Oct. 1, 2018, 14 pages.

English language abstract and machine-assisted English translation for WO 2017/119208 extracted from espacenet.com database on Nov. 28, 2018, 11 pages.

English language abstract and machine-assisted English translation for WO 2017/162981 extracted from espacenet.com database on Oct. 1, 2018, 13 pages.

English language abstract and machine-assisted English translation for WO 2017/219207 A1 extracted from espacenet.com database on Apr. 5, 2021, 11 pages.

English language abstract and machine-assisted English translation for WO 2017/219208 A1 extracted from espacenet.com database on Apr. 5, 2021, 6 pages.

English language abstract and machine-assisted English translation of corresponding CN 101700184B for WO 2011/063715 extracted from espacenet.com database on Oct. 1, 2018, 15 pages.

English language abstract for WO 2013/075500 A1 extracted from espacenet.com database on Apr. 5, 2021, 2 pages.

English language abstract for WO 2017/036340 extracted from espacenet.com database on Oct. 3, 2018, 2 pages.

International Search Report for Application No. PCT/US2018/031999 dated Nov. 7, 2018, 5 pages.

International Search Report for Application No. PCT/US2019/060502 dated Apr. 6, 2020, 4 pages.

Invitation to Pay Additional Fees and Partial Search Report for Application No. PCT/US2018/031999 dated Sep. 12, 2018, 3 pages.

Roble De-La-Torre, Gabriel, "The Importance of the Sense of Touch in Virtual and Real Environments", International Society for Haptics, IEEE 2006, 7 pages.

Romero, Francisco et al., "Experimental and Analytical Validation of a Modular Acetabular Prosthesis in Total Hip Arthroplasty", Journal of Orthopaedic Surgery and Research, May 16, 2007, pp. 1-9.

International Search Report for Application No. PCT/US2021/024438 dated Sep. 24, 2021, 5 pages.

* cited by examiner

| A | | B | C | D | | E | | F | | | G |
| Haptic Device Operational Mode | Example | Feedback Provided to Haptic Device | Haptic Device Feedback Control Technique | Physical Screw Control Directed By | | Simulated Screw Control Directed By | | Haptic Device Operation Occurrence | | | Haptic Device Control Technique (input) |
| | | | | Haptic Device | Autonomous Robot Control | Haptic Device | Simulated Autonomous Robot Control | Before Autonomously Screwing Begins | Concurrently While Autonomously Screwing | Pause/Completion of Autonomous Screwing | |
|---|---|---|---|---|---|---|---|---|---|---|---|
| Autonomous Check Mode | A1 | | | | X* | N/A | | X | | | N/A |
| | A2 | | | | | | | | X | | |
| | A3 | | | | | | | | | X | |
| Manual Control Mode | M1 | X | Resistive Force | X | | N/A | | X | | | Force/Torque |
| | M2 | | | | | | | | | | Position |
| | M3 | | | | | | | | | | Velocity |
| | M4 | | | | | | | | | X | Force/Torque |
| | M5 | | | | | | | | | | Position |
| | M6 | | | | | | | | | | Velocity |
| Simulated Autonomous Check Mode | SA1 | | | N/A | | | X | X | | | N/A |
| | SA2 | | | | | | | | | X | |
| Simulated Manual Control Mode | SM1 | | | N/A | | X | | X | | | Force/Torque |
| | SM2 | | | | | | | | | | Position |
| | SM3 | | | | | | | | | | Velocity |
| | SM4 | | | | | | | | | X | Force/Torque |
| | SM5 | | | | | | | | | | Position |
| | SM6 | | | | | | | | | | Velocity |

* Optional

| A Haptic Device (Input) | B Controller Measurement | C | D Tool Control (Output) |
|---|---|---|---|
| Force/Torque | $F_{in}$ | Rotational Position | Input force mapped to degrees of screw rotation |
| | | Insertion Depth | Input force mapped to depth of screw insertion |
| | | Torque | Input force mapped to torque applied to screw |
| | | Velocity | Input force mapped to velocity of screw insertion |
| Position | $P_1$ Displacement $P_1 - P_0$ | Rotational Position | Input position or displacement mapped to degree(s) of screw rotation |
| | | Insertion Depth | Input position or displacement mapped to depth of screw insertion |
| | | Torque | Input position or displacement mapped to torque level to be applied to screw |
| | | Velocity | Input position or displacement mapped to velocity of screw insertion |
| Velocity | $\dfrac{P_1 - P_0}{T_1 - T_0}$ | Rotational Position | Input velocity mapped to a position of the screw |
| | | Insertion Depth | Input velocity mapped to a depth of screw insertion |
| | | Torque | Input velocity mapped to torque applied to screw |
| | | Velocity | Input velocity mapped to a velocity of screw insertion |

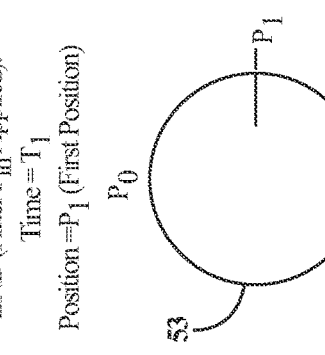

END (After $F_{in}$ Applied):
Time = $T_1$
Position = $P_1$ (First Position)

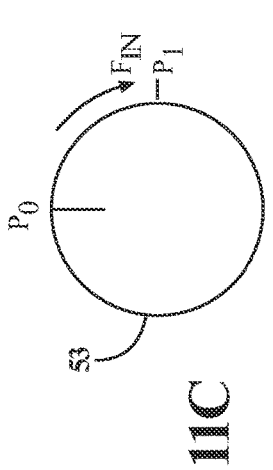

START:
Time = $T_0$
Position = $P_0$ (Home Position)

FIG. 11C

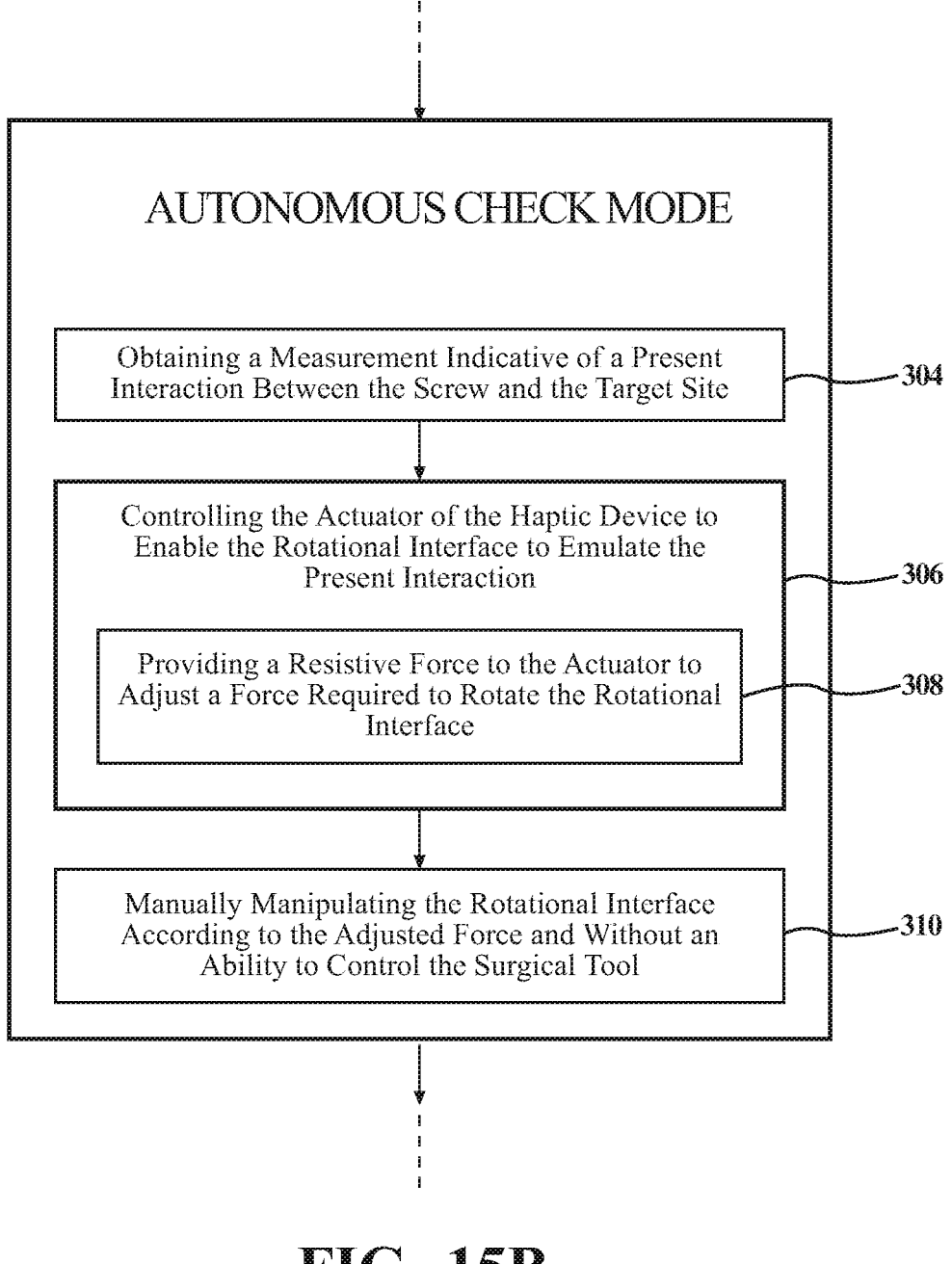

AUTONOMOUS CHECK MODE

Obtaining a Measurement Indicative of a Present Interaction Between the Screw and the Target Site — 304

Controlling the Actuator of the Haptic Device to Enable the Rotational Interface to Emulate the Present Interaction — 306

Providing a Resistive Force to the Actuator to Adjust a Force Required to Rotate the Rotational Interface — 308

Manually Manipulating the Rotational Interface According to the Adjusted Force and Without an Ability to Control the Surgical Tool — 310

FIG. 15B

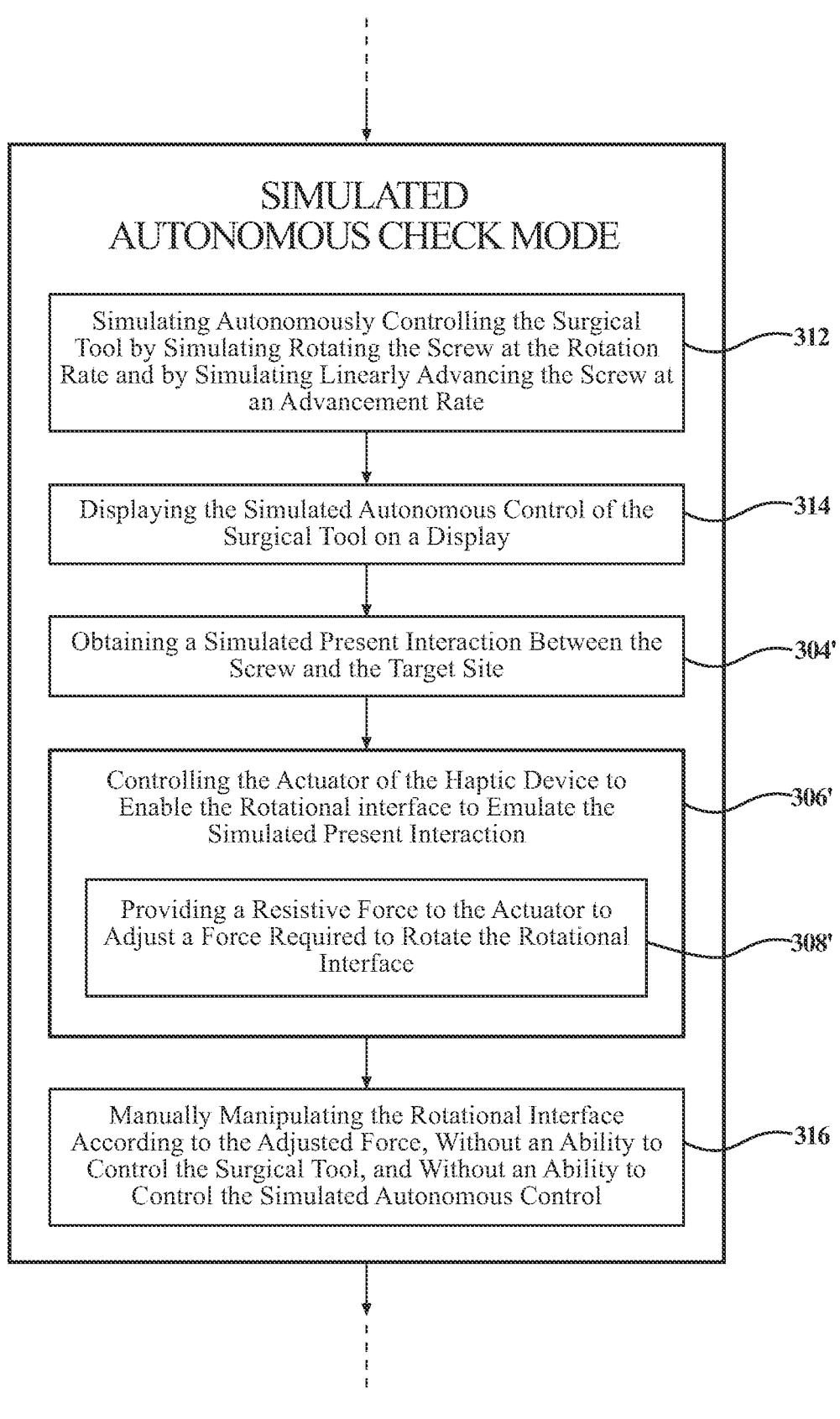

SIMULATED
AUTONOMOUS CHECK MODE

Simulating Autonomously Controlling the Surgical Tool by Simulating Rotating the Screw at the Rotation Rate and by Simulating Linearly Advancing the Screw at an Advancement Rate ⟶ 312

Displaying the Simulated Autonomous Control of the Surgical Tool on a Display ⟶ 314

Obtaining a Simulated Present Interaction Between the Screw and the Target Site ⟶ 304'

Controlling the Actuator of the Haptic Device to Enable the Rotational interface to Emulate the Simulated Present Interaction ⟶ 306'

Providing a Resistive Force to the Actuator to Adjust a Force Required to Rotate the Rotational Interface ⟶ 308'

Manually Manipulating the Rotational Interface According to the Adjusted Force, Without an Ability to Control the Surgical Tool, and Without an Ability to Control the Simulated Autonomous Control ⟶ 316

FIG. 15D

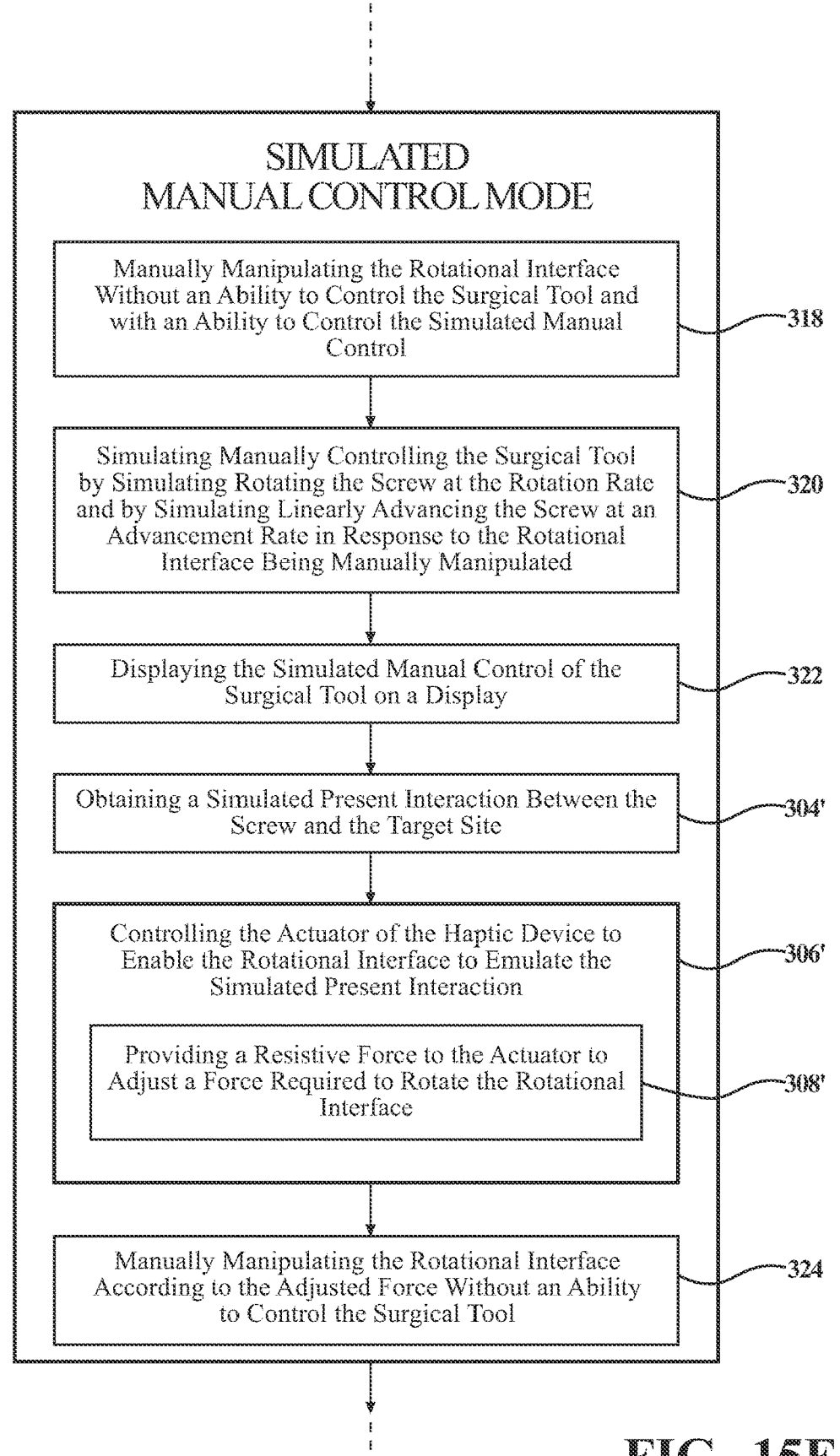

SIMULATED
MANUAL CONTROL MODE

Manually Manipulating the Rotational Interface Without an Ability to Control the Surgical Tool and with an Ability to Control the Simulated Manual Control — 318

Simulating Manually Controlling the Surgical Tool by Simulating Rotating the Screw at the Rotation Rate and by Simulating Linearly Advancing the Screw at an Advancement Rate in Response to the Rotational Interface Being Manually Manipulated — 320

Displaying the Simulated Manual Control of the Surgical Tool on a Display — 322

Obtaining a Simulated Present Interaction Between the Screw and the Target Site — 304'

Controlling the Actuator of the Haptic Device to Enable the Rotational Interface to Emulate the Simulated Present Interaction — 306'

Providing a Resistive Force to the Actuator to Adjust a Force Required to Rotate the Rotational Interface — 308'

Manually Manipulating the Rotational Interface According to the Adjusted Force Without an Ability to Control the Surgical Tool — 324

FIG. 15E

ROBOTIC SPINE SURGERY SYSTEM AND METHODS WITH HAPTIC INTERFACE

CROSS-REFERENCE TO RELATED APPLICATIONS

The subject application claims priority to and all the benefits of U.S. Provisional Patent Application No. 63/001,019, filed Mar. 27, 2020, the entire disclosure of which is hereby incorporated by reference.

STATEMENT UNDER 37 CFR 1.77 (b)(6) REGARDING PRIOR DISCLOSURES

The disclosure of United States patent application U.S. Ser. No. 16/184,376, filed Nov. 8, 2018, entitled "Robotic Spine Surgery System and Methods", was made by the inventor or a joint inventor, or the subject matter was obtained directly or indirectly from the inventor or a joint inventor.

BACKGROUND

Robotic surgical systems for performing surgical procedures in a patient's spine are well known. For instance, robotic surgical systems are currently utilized to place pedicle screws in a patient's spine.

When a patient requires surgery that involves placing pedicle screws, pre-operative imaging and/or intra-operative imaging is often employed to visualize the patient's anatomy that requires treatment—in this case the patient's spine. A surgeon then plans where to place the pedicle screws with respect to the images and/or with respect to a 3-D model created from the images. Planning includes determining a position and orientation (i.e., pose) of each pedicle screw with respect to the particular vertebra in which they are being placed, e.g., by identifying the desired pose in the images and/or the 3-D model. Once the plan is set, then the plan is transferred to the robotic surgical system for execution.

Typically, the robotic surgical system comprises a robotic manipulator that positions a tool guide above the patient and along a desired trajectory that is aligned with the desired orientation of the pedicle screw to be placed. The robotic surgical system also comprises a navigation system to determine a location of the tool guide with respect to the patient's anatomy so that the robotic manipulator can place the tool guide along the desired trajectory according to the surgeon's plan. In some cases, the navigation system includes tracking devices attached to the manipulator and to the patient so that the robotic surgical system can monitor and respond to movement of the patient during the surgical procedure by moving the tool guide as needed to maintain the desired trajectory.

Once the tool guide has been positioned in alignment with the desired trajectory, the robotic manipulator is controlled to maintain the alignment. Thereafter, a surgeon positions a cannula through the tool guide and adjacent to the vertebra. The surgeon inserts a conventional drilling tool into the cannula to drill a pilot hole for the pedicle screw. The surgeon then removes the drilling tool and inserts the pedicle screw into position in the pilot hole with a pedicle screwdriver. In this methodology, the robotic manipulator is somewhat underutilized as the robotic manipulator plays little to no role in drilling the pilot hole or inserting the pedicle screw.

On the other hand, the disclosure of U.S. Ser. No. 16/184,376, filed Nov. 8, 2018, entitled "Robotic Spine Surgery System and Methods", discloses a technique by which the robotic system can be utilized to autonomously control a surgical tool to rotate the screw at a rotational rate about the rotational axis and to linearly advance the screw at an advancement rate along the planned trajectory. Despite utilization of the robotic manipulator in this methodology, the surgeon is removed from being in the direct contact or control with the force, energy, material and information flow involved while interacting with tissue. In turn, this may lead to a loss of haptic and sensory information that a surgeon is accustomed to for monitoring and assessing the tissue interaction process during the surgical procedure. The inability of the surgeon to assess the process due to lack of sensory input can lead, amongst other things, to loss of surgeon confidence, emotional stress, poor procedural efficacy, and an inability to react to unforeseen circumstances that are not captured by the robotic solution but otherwise perceivable to the surgeon.

SUMMARY

A first aspect of the disclosure involves a robotic surgical system comprising a robotic manipulator; a surgical tool coupled to the robotic manipulator and configured to interface with a screw and to rotate the screw about a rotational axis; a haptic device comprising an actuator and a rotational interface coupled to the actuator and the rotational interface being configured to be manually manipulatable by a hand of an operator; a navigation system configured to track a position of a target site; and one or more controllers coupled to the robotic manipulator, the haptic device and the navigation system, and the one or more controllers configured to: control movement of the robotic manipulator to maintain the rotational axis of the surgical tool along a planned trajectory with respect to the target site based on the tracked position of the target site; autonomously control the surgical tool to rotate the screw at a rotational rate about the rotational axis and to linearly advance the screw at an advancement rate along the planned trajectory wherein the rotational rate and the advancement rate are predetermined and proportional to a known thread geometry of the screw; obtain a measurement indicative of a present interaction between the screw and the target site; and based on the obtained measurement, control the haptic device to enable the rotational interface to emulate the present interaction between the screw and the target site.

In some implementations, the rotational interface includes but is not limited to any one or more of: a knob, wheel, a rotary switch, or a dial.

In some implementations, the haptic device comprises a linear interface instead of a rotational interface, such as but not limited to a linear push button, a linear switch, a linear trigger, or a linear slider.

In some implementations, the one or more controllers emulate the present interaction between the screw and the target site by being configured to control the actuator of the haptic device.

In some implementations, the one or more controllers further emulate the present interaction between the screw and the target site by being configured to provide a resistive force to the actuator to adjust a force required to rotate the rotational interface by the hand of the operator, wherein the force required to rotate the rotational interface reflects a present force required to rotate the screw relative to the target site.

In some implementations, the one or more controllers are configured to resist mechanical motion of the interface utilizing means other than, or in addition to, the actuator. For example, to influence of movement of the interface, the haptic device may utilize mechanical components including but not limited to, biasing mechanisms, detents, ratchets, and/or gear systems, etc.; electrical components such as but not limited to, inductive, capacitive, and/or resistance elements; magnetic components; electro-magnetic components; electro-mechanical components; hydraulic components; and/or pneumatic components.

In some implementations, the one or more controllers further emulate the present interaction between the screw and the target site by being configured to limit a range of motion of the interface.

In some implementations, the one or more controllers are further configured to initiate an autonomous check mode wherein the rotational interface is manually manipulatable according to the adjusted force to provide the operator with haptic feedback reflecting the present force required to rotate the screw relative to the target site; and without an ability to control the surgical tool to rotate the screw.

In some implementations, in response to a condition or a command, the one or more controllers are further configured to initiate the autonomous check mode concurrent to autonomously controlling the surgical tool.

In some implementations, in response to a condition or a command, the one or more controllers are further configured to initiate the autonomous check mode after stopping or pausing autonomously controlling the surgical tool to stop rotation of the screw.

In some implementations, in response to a condition or a command, the one or more controllers are further configured to resume autonomously controlling the surgical tool to rotate the screw after autonomous control of the surgical tool is stopped or paused to stop rotation of the screw.

In some implementations, the one or more controllers are further configured to initiate a manual control mode wherein the rotational interface is manually manipulatable with an ability to control one of the rotational rate of the screw or the advancement rate of the screw based on the operator manually manipulating the rotational interface; the one or more controllers are configured to control the surgical tool to rotate the screw at the rotational rate about the rotational axis and to linearly advance the screw at the advancement rate along the planned trajectory in response to the rotational interface being manually manipulated to control one of the rotational rate of the screw or the advancement rate of the screw; and the rotational interface is manually manipulatable according to the adjusted force to provide the operator with haptic feedback reflecting the present force required to rotate the screw relative to the target site.

In some implementations, in response to a condition or a command, the one or more controllers are further configured to initiate the manual control mode after stopping or pausing autonomously controlling the surgical tool to stop rotation of the screw.

In some implementations, in response to a condition or a command, the one or more controllers are further configured to switch from the manual control mode to resuming autonomously controlling the surgical tool to rotate the screw.

In some implementations, the haptic device is configured to trigger the condition or the command.

In some implementations, the robotic surgical system further comprises a sensor being configured to obtain the measurement indicative of the present interaction between the screw and the target site, the one or more controllers being coupled to the sensor.

In some implementations, the one or more controllers are configured to: determine that a condition exists during control of the screw; and in response to determining that the condition exists, provide the operator with haptic feedback regarding the condition by controlling the actuator of the haptic device to prevent an ability to rotate the rotational interface.

In some implementations, the navigation system is further configured to: determine a position of the screw relative to an anatomical model of the target site that is registered to the target site, the navigation system including predetermined data indicative of expected interactions between the screw and the anatomical model at a plurality of positions of the screw relative to the anatomical model; and obtain the measurement indicative of the present interaction between the screw and the target site based on the determined position of the screw relative to the anatomical model and the predetermined data.

In some implementations, the rotational rate and the advancement rate are proportional to the known thread geometry according to a relationship $$\frac{\delta\theta}{\delta t} = \frac{\delta D}{\delta t} * \frac{\text{Pitch}}{2\pi},$$

wherein $$\frac{\delta\theta}{\delta t}$$

is the rotational rate, $$\frac{\delta D}{\delta t}$$

is tie advancement rate, and rich is a number of threads per unit length of the screw.

In some implementations, the haptic device is further defined as a hand-held pendant.

In some implementations, the haptic device is a rotational interface, such as but not limited to a knob, a rotary switch, or a dial.

In some implementations, any implant can be utilized instead of a screw, such as a spinal implant, such as a rod, anchor, spacer, cage, or a plate.

In some implementations, the screw is more specifically a self-tapping screw.

In some implementations, the haptic device is remotely spaced apart from the robotic manipulator and the surgical tool.

In some implementations, the haptic device is directly attached to the robotic manipulator or the surgical tool.

In some implementations, the one or more controllers are further configured to receive an input from the operator to selectively adjust one or more of: the resistive force provided to the actuator; and a sensitivity of the rotational interface's ability to control the surgical tool to rotate the screw.

In some implementations, the robotic surgical system further comprises a display and wherein the one or more controllers are further configured to initiate a simulated autonomous check mode wherein the one or more controllers are configured to: simulate autonomously controlling the surgical tool by rotating the screw at the rotational rate about the rotational axis and linearly advancing the screw at the advancement rate along the planned trajectory; display the simulated autonomous control of the surgical tool on the display; obtain a simulated present interaction between the screw and the target site; and based on the simulated present interaction, control the actuator of the haptic device to enable the rotational interface to emulate the simulated present interaction between the screw and the target site by being configured to provide a resistive force to the actuator to adjust a force required to rotate the rotational interface by the hand of the operator, wherein the force required to rotate the rotational interface reflects a simulated present force required to rotate the screw relative to the target site; wherein the rotational interface is manually manipulatable: according to the adjusted force to provide the operator with haptic feedback reflecting the simulated present force; and without an ability to control the surgical tool to rotate the screw and without an ability to control the simulated autonomous control of the surgical tool.

In some implementations, the one or more controllers are further configured to initiate the simulated autonomous check mode prior to autonomously controlling the surgical tool.

In some implementations, the robotic surgical system further comprises a display and wherein the one or more controllers are further configured to initiate a simulated manual control mode wherein the rotational interface is manually manipulatable without an ability to control the surgical tool to rotate the screw and with an ability to control one of the rotational rate of the screw or the advancement rate of the screw during the simulated manual control of the surgical tool based on the operator manually manipulating the rotational interface, and wherein the one or more controllers are configured to: simulate manually controlling the surgical tool by rotating the screw at the rotational rate about the rotational axis and linearly advancing the screw at the advancement rate along the planned trajectory in response to the rotational interface being manually manipulated to control one of the rotational rate of the screw or the advancement rate of the screw; display the simulated manual control of the surgical tool on the display; obtain a simulated present interaction between the screw and the target site; and based on the simulated present interaction, control the actuator of the haptic device to enable the rotational interface to emulate the simulated present interaction between the screw and the target site by being configured to provide a resistive force to the actuator to adjust a force required to rotate the rotational interface by the hand of the operator, wherein the force required to rotate the rotational interface reflects a simulated present force required to rotate the screw relative to the target site, and wherein the rotational interface is manually manipulatable according to the adjusted force to provide the operator with haptic feedback reflecting the simulated present force.

In some implementations, in response to a condition or a command, the one or more controllers are further configured to initiate the simulated manual control mode after stopping or pausing autonomously controlling the surgical tool to stop rotation of the screw.

A second aspect of the disclosure involves a method of operating the robotic surgical system according to the first aspect of the disclosure, and optionally, according to any of the implementations within this section. The first and second aspects of the disclosure are optionally implemented according to any of the implementations within this section.

A third aspect of the disclose involves a robotic surgical system comprising: a robotic manipulator; a surgical tool coupled to the robotic manipulator and configured to interface with a screw and to rotate the screw about a rotational axis; a haptic device comprising an actuator and a rotational interface coupled to the actuator and the rotational interface being configured to be manually manipulatable by a hand of an operator; a navigation system configured to track a position of a target site; and one or more controllers coupled to the robotic manipulator, the haptic device and the navigation system, and the one or more controllers configured to: control movement of the robotic manipulator to maintain the rotational axis of the surgical tool along a planned trajectory with respect to the target site based on the tracked position of the target site; receive control input from the haptic device wherein the rotational interface is manually manipulatable with an ability to control one of the rotational rate of the screw or the advancement rate of the screw based on the operator manually manipulating the rotational interface; in response to control input from the haptic device, control the surgical tool to rotate the screw at a rotational rate about the rotational axis and to linearly advance the screw at an advancement rate along the planned trajectory wherein the rotational rate and the advancement rate are predetermined and proportional to a known thread geometry of the screw; obtain a measurement indicative of a present interaction between the screw and the target site; and based on the obtained measurement, control the actuator of the haptic device to enable the rotational interface to emulate the present interaction between the screw and the target site.

A fourth aspect of the disclosure involves a method of operating the robotic surgical system according to the third aspect of the disclosure, and optionally, according to any of the implementations within this section. The third and fourth aspects of the disclosure are optionally implemented according to any of the implementations within this section.

A fifth aspect of the disclosure involves a robotic surgical system comprising: a robotic manipulator; a surgical tool coupled to the robotic manipulator and configured to rotate about a rotational axis; a haptic device comprising an actuator and an interface coupled to the actuator and the interface being configured to be manually manipulatable by a hand of an operator; a navigation system configured to track a position of a target site; and one or more controllers coupled to the robotic manipulator, the haptic device and the navigation system, and the one or more controllers configured to: control movement of the robotic manipulator to maintain the rotational axis of the surgical tool along a planned trajectory with respect to the target site based on the tracked position of the target site; autonomously control the surgical tool to rotate the surgical tool at a rotational rate about the rotational axis and to linearly advance the surgical tool at an advancement rate along the planned trajectory; obtain a measurement indicative of a present interaction between the surgical tool and the target site; and based on the obtained measurement, control the actuator of the haptic device to enable the rotational interface to emulate the present interaction between the surgical tool and the target site.

A sixth aspect of the disclosure involves a method of operating the robotic surgical system according to the fifth aspect of the disclosure, and optionally, according to any of the implementations within this section. The fifth and sixth aspects of the disclosure are optionally implemented according to any of the implementations within this section.

A seventh aspect of the disclosure involves a simulation system comprising: a haptic device comprising an actuator and a rotational interface coupled to the actuator and the rotational interface being configured to be manually manipulatable by a hand of an operator; a display device; and one or more controllers coupled to the haptic device and the display device, and the one or more controllers configured to provide a simulation, on the display device, the simulation system configured to: provide a simulated surgical tool configured to interface with a simulated screw and to rotate the simulated screw about a rotational axis along a simulated trajectory relative to a simulated target site; provide simulated control of the simulated surgical tool to rotate the simulated screw at a rotational rate about the rotational axis and to linearly advance the simulated screw at an advancement rate along the simulated trajectory wherein the rotational rate and the advancement rate are predetermined and proportional to a known thread geometry of the simulated screw; obtain a simulated present interaction between the simulated screw and the simulated target site; and based on the simulated present interaction, control the haptic device to enable the rotational interface to emulate the simulated present interaction between the simulated screw and the simulated target site.

An eighth aspect of the disclosure involves a method of operating the simulation system according to the seventh aspect of the disclosure, and optionally, according to any of the implementations within this section. The seventh and eighth aspects of the disclosure are optionally implemented according to any of the implementations within this section.

BRIEF DESCRIPTION OF THE DRAWINGS

FIG. 11A is a table illustrating various operational modes, including an Autonomous Check Mode, a Manual Control Mode, a Simulated Autonomous Check Mode, and a Simulated Manual Control Mode, and parameters for the haptic device.

FIG. 11B is a table illustrating various techniques for controlling insertion of a pedicle screw based on an input from the haptic device during the Manual Control Mode.

FIG. 11C is an illustration of a rotational interface of the haptic device being manually manipulated from a home position to a non-home position.

8

Figure 12A:
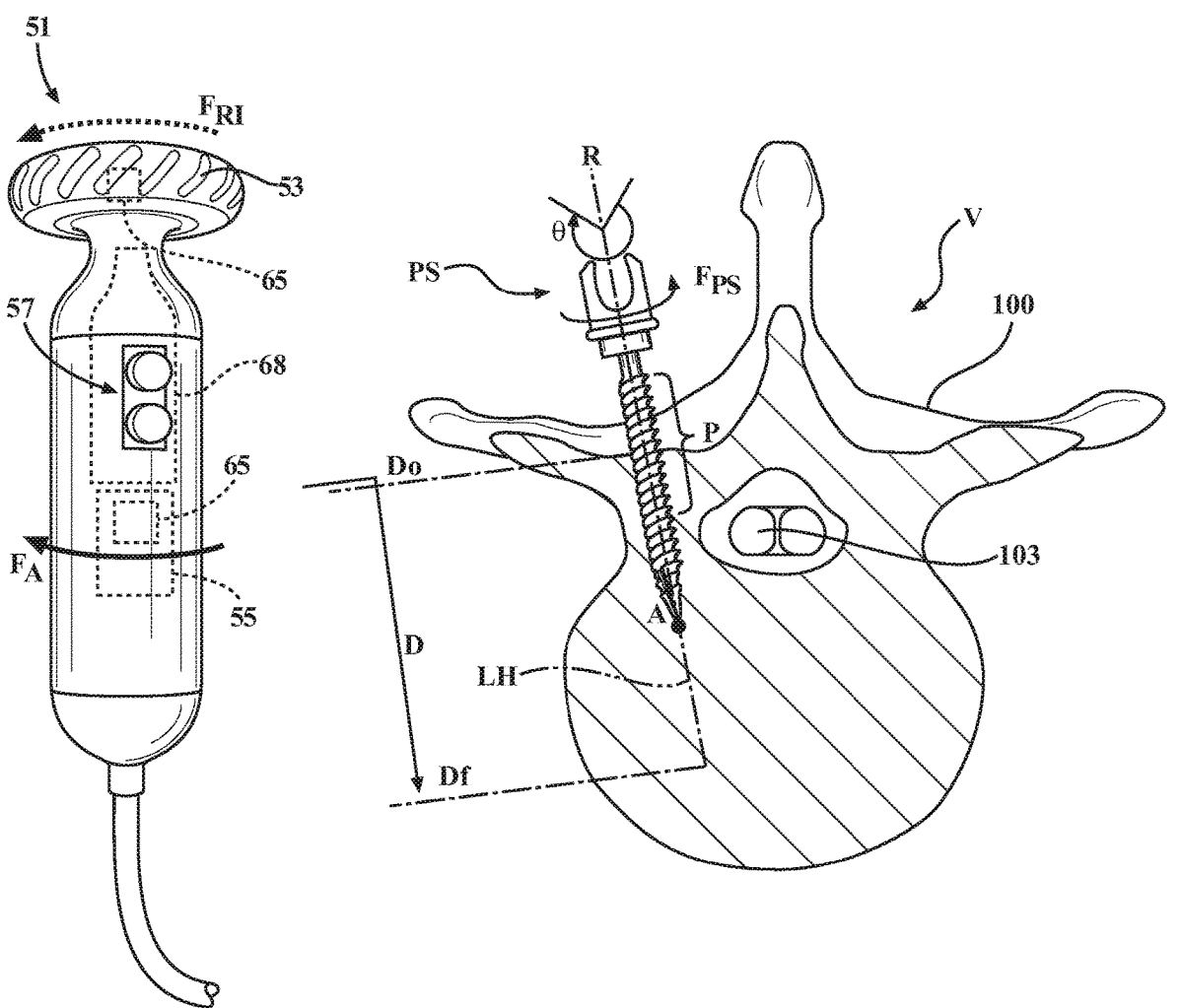

FIG. 12A is an illustration of the haptic device providing haptic feedback to an operator while the pedicle screw is inserted during the Autonomous Check Mode.

Figure 12B:
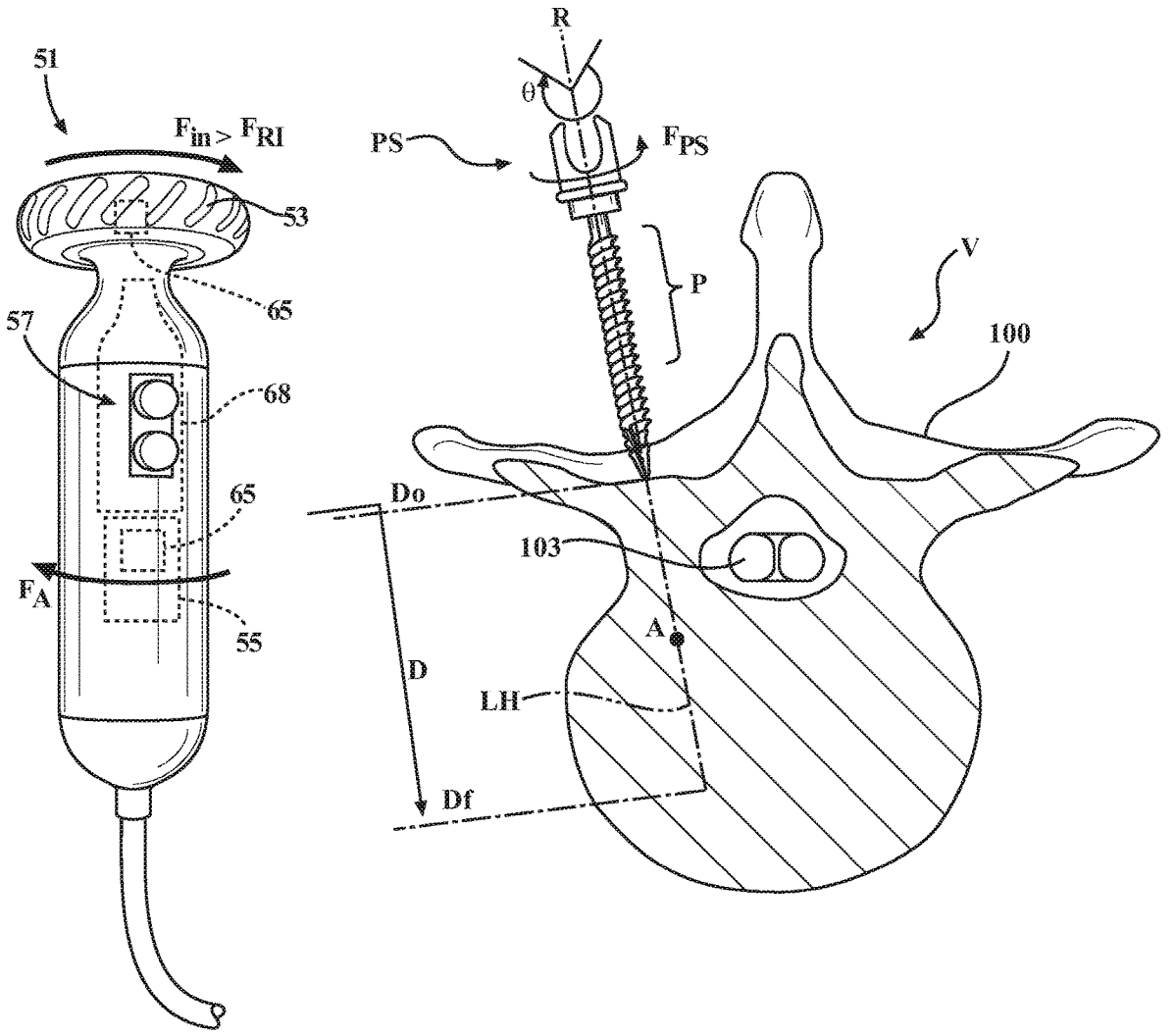

FIG. 12B is an illustration of the haptic device providing haptic feedback to the operator while the pedicle screw is inserted during the Manual Control Mode.

Figures 13A, 13B:
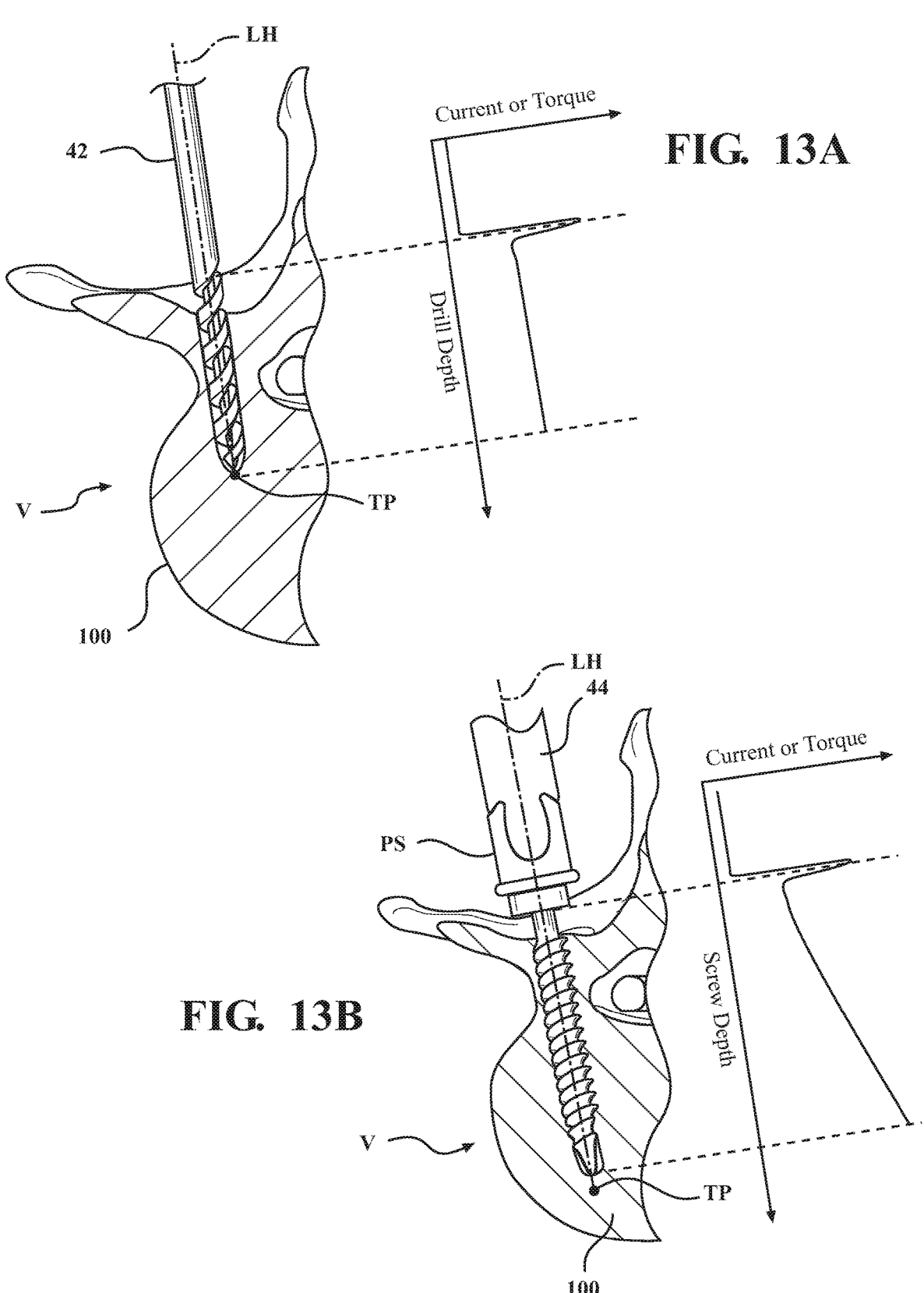

FIGS. 13A and 13B are illustrations showing electrical current output vs. depth, which can be used to verify that drilling and pedicle screw insertion is according to the operator's plan.

Figure 14A:
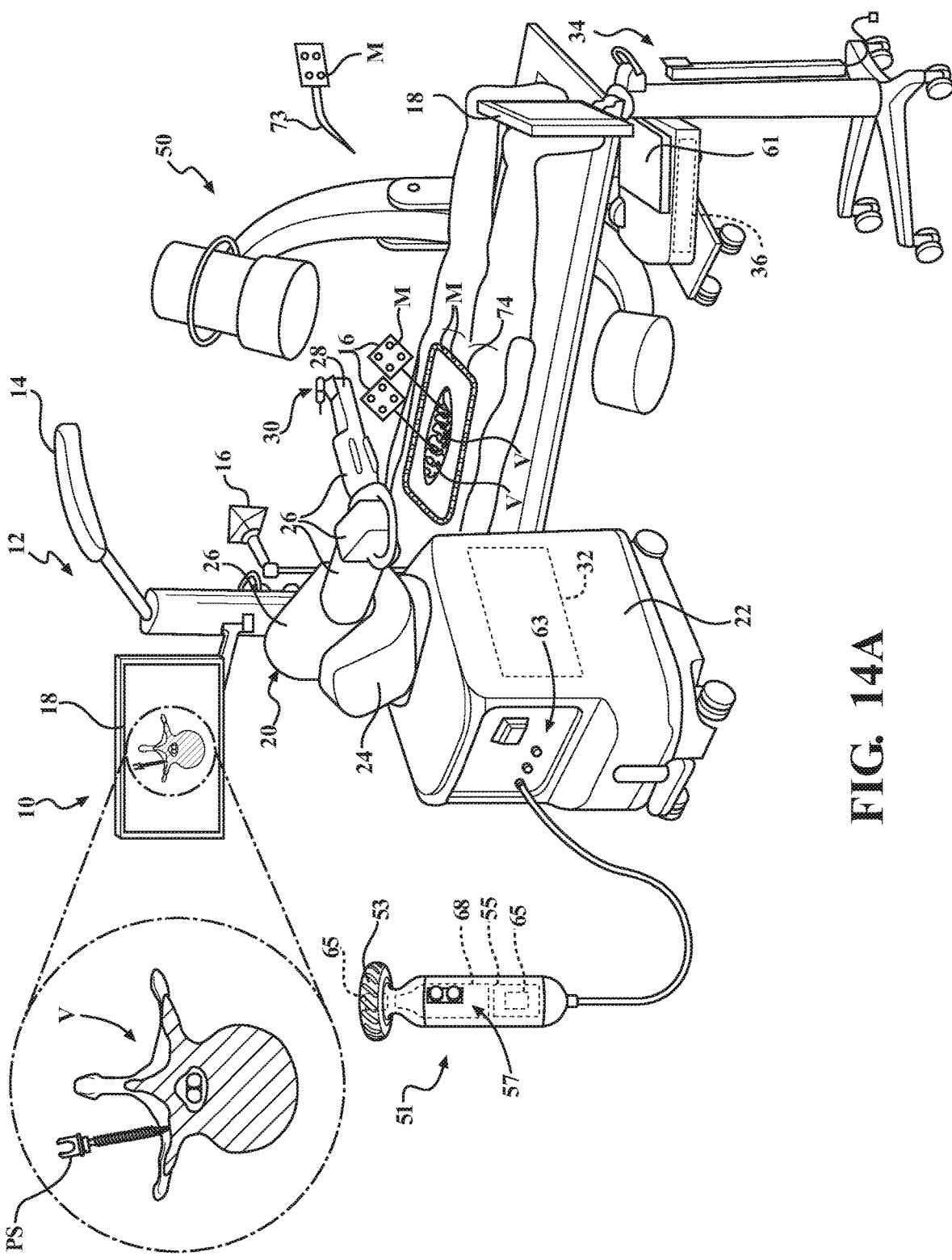

FIG. 14A is a perspective view of robotic surgical system including the haptic device and displaying a simulation of the pedicle screw being inserted, according to one example.

Figure 14B:
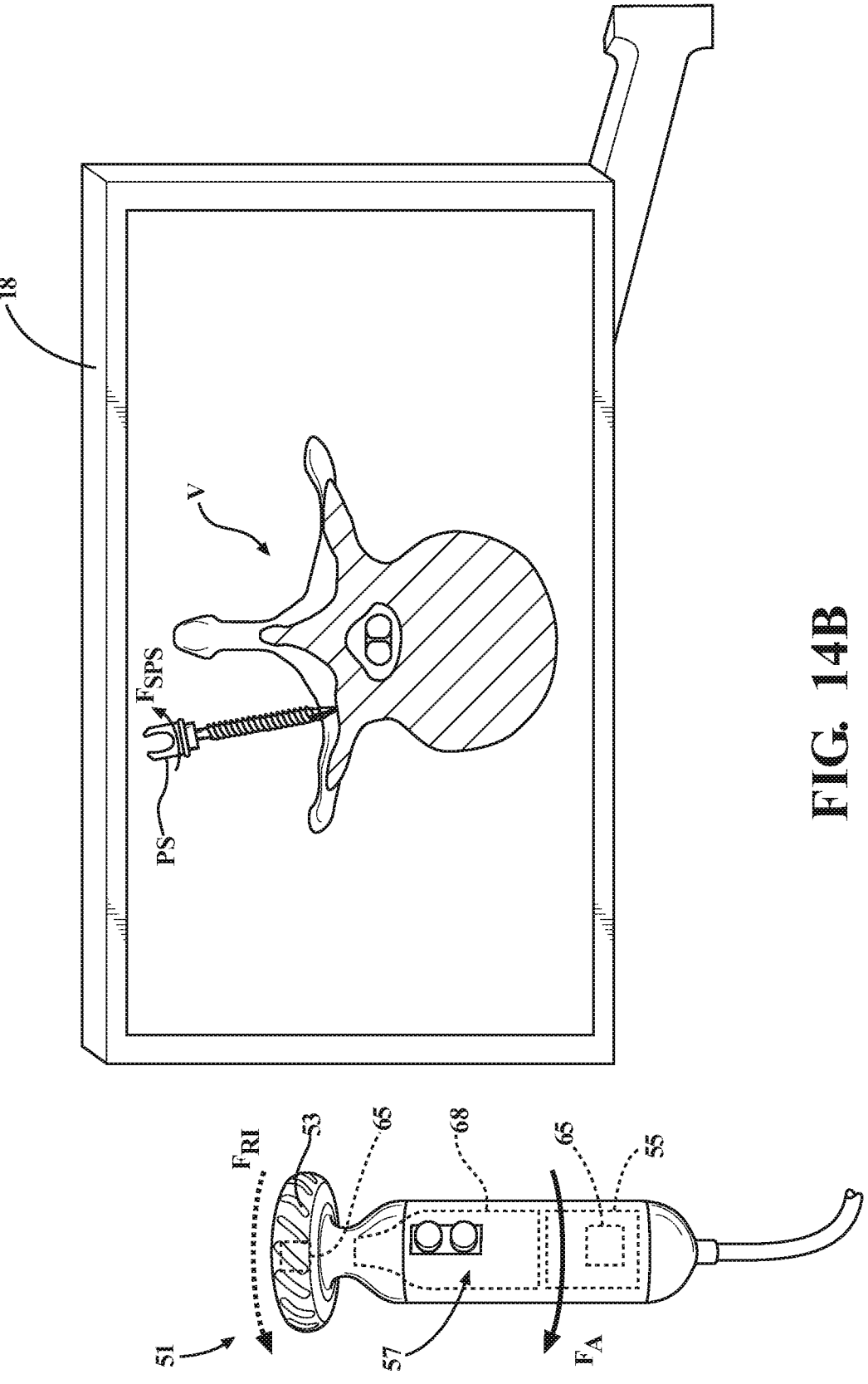

FIG. 14B is an illustration of the haptic device providing haptic feedback to the operator while the pedicle screw is inserted during a Simulated Autonomous Check Mode.

Figure 14C:
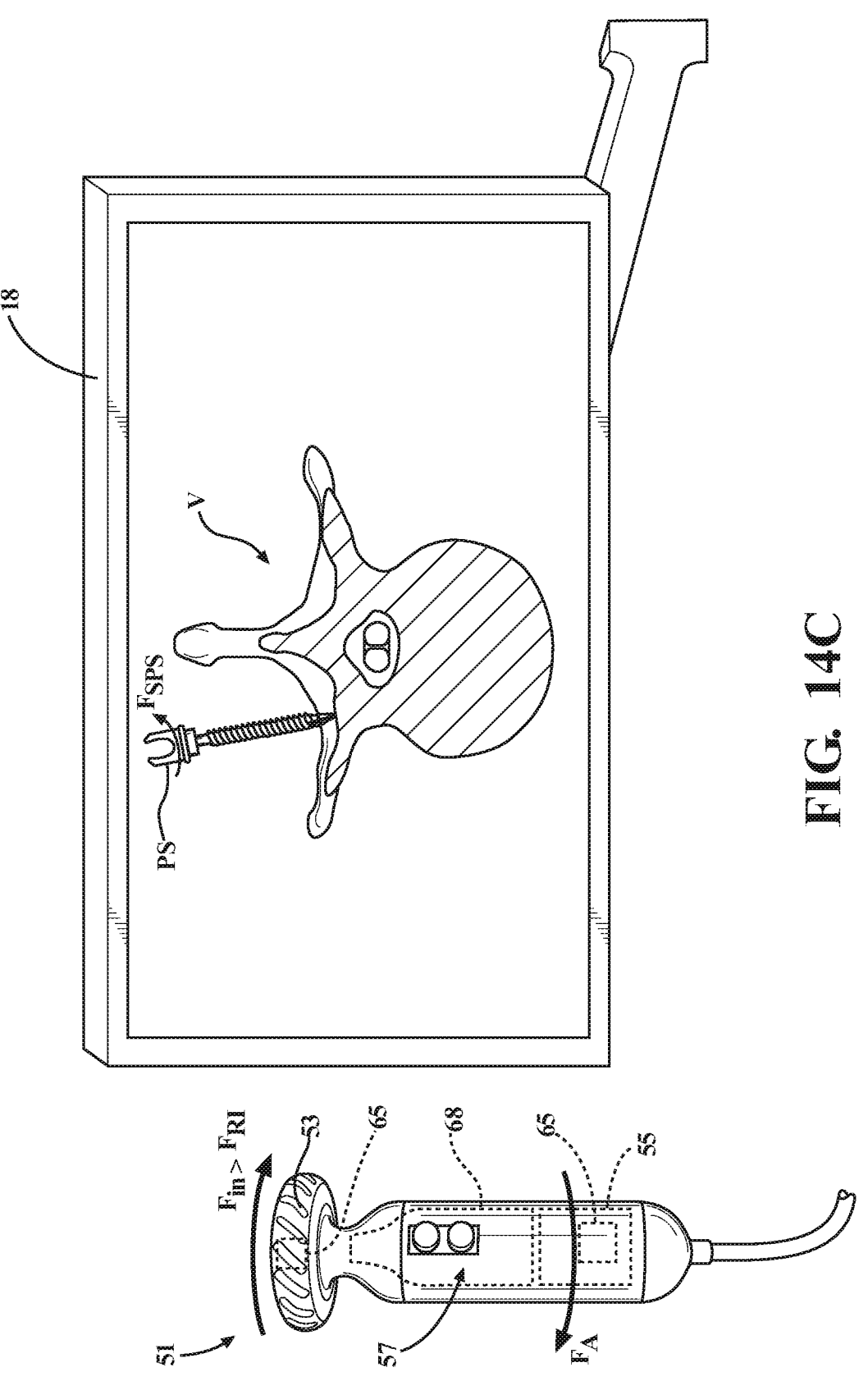

FIG. 14C is an illustration of the haptic device providing haptic feedback to the operator while the pedicle screw is inserted during a Simulated Manual Control Mode.

Figure 15A:
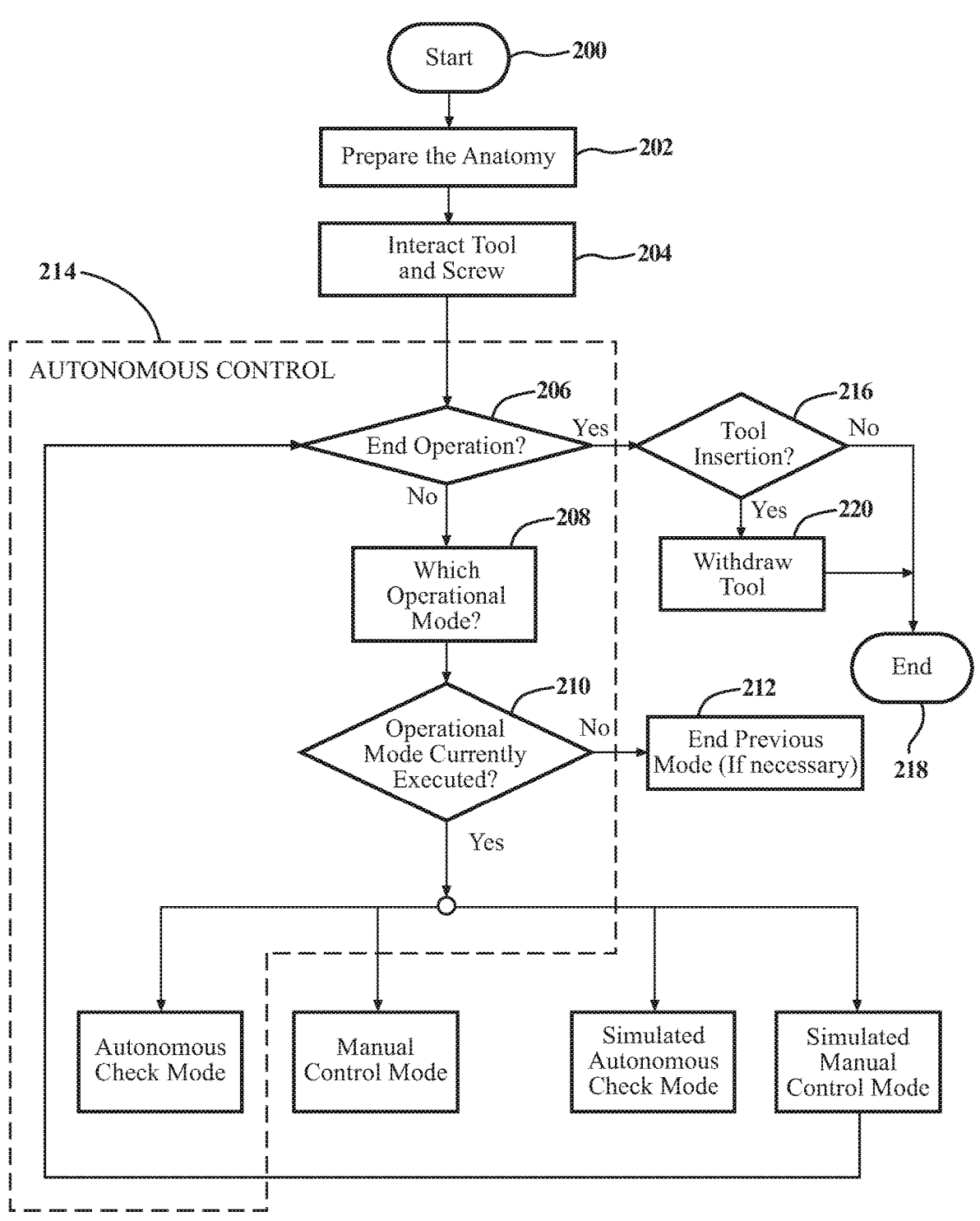

FIG. 15A is a flow chart of a method of operating the robotic surgical system using the haptic device.

FIG. 15B is a flow chart of sample steps to execute the Autonomous Check Mode.

Figure 15C:
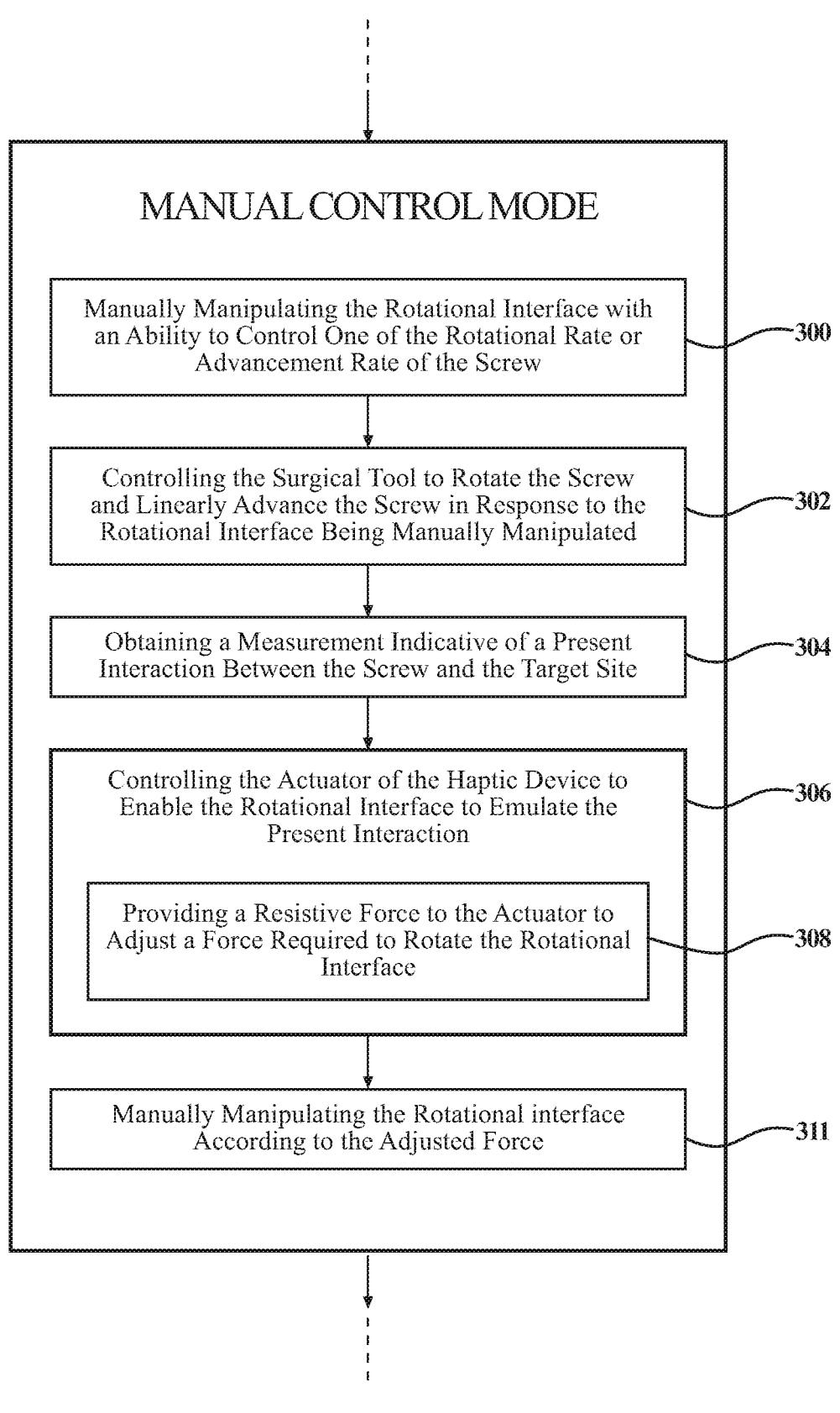

FIG. 15C is a flow chart of sample steps to execute the Manual Control Mode.

FIG. 15D is a flow chart of sample steps to execute the Simulated Autonomous Check Mode.

FIG. 15E is a flow chart of sample steps to execute the Simulated Manual Control Mode.

Figure 15F:
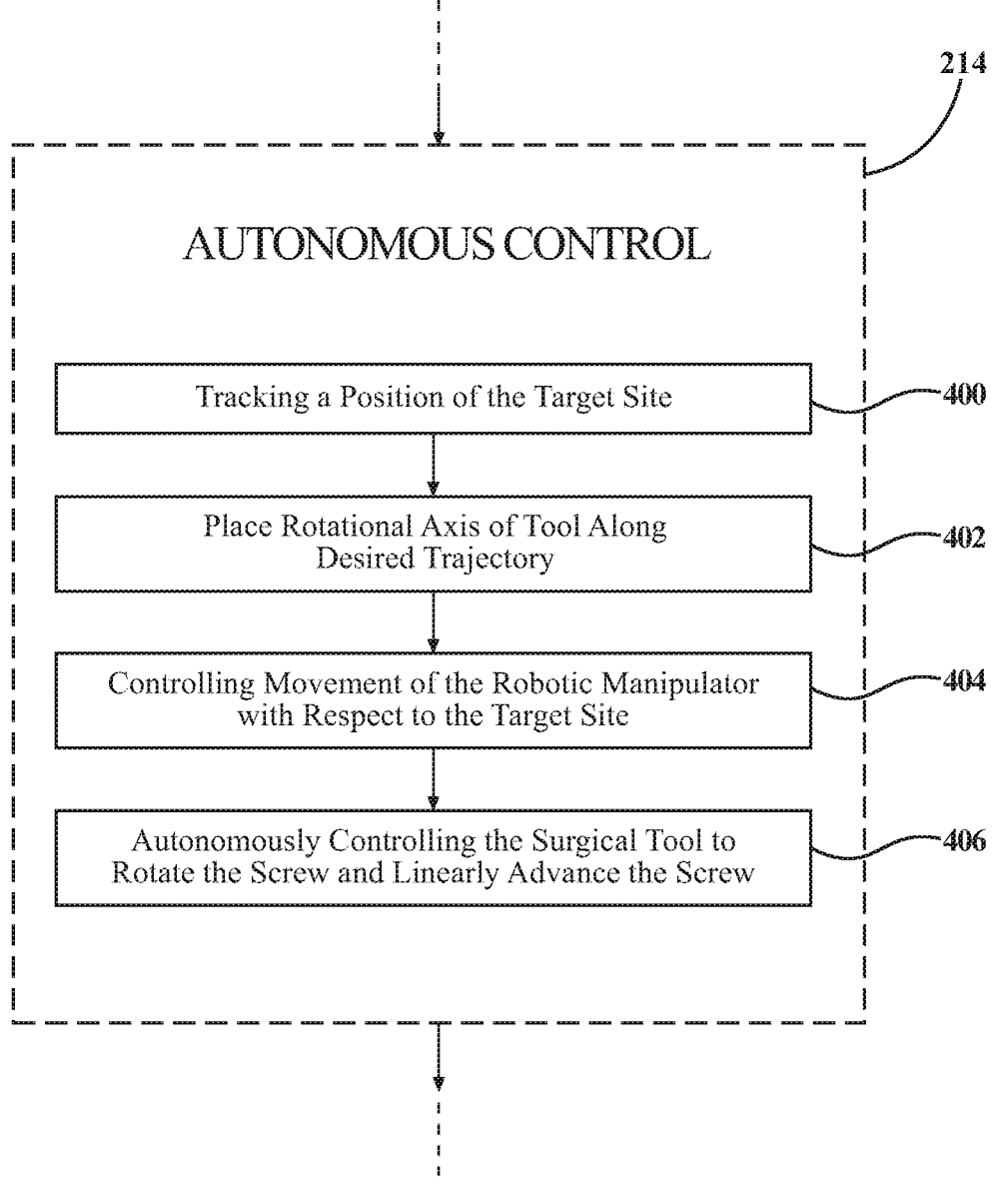

FIG. 15F is a flow chart of sample steps carried out during the surgical procedure to autonomously control insertion of the pedicle screw PS.

DETAILED DESCRIPTION

I. System Overview

Figure 1:
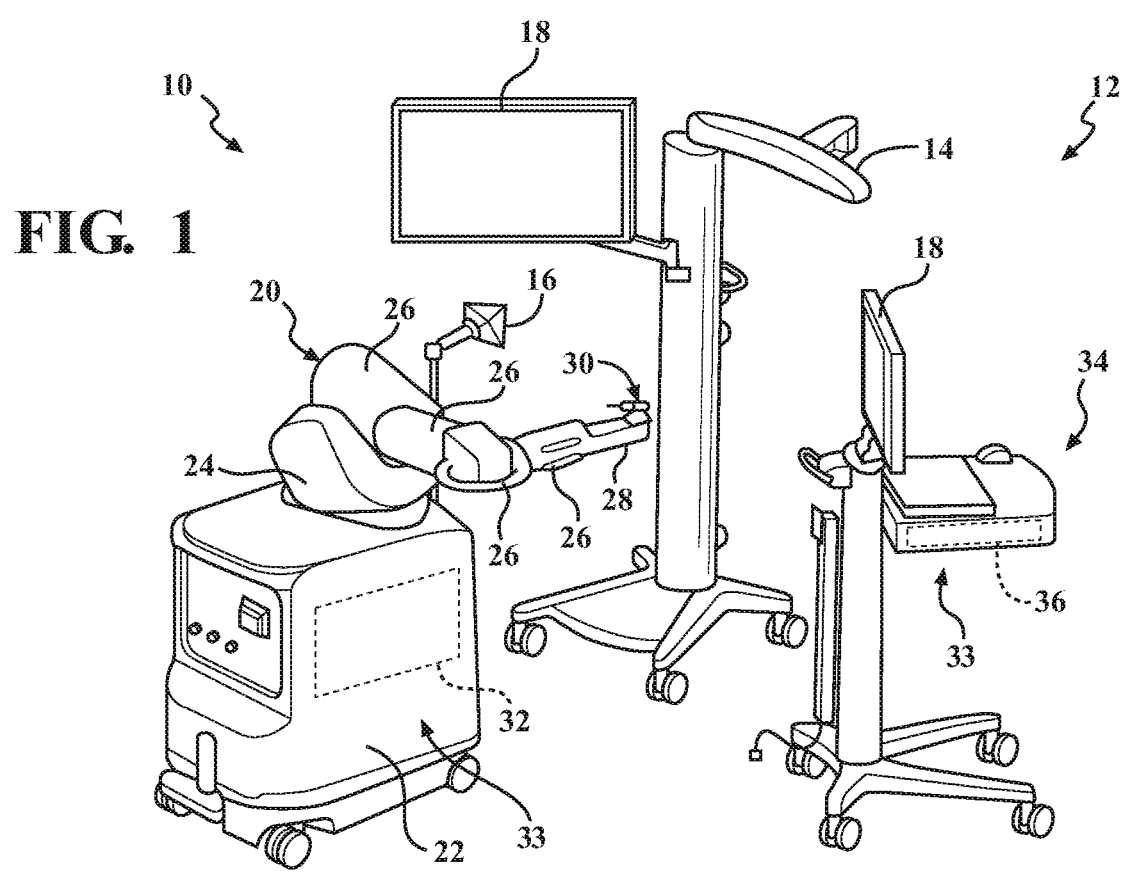
FIG. 1 is a perspective view of a robotic surgical system according to one example.
Figure 2:
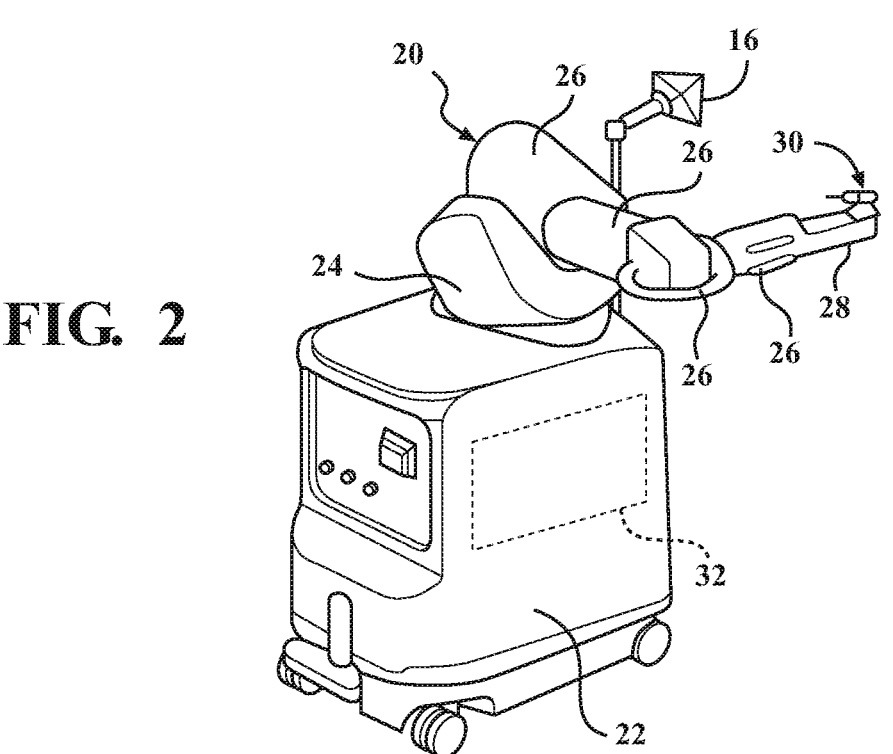
FIG. 2 is a perspective view of one example of a surgical robotic arm used with the robotic surgical system of FIG. 1.

Referring to FIGS. 1 and 2, a robotic surgical system 10 is shown which can be used for various surgical procedures, including, but not limited to, spine procedures, such as spine procedures in which pedicle screws, other screws, or other types of implants are placed in the spine. The robotic surgical system 10 comprises a navigation system 12 including a localizer 14 and a tracking device 16, one or more displays 18, and a robotic manipulator (e.g., a robotic arm 20 mounted to a base 22, a table, or the like). The robotic arm 20 includes a base link 24 rotatably coupled to the base 22 and a plurality of arm links 26 extending from the base link 24 to a distal end 28. The arm links 26 pivot/rotate about a plurality of joints in the robotic arm 20. A surgical tool for use in performing the spine procedure, for example, is shown generally at 30. The surgical tool 30 may be pivotally connected to the distal end 28 of the robotic arm 20. The arm links 26 can be serially mounted. Alternatively, the robotic arm 20 may include parallel arm linkages. Furthermore, any number of robotic arms 20 may be employed.

A robotic controller 32 is configured to provide control of the robotic arm 20 or guidance to the surgeon (referred to herein as "the operator") during manipulation of the surgical tool 30. In one instance, the robotic controller 32 is configured to control the robotic arm 20 (e.g., by controlling joint motors thereof) to provide haptic feedback to the operator via the robotic arm 20. This haptic feedback helps to constrain or inhibit the operator from manually moving the surgical tool 30 beyond predefined virtual boundaries associated with the surgical procedure. Such a haptic feedback system and associated haptic objects that define the virtual boundaries are described, for example, in U.S. Pat. No.

8,010,180 to Quaid et al., filed on Feb. 21, 2006, entitled "Haptic Guidance System And Method," and/or U.S. Patent Application Publication No. 2014/0180290 to Otto et al., filed on Dec. 21, 2012, entitled "Systems And Methods For Haptic Control Of A Surgical Tool," each of which is hereby incorporated by reference herein in its entirety. In one instance, the robotic surgical system 10 is the RIO™ Robotic Arm Interactive Orthopedic System manufactured by MAKO Surgical Corp. of Fort Lauderdale, FL, USA.

In some instances, the robotic arm 20 acts autonomously based on predefined tool paths and/or other predefined movements to perform the surgical procedure. Such movements may be defined during the surgical procedure and/or before the procedure. In further instances, a combination of manual and autonomous control is utilized. For example, a robotic surgical system that employs both a manual mode in which an operator applies force to the surgical tool 30 to cause movement of the robotic arm 20 and a semi-autonomous mode in which the operator holds a pendant to control the robotic arm 20 to autonomously follow a tool path is described in U.S. Pat. No. 9,566,122 to Bowling et al., filed on Jun. 4, 2015, and entitled "Robotic surgical system And Method For Transitioning Between Operating Modes," hereby incorporated by reference herein in its entirety.

The navigation system 12 is set up to track movement of various objects in the operating room with respect to a target coordinate system. Such objects include, for example, the surgical tool 30, the patient's anatomy of interest, e.g., one or more vertebra, and/or other objects. The navigation system 12 tracks these objects for purposes of displaying their relative positions and orientations in the target coordinate system to the operator and, in some cases, for purposes of controlling or constraining movement of the surgical tool 30 relative to virtual boundaries associated with the patient's anatomy and defined with respect to the target coordinate system (e.g., via coordinate system transformations well known in surgical navigation).

The surgical navigation system 12 includes a computer cart assembly 34 that houses a navigation controller 36. The navigation controller 36 and the robotic controller 32 collectively form a control system of the robotic surgical system 10. A navigation interface is in operative communication with the navigation controller 36. The navigation interface includes the displays 18 that are adjustably mounted to the computer cart assembly 34. Input devices such as a keyboard and mouse can be used to input information into the navigation controller 36 or otherwise select/control certain aspects of the navigation controller 36. Other input devices are contemplated including a touch screen (not shown) or voice-activation.

The localizer 14 communicates with the navigation controller 36. In the instance shown, the localizer 14 is an optical localizer and includes a camera unit (one example of a sensing device). The camera unit has an outer casing that houses one or more optical position sensors. In some instances, at least two optical sensors are employed, sometimes three or more. The optical sensors may be separate charge-coupled devices (CCD). The camera unit is mounted on an adjustable arm to position the optical sensors with a field of view of the below discussed tracking devices 16 that, ideally, is free from obstructions. In some instances, the camera unit is adjustable in at least one degree of freedom by rotating about a rotational joint. In other instances, the camera unit is adjustable about two or more degrees of freedom.

The localizer 14 includes a localizer controller (not shown) in communication with the optical sensors to receive signals from the optical sensors. The localizer controller communicates with the navigation controller 36 through either a wired or wireless connection (not shown). One such connection may be an IEEE 1394 interface, which is a serial bus interface standard for high-speed communications and isochronous real-time data transfer. The connection could also use a company specific protocol. In other instances, the optical sensors communicate directly with the navigation controller 36.

Position and orientation signals and/or data are transmitted to the navigation controller 36 for purposes of tracking the objects. The computer cart assembly 34, the displays 18, and the localizer 14 may be like those described in U.S. Pat. No. 7,725,162 to Malackowski, et al. issued on May 25, 2010, entitled "Surgery System," hereby incorporated by reference.

The robotic controller 32 and the navigation controller 36 may each, or collectively, comprise one or more personal computers or laptop computers, memory suitable for storage of data and computer-readable instructions, such as local memory, external memory, cloud-based memory, random access memory (RAM), non-volatile RAM (NVRAM), flash memory, or any other suitable form of memory. The robotic controller 32 and the navigation controller 36 may each, or collectively, comprise one or more processors, such as microprocessors, for processing instructions or for processing algorithms stored in memory to carry out the functions described herein. The processors can be any type of processor, microprocessor or multi-processor system. Additionally or alternatively, the robotic controller 32 and the navigation controller 36 may each, or collectively, comprise one or more microcontrollers, field programmable gate arrays, systems on a chip, discrete circuitry, and/or other suitable hardware, software, or firmware that is capable of carrying out the functions described herein. The robotic controller 32 and the navigation controller 36 may be carried by the robotic manipulator, the computer cart assembly 34, and/or may be mounted to any other suitable location. The robotic controller 32 and/or the navigation controller 36 is loaded with software as described below. The software converts the signals received from the localizer 14 into data representative of the position and orientation of the objects being tracked.

The robotic surgical system 10 may include any number of controllers to control components of the robotic surgical system 10 in addition to the robotic controller 32. For example, the robotic surgical system 10 may include a tool controller configured to control the surgical tool 30. As another example, the robotic surgical system 10 may include a haptic device controller configured to control a haptic device of the robotic surgical system 10 (described in greater detail below). The controllers of the robotic surgical system 10 may be configured to carry out the functions of a surgical procedure individually or in combination. For example, the robotic controller 32, the navigation controller 36, the localizer controller, the tool controller, and the haptic device controller may operate in combination to provide haptic feedback to the operator via the haptic device of the robotic surgical system 10. As another example, the robotic controller 32 may operate individually to control the robotic arm 20. As such, to capture these various configurations, this description hereinafter may refer to "one or more controllers 33" as also indicated in FIG. 1. It should be understood "the one or more controllers 33" includes any individual controller or any combination of controllers suitable for performing the referenced function. The collective one or more controllers may also be considered a control system.

Furthermore, any of the steps within this specification, which are executed by any of the one or more controllers 33 described herein, are operable according to the control algorithms described herein, which may be implemented according to a finite sequence of steps for solving the tasks described herein.

Figure 3:
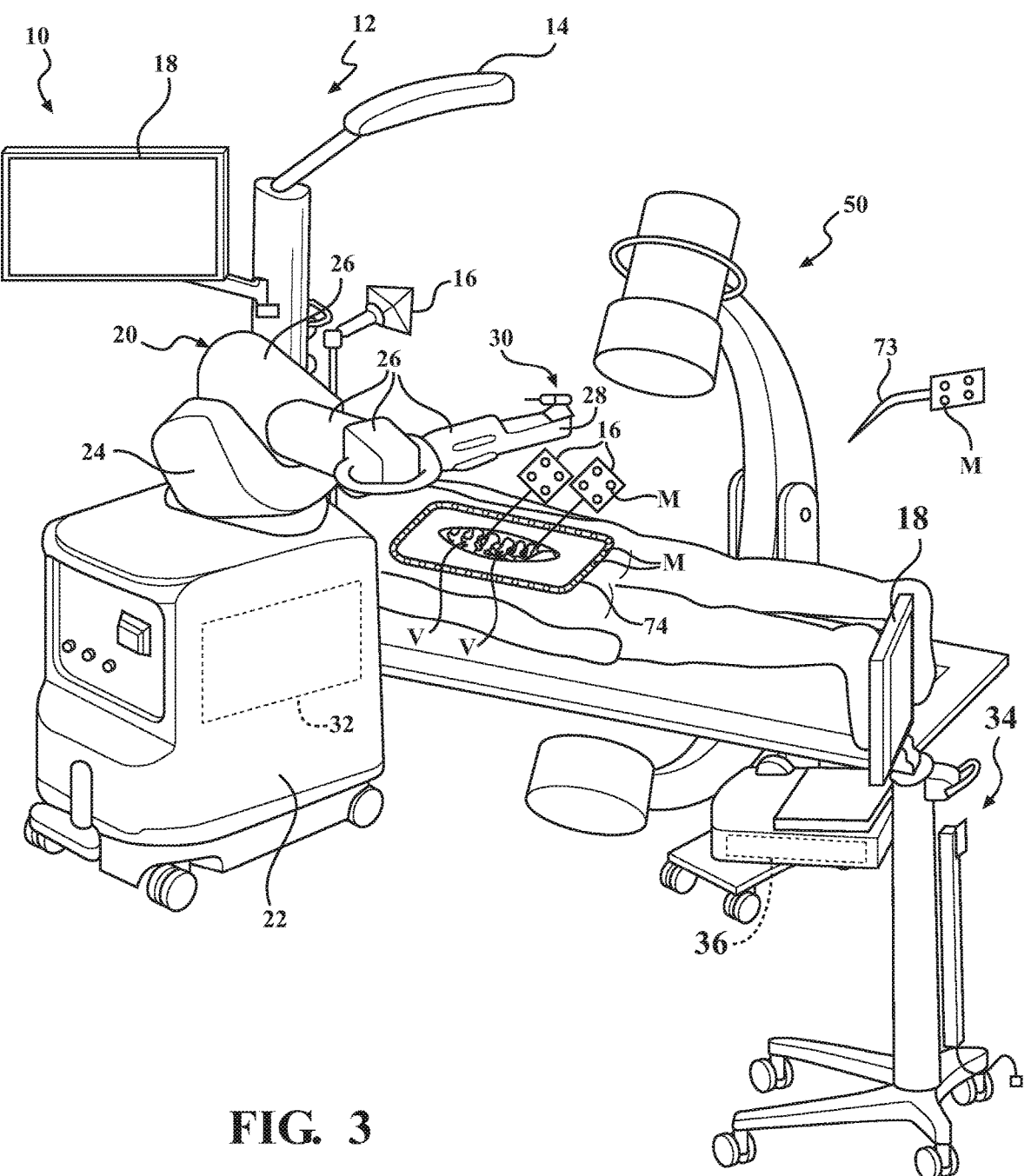
FIG. 3 is a perspective view of one example of the robotic surgical system being used in combination with an imaging device to perform a spine procedure.

Referring to FIG. 3, navigation system 12 includes a plurality of tracking devices 16, also referred to herein as trackers. In the illustrated instance, trackers 16 are coupled to separate vertebra of the patient. In some cases, the trackers 16 are firmly affixed to sections of bone via bone screws, bone pins, or the like. In other cases, clamps on the spinous process or other portion of the spine may be used to attach the trackers 16. In further instances, the trackers 16 could be mounted to other tissue types or parts of the anatomy. The position of the trackers 16 relative to the anatomy to which they are attached can be determined by registration techniques, such as point-based registration in which a digitizing probe 73 (e.g., navigation pointer with its own markers) is used to touch off on bony landmarks on the bone or to touch on several points on the bone for surface-based registration. Conventional registration techniques can be employed to correlate the pose of the trackers 16 to the patient's anatomy, e.g., the vertebra V being treated.

Other types of registration are also possible such as using trackers 16 with mechanical clamps that attach to the spinous process of the vertebra V and that have tactile sensors (not shown) to determine a shape of the spinous process to which the clamp is attached. The shape of the spinous process can then be matched to the 3-D model of the spinous process for registration. A known relationship between the tactile sensors and the three or more markers on the tracking device 16 is pre-loaded into the navigation controller 36. Based on this known relationship, the positions of the markers relative to the patient's anatomy can be determined.

A base tracker 16 can be coupled to the base 22 to track the pose of the surgical tool 30. In other instances, a separate tracker 16 could be fixed to the surgical tool 30, e.g., integrated into the surgical tool 30 during manufacture or may be separately mounted to the surgical tool 30 in preparation for the surgical procedures. In any case, a working end of the surgical tool 30 is being tracked by virtue of the base tracker 16 or other tracker. The working end may be a distal end of an accessory of the surgical tool 30. Such accessories may comprise a drill, a bur, a saw, an electrical ablation device, a screwdriver, a tap, a surgical knife, a Jamshidi needle, or the like.

In the illustrated instance, the trackers 16 are passive trackers. In this instance, each tracker 16 has at least three passive tracking elements or markers M for reflecting light from the localizer 14 back to the optical sensors. In other instances, the trackers 16 are active trackers and may have light emitting diodes or LEDs transmitting light, such as infrared light to the optical sensors. Based on the received optical signals, navigation controller 36 generates data indicating the relative positions and orientations of the trackers 16 relative to the localizer 14 using conventional triangulation techniques. In some cases, more or fewer markers may be employed. For instance, in cases in which the object being tracked is rotatable about a line, two markers can be used to determine an orientation of the line by measuring positions of the markers at various locations about the line. It should be appreciated that the localizer 14 and trackers 16, although described above as utilizing optical tracking techniques, could alternatively, or additionally, utilize other tracking modalities to track the objects, such as electromagnetic tracking, ultrasound, radio frequency tracking, inertial tracking, combinations thereof, and the like.

It may also be desired to track the patient's skin surface to ensure that the surgical tool 30 does not inadvertently contact or penetrate the patient's skin outside of any desired incision boundaries. For this purpose, skin attached markers M, such as active or passive markers with adhesive backing may be attached to the patient's skin to define a boundary associated with the patient's skin. An array of such markers M could be provided in a peripheral ring 74 (circular, rectangular, etc.), such that the surgical procedure continues inside the ring 74 without substantially disturbing the ring 74 (i.e., the ring is placed on the patient's skin about the incision and vertebrae of interest). One suitable skin marker array is the SpineMask® tracker manufactured by Stryker Leibinger GmbH & Co. KG, Botzinger Straße 41, D-79111 Freiburg, Germany. Sec also U.S. Patent Application Publication No. 2015/0327948 to Schoepp et al., entitled "Navigation System For And Method Of Tracking The Position Of A Work Target," filed on May 13, 2015, hereby incorporated herein by reference in its entirety. Other suitable skin trackers are also contemplated. The digitizing probe could also be used to map the skin surface and/or incision as well. However, once mapped, any movement of the skin would not be detected without further digitizing, whereas the attached tracker array can detect movement of the patient's skin.

Prior to the start of the surgical procedure, additional data are loaded into the navigation controller 36. Based on the position and orientation of the trackers 16 and the previously loaded data, navigation controller 36 determines the position of the working end of the surgical tool 30 and the orientation of the surgical tool 30 relative to the tissue against which the working end is to be applied. The additional data may comprise calibration data, such as geometric data relating positions and/or orientations of the trackers 16 or markers M thereof to the working end of the surgical tool 30. This calibration data may also be determined pre-operatively or intra-operatively, such as by using a calibration probe or calibration divot on a tracker 16 of known geometry to determine a position of the working end of the surgical tool 30, e.g., relative to its own tracker or to the base tracker 16. The additional data may comprise registration data, such as transformation data associating the trackers 16 to the patient's anatomy or 3-D models thereof. In some instances, navigation controller 36 forwards these data to the robotic controller 32. The robotic controller 32 can then use the data to control the robotic arm 20 as described in U.S. Pat. Nos. 8,010,180, 9,566,122, both of which were previously incorporated by reference herein.

The navigation controller 36 also generates image signals that indicate the relative position of the working end of the surgical tool 30 to the tissue of interest. These image signals are applied to the displays 18. Displays 18, based on these signals, generate images that allow the operator and staff to view the relative position of the surgical tool 30 to the surgical site. The displays 18 as discussed above, may include a touch screen or other input/output device that allows entry of commands.

In the instance shown, using the navigation system 12, the pose of the surgical tool 30 can be determined by tracking the location of the base 22 via the base tracker 16 and calculating the pose of the surgical tool 30 based on joint encoder data from the joints of the robotic arm 20 and a known geometric relationship between the surgical tool 30 and the robotic arm 20. Ultimately, the localizer 14 and the tracking devices 16 enable the determination of the pose of the surgical tool 30 and the patient's anatomy so the navigation system 12 knows the relative relationship between the surgical tool 30 and the patient's anatomy. One such navigation system is shown in U.S. Pat. No. 9,008,757 to Wu, filed on Sep. 24, 2013, entitled "Navigation System Including Optical And Non-Optical Sensors," hereby incorporated herein by reference.

In operation, for certain surgical tasks, the operator manually manipulates (e.g., moves or causes the movement of) the robotic arm 20 to manipulate the surgical tool 30 to perform the surgical procedure on the patient, such as drilling, cutting, sawing, reaming, implant installation, and the like. As the operator manipulates the surgical tool 30, the navigation system 12 tracks the location of the surgical tool 30 and/or the robotic arm 20 and provides haptic feedback (e.g., force feedback) to the operator to limit the operator's ability to move (or cause movement of) the surgical tool 30 beyond one or more predefined virtual boundaries that are registered (or mapped) to the patient's anatomy, which results in highly accurate and repeatable drilling, cutting, sawing, reaming, and/or implant placement.

In one instance, the robotic arm 20 operates in a passive manner and provides haptic feedback when the operator attempts to move the surgical tool 30 beyond the virtual boundary. The haptic feedback is generated by one or more actuators (e.g., joint motors) in the robotic arm 20 and transmitted to the operator via a flexible transmission, such as a cable drive transmission. When the robotic arm 20 is not providing haptic feedback, the robotic arm 20 is freely moveable by the operator. In other instances, like that shown in U.S. Pat. No. 9,566,122, previously incorporated herein by reference, the robotic arm 20 is manipulated by the operator in a similar manner, but the robotic arm 20 operates in an active manner. For instance, the operator applies force to the surgical tool 30, which is measured by a force/torque sensor, and the robotic arm 20 emulates the operator's desired movement based on measurements from the force/torque sensor. For other surgical tasks, the robotic arm 20 operates autonomously.

Figures 4, 5:
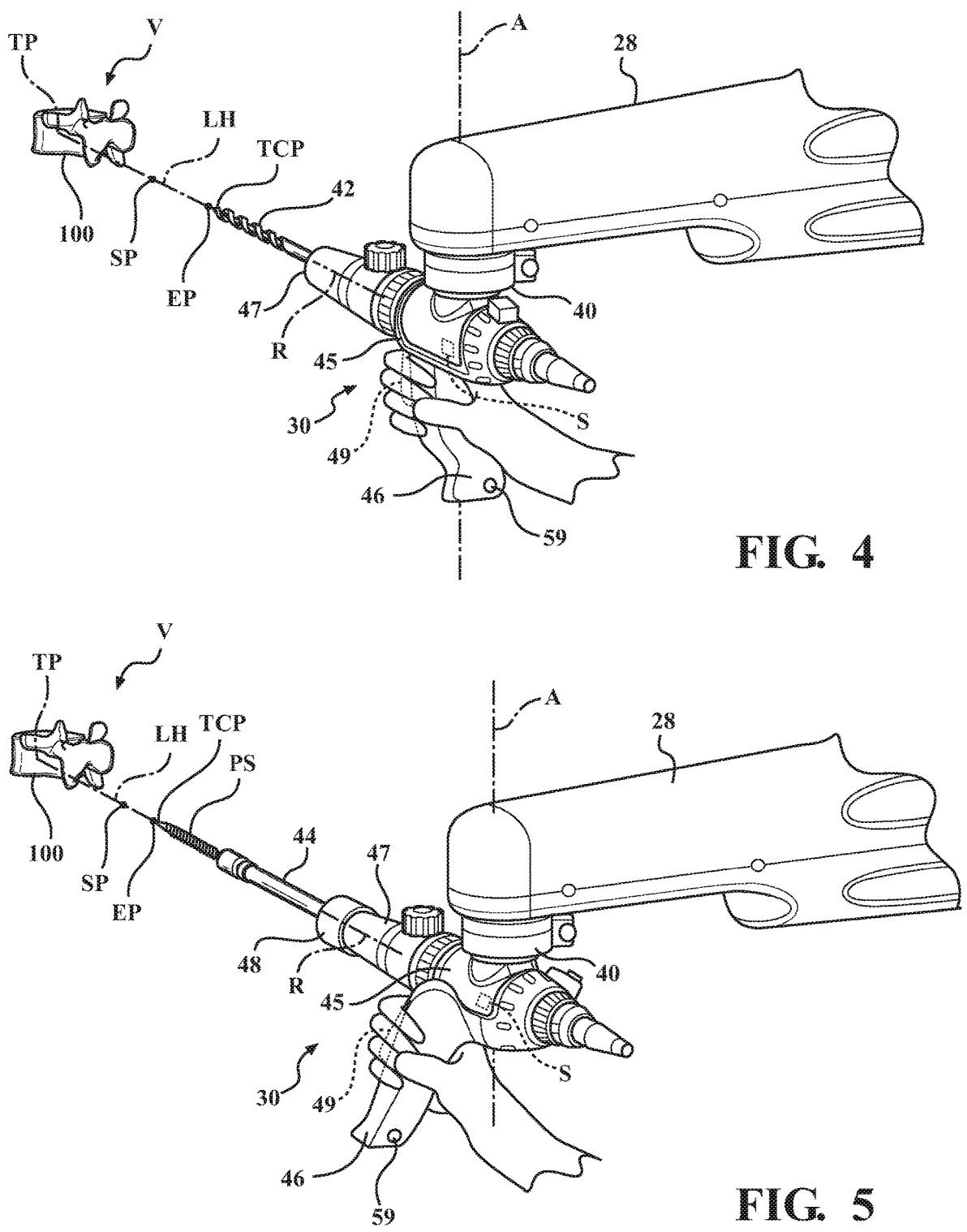
FIG. 4 is a partial perspective view of one example of a surgical tool coupled to a robotic arm, with the surgical tool including a housing coupled to a drill.
FIG. 5 is a partial perspective view of the robotic arm coupled to the surgical tool coupled to a driver and screw.

Turning to FIGS. 4 and 5, one example of the surgical tool 30 is shown coupled to the distal end 28 of the robotic arm 20. More specifically, a coupling 40 is provided between the surgical tool 30 and the distal end 28 of the robotic arm 20 to allow rotation of the surgical tool 30 relative to the distal end 28 about axis A. In FIG. 4, the surgical tool 30 comprises a drill 42 for drilling a pilot hole for a pedicle screw, other screw, or other type of implant. The drill 42 is arranged to rotate about a rotational axis R. In FIG. 5, the surgical tool 30 comprises a driver 44 (e.g., a screwdriver) arranged along the rotational axis R to rotate about the rotational axis R for inserting a pedicle screw PS or other implant. The surgical tool 30 comprises a housing 45. A drive system (e.g., motor) is located in the housing 45 to drive the drill 42, driver 44, or another accessory. The drive system may be variable speed.

The housing 45 further comprises a collet 47 or other type of coupler for releasably attaching the drill 42, driver 44, or other accessory to the drive system. In some cases, a speed reducer 48 (see FIG. 5) may be releasably attached to the collet 47 to be used for certain accessories. The speed reducer 48 comprises a transmission or gear arrangement that causes the rotational rate of the accessory to be reduced as compared to being connected directly to the drive system. This is useful in cases where slower rotational rates are desired.

Figure 6:
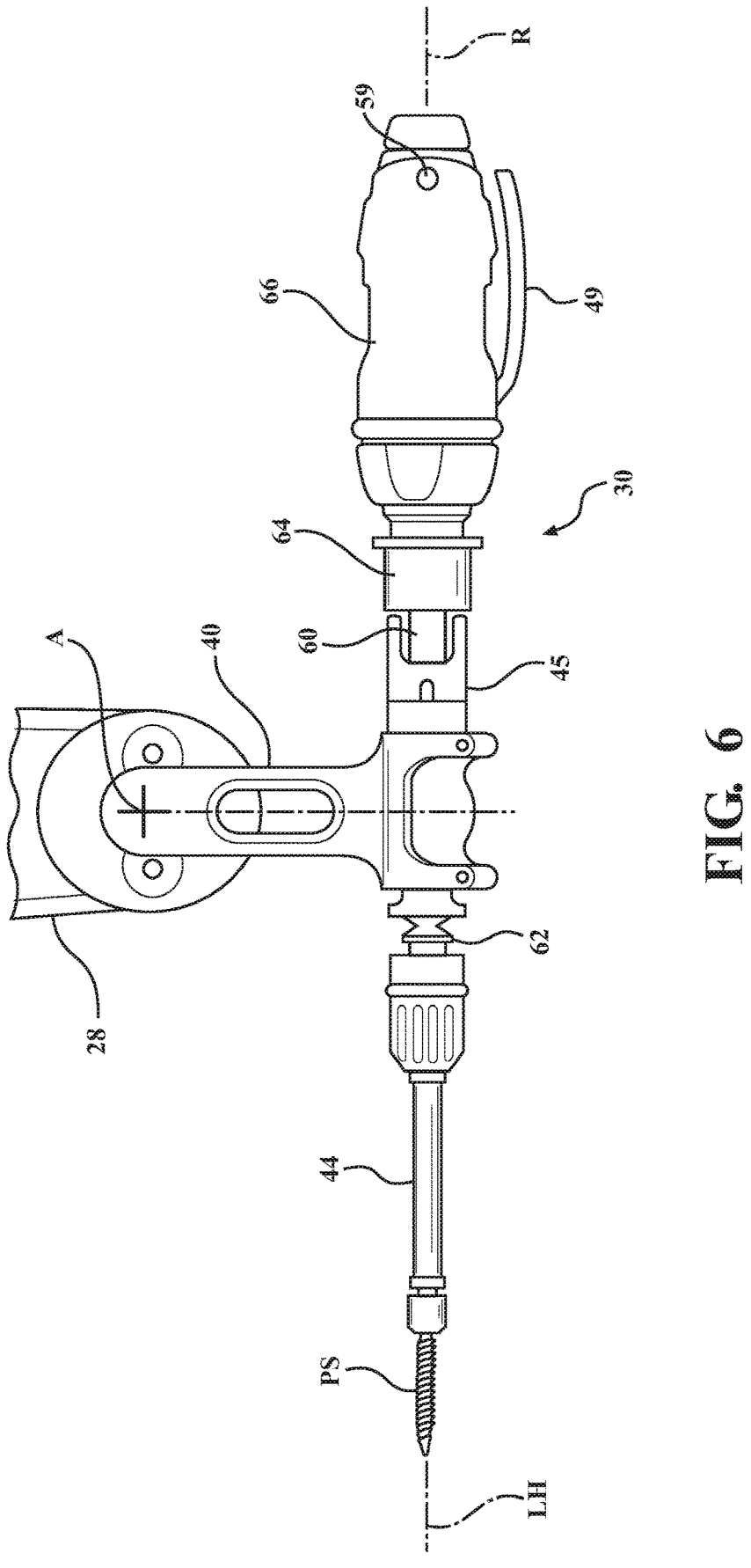
FIG. 6 is an elevational view of an alternative surgical tool.

In another instance shown in FIG. 6, one end of the coupling 40 supports the surgical tool 30 for rotation about the axis A. Another end of the coupling 40 supports the housing 45. The housing 45 may be fixed to the coupling 40 or may be supported for rotation within the coupling 40 about the rotational axis R. In other words, the housing 45 may be able to passively rotate within the coupling 40. At the same time, however, the coupling 40 limits axial movement of the housing 45 along the rotational axis R relative to the coupling 40 so that positioning of the housing 45 can be precisely controlled. A tracker (not shown) could be mounted to the housing 45 to track the position and/or orientation of the housing 45 and thereby track the rotational axis R and/or a distal end of the accessory attached to the housing 45. A rotating shaft 60 is rotatably supported in the housing 45. The rotating shaft 60 has a distal interface/collet 62 that couples to the accessory (e.g., driver 44 as shown) and a proximal interface/collet 64 that couples to a power source, such as a source of torque, e.g., a motor, rotatable handle for manual rotation, and the like. For example, the driver 44 is shown coupled to the distal interface 62/rotating shaft 60.

The robotic surgical system 10 may include various components for controlling the drill 42 and/or driver 44. For example, in FIGS. 4 and 5, the surgical tool 30 includes a handle 46 that depends from the housing 45. The handle 46 may include a grip for being grasped by the operator to manipulate the surgical tool 30 and/or the robotic arm 20 during the surgical procedure. A trigger 49 may also be present to control a speed of the drill 42 and/or driver 44, to initiate movement of the robotic arm 20, to align the rotational axis R with a desired trajectory, or the like. The trigger 49 may communicate signals to the robotic controller 32 and/or the tool controller to control the robotic arm 20 and/or the surgical tool 30.

In the instance of FIG. 6, the surgical tool 30 includes a handpiece 66 with an internal motor for controlling the surgical tool 30 and the drill 42. As shown, the handpiece 66 is coupled to the proximal interface 64 so that the operator is able to grip the handpiece 66, trigger operation of the motor, and cause the motor to transmit torque through the rotating shaft 60 to the driver 44 and ultimately to the pedicle screw PS.

Pre-operative imaging and/or intra-operative imaging may be employed to visualize the patient's anatomy that requires treatment-such as the patient's spine. The operator can plan where to place the pedicle screws PS with respect to the images and/or with respect to a 3-D model created from the images. Planning includes determining a pose of each pedicle screw PS with respect to the particular vertebra V in which they are being placed, e.g., by identifying the desired pose in the images and/or the 3-D model. This may include creating or positioning a separate 3-D model of the pedicle screw PS with respect to the 3-D model of the patient's anatomy. Once the plan is set, then the plan is transferred to the robotic surgical system 10 for execution.

The robotic surgical system 10 may be used in concert with an imaging device 50 (e.g., a C-arm as shown in FIG. 3) to take the intra-operative images of the patient's anatomy in addition to, or alternatively to, any pre-operative images, e.g., X-rays, CT scans, or MRI images taken before surgery. The intra-operative images from the imaging device 50 can help to determine the actual position of the drill 42 or driver 44 relative to the desired orientation of the pedicle screws PS being placed in the patient's spine. Separate tracking devices 16 can be employed on each vertebra V to separately track each vertebra V and the corresponding pose of the drill 42 and/or driver 44 relative to the separate vertebra V when placing the pedicle screws PS or other implants into the vertebra V.

The robotic surgical system 10 evaluates the desired pose of the pedicle screws PS and creates virtual boundaries (e.g., haptic objects), pre-defined tool paths, and/or other autonomous movement instructions, that correspond to the desired pose of the pedicle screws PS to control movement of the robotic arm 20 so that the drill 42 and driver 44 of the surgical tool 30 are controlled in a manner that ultimately places the pedicle screws PS according to the operator's plan. This may comprise, for example, ensuring during the surgical procedure that a trajectory of the surgical tool 30 is aligned with the desired pose of the pedicle screws PS, e.g., aligning the rotational axis R with the desired pose of the pedicle screw PS.

In other instances, the operator may intra-operatively plan the desired trajectory and/or screw placement. For example, the operator can position the drill 42 at a desired entry point relative to the anatomy of interest, e.g., a vertebra V, and orient the drill 42 until the display 18 shows that the trajectory of the rotational axis R is in a desired orientation. Once the operator is satisfied with the trajectory, the operator can provide input (e.g., touchscreen, button, foot pedal, etc.) to the control system to set this trajectory as the desired trajectory to be maintained during the procedure. The haptic object created for constraining movement of the surgical tool 30 to maintain the rotational axis R to stay along the desired trajectory may be a line haptic object LH, such as that shown in FIG. 4. The line haptic object LH may have a starting point SP, as described further below, a target point TP, which defines a desired depth of the drill 42, pedicle screw PS, etc., and an exit point EP. Other haptic object shapes, sizes, etc. are also contemplated.

Figures 7, 8:
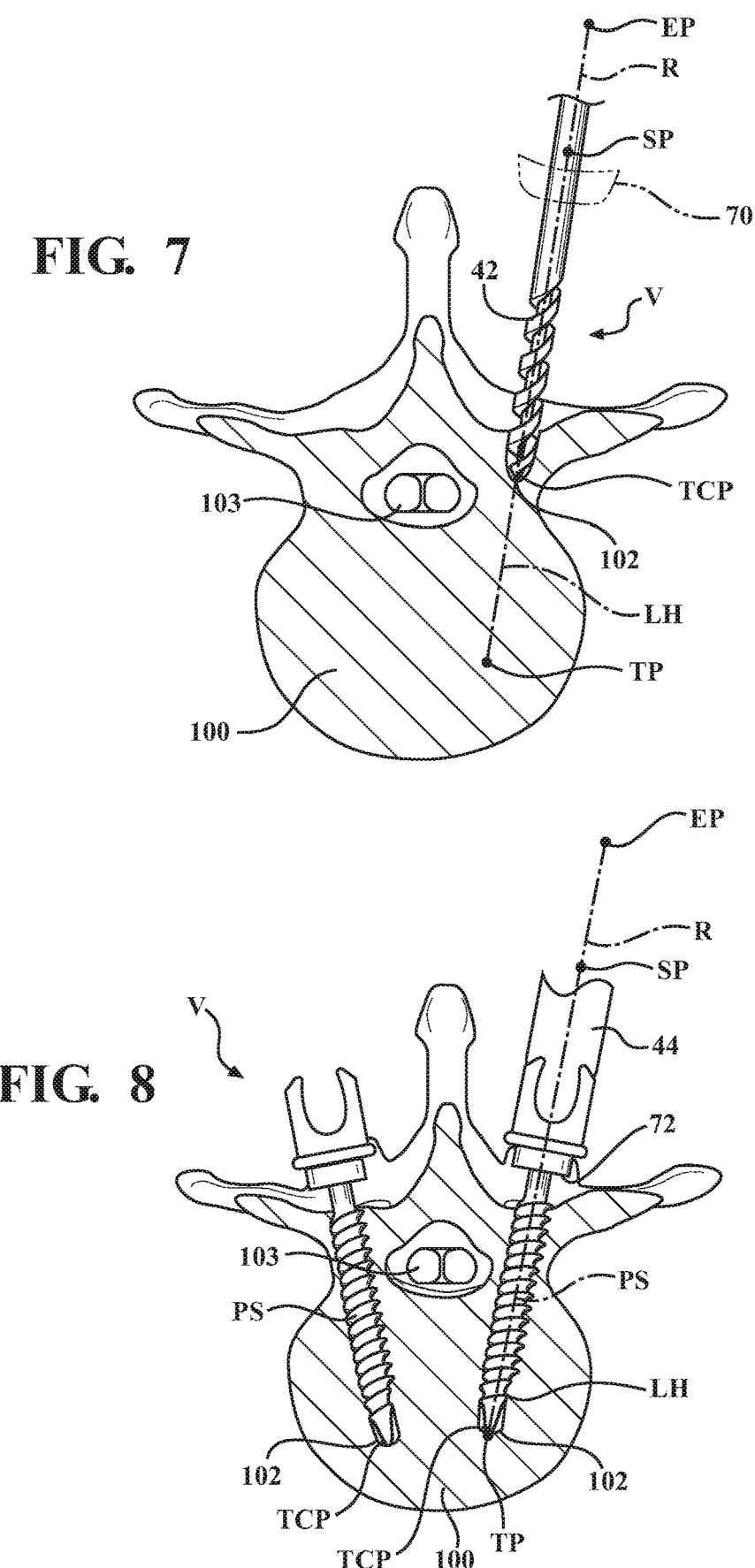
FIG. 7 is an illustration of drilling a pilot hole in a pedicle according to one example.
FIG. 8 is an illustration of pedicle screws into the vertebra according to one example.

Referring to FIGS. 7 and 8, one of the vertebra V is shown. During the surgical procedure, such as a spinal fusion surgery, an operator may insert one or more pedicle screws PS through pedicle regions into a vertebral body 100 of vertebra V. Prior to inserting the pedicle screws PS, the operator may employ the drill 42 to cut pilot holes 102 in the vertebral body 100. In an alternative instance, pilot holes may be excluded, such as where a self-drilling, self-tapping bone screw is employed. See, for example, the teachings in U.S. Pat. No. 7,637,929 to Stefan Auth, issued on Dec. 29, 2009, entitled "Self-drilling bone screw," which is hereby incorporated by reference herein in its entirety.

In one instance, before drilling commences, the robotic surgical system 10 controls movement of the surgical tool 30 to place the rotational axis R along the desired trajectory by autonomously aligning the rotational axis R of the surgical tool 30 with the desired trajectory, which coincides with the desired orientation of the pilot holes 102. In this case, the robotic arm 20 may autonomously position the drill 42 along the desired trajectory but spaced above the vertebral body 100 (as shown in FIG. 4) so that the drill 42 has not yet contacted the vertebral body 100. Such autonomous positioning may be initiated by the operator pulling the trigger on the surgical tool 30, or otherwise providing input to the control system to start the movement. In some cases, a tool center point (TCP) of the surgical tool 30 is first brought to within a predefined distance of the starting point SP of the line haptic object LH that provides the desired trajectory (such as within a predefined starting sphere). Once the TCP (e.g., bur centroid, drill tip center, etc.) is within the pre-defined distance of the starting point SP, then pulling the trigger (or alternatively pressing a foot pedal or actuating some other input) causes the robotic arm 20 to autonomously align and position the surgical tool 30 on the desired trajectory. See, for example, the teachings in U.S. Patent Application Publication No. 2014/0180290 to Otto et al., filed on Dec. 21, 2012, entitled "Systems And Methods For Haptic Control Of A Surgical Tool," which is hereby incorporated by reference herein in its entirety. The robotic arm 20 may be programmed to move the surgical tool 30 to a distance from the patient based on pre-surgical planning or may move the TCP to the closest point on the trajectory. Once the surgical tool 30 is in the desired pose, the robotic surgical system 10 may effectively hold the rotational axis R of the surgical tool 30 on the desired trajectory by tracking movement of the patient and autonomously adjusting the robotic arm 20 as needed to keep the rotational axis R on the desired trajectory, i.e., aligned with the line haptic object LH.

While the robotic surgical system 10 holds the surgical tool 30 on the desired trajectory, the operator may then manually manipulate the surgical tool 30 to move (or cause movement of) the drill 42 along the line haptic object LH toward the vertebral body 100 to drill the pilot holes 102. In some cases, such as when using a passive robotic arm 20, the robotic surgical system 10 constrains the operator's movement of the surgical tool 30 to stay along the desired trajectory by providing haptic feedback to the operator should the operator attempt to move the surgical tool 30 in a manner that deviates from the line haptic object LH and the desired trajectory. If the operator desires to return the robotic arm 20 to a free mode, for unconstrained movement of the surgical tool 30, the operator can pull the surgical tool 30 back along the line haptic object LH, away from the patient, until the exit point EP is reached.

The operator then drills the pilot holes 102 to desired depths. Drilling speed can be controlled by the operator via the trigger 49 or can be controlled automatically based on the location of the drill 42 relative to the patient's anatomy. For instance, a rotational rate of the drill 42 may be set high during initial drilling into the vertebral body V but may be slowed during further drilling into the vertebral body V and set even slower during final drilling to the final depth. The control system can also monitor contact/contact force during line haptic guiding via one or more sensors S (e.g., one or more force sensors, force/torque sensors, torque sensors, pressure sensors, optical sensors, or the like) that communicates with the robotic controller 32. If no significant contact/contact force is detected, which means the surgical tool 30 is passing through soft tissue, the control system avoids activating the motor of the surgical tool 30 or other power source (e.g., RF energy, ultrasonic motor, etc.). When contact with bone is detected (e.g., optically, sensed force is above a predefined threshold, etc.), the control system can activate the motor or other power source. Operators can also passively feel the contact/contact force and trigger a switch to activate the power source.

The virtual boundaries (e.g., haptic objects) used to constrain the operator's movement along the desired trajectory may also indicate, via haptic feedback, when the operator has reached the desired depth of the pilot holes 102, e.g., reached the target point TP. Separate virtual boundaries could also be used to set the desired depths. In other cases, the robotic surgical system 10 may autonomously drill the pilot holes 102 to the desired depths. In further cases, the robotic surgical system 10 may initially drill autonomously, but then final drilling may be done manually, or vice versa. Once the pilot holes 102 are created, the pedicle screws PS can then be placed using the driver 44. In some instances, pilot holes 102 may be unnecessary and the pedicle screws PS can be placed over guide wires placed by the robotic surgical system 10 or without any guidance. Pilot holes may be unnecessary, such as where a self-drilling, self-tapping bone screw is employed. See, for example, the teachings in U.S. Pat. No. 7,637,929 to Stefan Auth, issued on Dec. 29, 2009, entitled "Self-drilling bone screw," which is hereby incorporated by reference herein in its entirety.

One advantage of using the navigation system 12 to continuously track each vertebra V separately and to track movement of the drill 42 is that the pedicle screws PS may be inserted in close proximity to spinal cord 103, and thus, the placement of pedicle screws PS and their corresponding pilot holes 102 must be precisely aligned so as to avoid interacting with or damaging spinal cord 103. If an operator drills the pilot holes 102 at an improper angle and/or too deeply, pedicle screws PS or the drill 42 used to drill pilot holes 102 may damage the spinal cord 103. As a result, by using the navigation system 12 to track a pose of the drill 42 and/or the driver 44 relative to the patient's anatomy and specifically the anatomy as outlined in the preoperative images and/or the intraoperative images, the spinal cord 103 can be avoided.

Once drilling is complete, the drill 42 is removed from the vertebral body 100 and is disconnected from the drive system via the collet 47. The driver 44 is then coupled to the drive system (with or without the speed reducer 48).

The pedicle screws PS may be inserted with the assistance of the robotic surgical system 10. In one instance, the robotic controller 32 autonomously controls the insertion of the pedicle screws PS such that the rotational rate about the rotational axis R and the rate of advancement along the planned trajectory are proportional to a thread geometry of the pedicle screw. The robotic controller 32 may autonomously control insertion of the pedicle screws PS using a variety of methods.

For example, the pedicle screw PS may be inserted at a constant rotational rate or a constant advancement rate that may be pre-operatively stored in a memory of the robotic surgical system 10. In such an instance, the advancement rate and/or rotational rate may be stored in a memory of the robotic surgical system 10 prior to the procedure. The advancement rate and/or the rotational rate may also be entered and stored in a memory of the robotic surgical system during the procedure by the operator.

In another example, the robotic controller 32 may follow a predetermined profile for the rotational rate or advancement rate. The predetermined profile for the rotational rate or advancement rate may be based on any suitable variable, such as time or a location of the pedicle screw PS. For instance, referring to FIG. 9, insertion of the pedicle screw PS may be controlled autonomously based on the location of the driver 44 and/or pedicle screw PS relative to the patient's anatomy. In such an instance, a rotational rate of the driver 44 may be set high during initial installation into the vertebral body V but may be slowed during further installation into the vertebral body V and set even slower during final implanting to the final depth.

Figure 9:
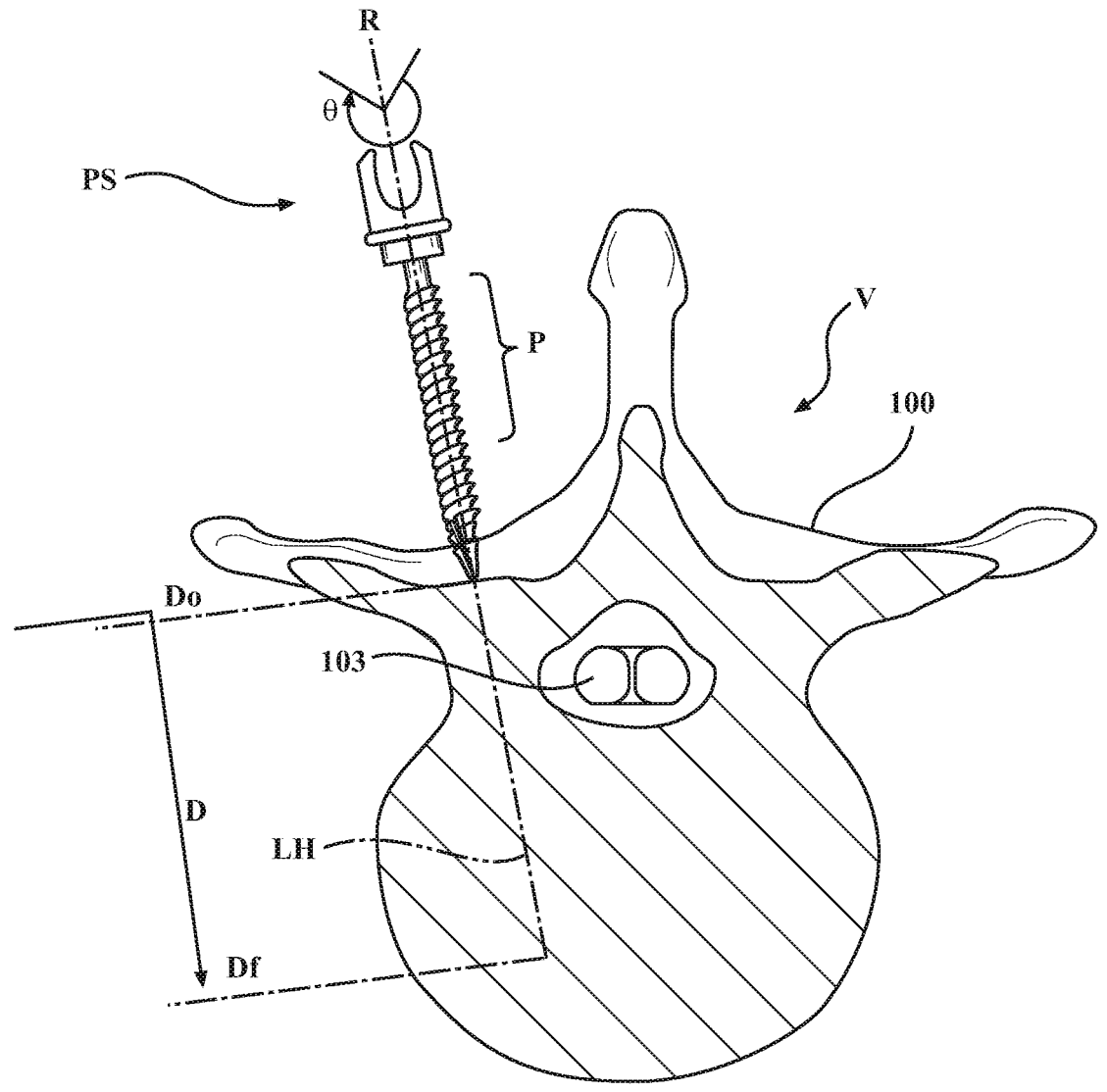
FIG. 9 is an illustration of a pedicle screw disposed along a line haptic.

FIG. 9 illustrates a home position of a pedicle screw PS while the robotic controller 32 autonomously controls the surgical tool 30. As shown, the pedicle screw PS is adjacent to the target site, in this case, shown as vertebra V, with the planned trajectory designated by a linear haptic object LH. The threaded interface between the pedicle screw PS and the vertebral body 100 risks damage to the bone, the screw PS, the driver 44 or surgical tool 30 if the pedicle screw PS is inserted incorrectly. The bone is likely the weakest material and thus most likely to suffer damage if the screw is inserted incorrectly. Improper insertion may occur, for example, when the pedicle screw PS advances linearly along the trajectory LH with insufficient rotation about the rotational axis R. This may cause bone material to shear off adjacent to the threads and be forced down into the bone. In another example, improper insertion may occur when, for example, the pedicle screw PS is rotated about the rotational axis R with insufficient advancement along the trajectory LH, causing bone material to shear off adjacent to the threads and be forced back along the threads, in effect over drilling the hole. In either example, the result of the improper insertion is to decrease the strength and amount of bone material to secure the pedicle screw PS in the bone.

FIG. 9 also illustrates the use of position control to insert the pedicle screw PS while the robotic controller 32 autonomously controls the surgical tool 30. Position control for inserting a screw ensures that the proper depth position and angular or rotational position are maintained throughout the operation. The vertebral body 100 may be prepared with a pilot hole, as shown in the instances above, or the operation may employ a self-drilling and self-tapping screw so that no pilot hole is required. The starting point Do of the pedicle screw PS is adjacent to the vertebral body 100, that is, prior to any part of the screw penetrating into the vertebral body 100. In an alternative, the starting point Do may be spaced away from the vertebral body 100 by a distance as a safety margin to ensure proper position control throughout the operation. The depth of insertion D advances along the trajectory LH to a final depth Df as the planned depth to complete installation of the pedicle screw PS in the vertebral body 100.

The robotic controller 32 is configured to autonomously control the insertion of the pedicle screw PS so that the rotational rate and the rate of advancement along the trajectory LH are proportional to the thread geometry of the pedicle screw PS. Each pedicle screw PS has a known thread geometry stored in a memory of the robotic surgical system 10. For example, for each pedicle screw PS, the thread geometry may include any one or more of pedicle screw PS length, thread diameter, depth of thread, head size, and thread pitch P, which is defined as the number of threads per unit length. In a specific example, the pedicle screw PS illustrated in FIG. 11A may have a thread pitch of 12 threads per inch. Other exemplary pedicle screws PS may have 8, 10, 14, 16 or other number of threads per inch. Having a defined relationship between the robotic arm 20 and the pedicle screw PS, and a known geometry of the pedicle screw PS stored in a memory of the robotic surgical system 10, the robotic controller 32 is configured to ensure a proper rotational rate and advancement speed for inserting a pedicle screw PS having a particular thread pitch.

The thread geometry of the pedicle screw PS can be stored in a memory of the robotic surgical system 10 pre-operatively or intraoperatively. In one example, the pedicle screw PS is chosen as part of a surgical plan, and the corresponding thread geometry of the pedicle screw PS is associated with the pedicle screw PS and inputted into the plan. Once the plan is loaded for intraoperative surgery, the robotic surgical system 10 will have the known the thread geometry stored in a memory for immediate access. In another example, the operator can manually select different pedicle screws PS, or can manually input the thread geometry using a GUI affiliated with operation of the robotic surgical system 10. The inputted thread geometry may be obtained from a database stored in a memory, or can be derived from the operator obtaining such information from offline specifications associated with a chosen pedicle screw PS. In any of these examples, the thread geometry can be stored in a memory after the operator input using GUI such that the robotic surgical system 10 can subsequently carry out the control techniques described herein with the inputted thread geometry. In yet another example, a measurement tool directly or wirelessly connected to the robotic surgical system 10 may be utilized to scan or measure any intended pedicle screw PS to extract the thread geometry and transmit the measured thread geometry to the robotic surgical system 10 memory. Once the thread geometry of the pedicle screw PS is stored in a memory of the robotic surgical system 10, the pedicle screw PS may be presented virtually within the navigation system 12.

The relationship between the pedicle screw thread pitch, the angular, or rotational, position and the depth of insertion, or advancement along the trajectory, is governed by the equation $\theta = D*(Pitch/2\pi)$, where $\theta$ is the angular position, D is the depth of insertion in unit length, Pitch is the threads per unit length of the pedicle screw PS. The robotic controller 32 uses this relationship to control the installation of the pedicle screw PS. For example, taking the first derivative with request to time, the rate of change in angular position, or rotational rate, $\delta\theta/\delta t$, is equal to the rate of change in depth of insertion, or advancement rate, SD/St, multiplied by the Pitch divided by $2\pi$. This can be expressed as: $\delta\theta/\delta t = \delta D/\delta t * Pitch/2\pi$ (Eq. 1).

The robotic surgical system 10 may include a variety of accessories for preparing the anatomy for the pedicle screw PS. For example, one of the accessories of the surgical tool 30 may include a skin incision tool, such as a scalpel, electrosurgical knife, other tools with sharp tips, and the like. The skin incision tool can be mounted much like the drill 42 and/or driver 44, or may be part of a separate end effector and connected to a mount that attaches to the coupling 40, and a skin incision can be made with haptic guidance in a similar manner as previously described, i.e., virtual boundaries (e.g., haptic objects) can be used when creating the incision to constrain the operator's movement with respect to a desired incision in the patient's skin. In one example, a digitizing probe can be used to touch the desired incision location and create the associated boundary/haptic object. In another example, a 3-D skin model can be determined based on the pose of the a skin tracker, through digitizing, and/or through pre-operative methods, and the desired plan of pedicle screw placement can be used by the control system to determine the incision location based on the skin model.

Other types of pointers, similar to the digitizing probe can also be used to identify the desired location of the incision, such as a laser pointer that could be mounted to the skin incision tool, end effector, or other component to project visible light onto the skin of the patient to indicate the location of the incision. Such a laser pointer can be used by first aligning the rotational axis R of the skin incision tool with the desired trajectory and thereafter activating the laser pointer to project the light along the desired trajectory. An alternative form of skin incision tool is placed through a tool guide held in place by the robotic arm. Owing to the tracking of the patient's skin accomplished via the skin tracker, the navigation system 12 is also able to approximately determine the desired location of the incision based on the skin model (e.g., a surface model, point cloud, etc.) and the intersection of the desired trajectory with the skin model so that the operator is able to cut the desired incision in the patient's skin at the desired location by virtue of haptic feedback.

Haptic objects can be defined in various ways to establish the haptic feedback to guide making of the incision. The haptic objects can be defined based on a width of the skin incision tool, a desired length of the skin incision, and/or a desired depth of the incision. A desired incision depth can also be controlled by the operator within a maximum incision depth which can be determined by either the maximum incision depth programmed as part of the haptic object or a mechanical stop can be used to prevent the skin incision tool from sliding through a guide opening (not shown) in the tool guide TG of the end effector beyond a predetermined point.

One of the accessories of the surgical tool 30 may comprise a wire insertion tool, such as a Jamshidi needle, another access cannula with stylet, or the like. The wire insertion tool can be mounted much like the skin incision tool or may be part of a separate end effector and fixedly connected to a mount that attaches to the coupling 40. If no relative motion is allowed between the wire insertion tool and the mount, i.e., they are fixed to one another, then the wire insertion tool can be guided with a line haptic object to enter the skin incision and reach a target point on the bone, e.g., the vertebra. If relative axial sliding motion between the wire insertion tool and the mount is allowed, such as when the mount comprises a tool guide with opening, then the tool guide can be positioned at the desired orientation and the wire insertion tool can be inserted along opening in the tool guide. Depending on relative distance to the target point, length of the wire insertion tool, and the tool guide position, the wire insertion tool can be guided via the line haptic object in the same manner previously described for the drill 42 and/or driver 44.

Owing to the skin and the desired location for the incision being tracked, the robotic surgical system 10 can control movement of the skin incision tool with respect to a haptic object created for the incision. The haptic object is defined in the target coordinate system so that the incision is made at the desired location in the skin of the patient. In one example, the robotic surgical system 10 can control movement of the skin incision tool with respect to the haptic object by controlling manual manipulation of the skin incision tool. This can be done by constraining movement of the skin incision tool with respect to a virtual boundary defined by the haptic object so that the skin incision tool makes the incision at the desired location while an operator manually moves or manually causes movement of the skin incision tool. The robotic surgical system 10 can constrain movement of the skin incision tool with respect to the haptic object by generating haptic feedback to the operator to indicate that the skin incision tool has reached a desired depth of the incision or otherwise has reached a desired limit for the incision. Once the incision is made at the desired location, the skin incision tool is withdrawn away from the anatomy and the procedure proceeds until all incisions are made. Skin incision techniques can be like that described in United States Patent Application U.S. Ser. No. 16/184,376, filed Nov. 8, 2018, entitled "Robotic Spine Surgery System and Methods".

II. Haptic Feedback Techniques

As described above, the robotic surgical system 10 can be utilized to control the surgical tool 30 to rotate the screw along the planned trajectory. Described herein are techniques utilized in conjunction with the robotic surgical system 10 for providing the surgeon with a direct haptic "feel", contact or control of the force, energy, material and information flow involved while the robotic surgical system 10 causes the surgical tool 30 to interact with tissue. In turn, the techniques described herein provide a technical solution to emulate haptic and sensory information that a surgeon is (manually) accustomed to for monitoring and assessing the tissue interaction process during the surgical procedure. The haptic techniques described herein restore the ability of the surgeon to assess the process during the robotically controlled procedure. The solution provides an elegant mechanism for providing haptic feedback using, for example, one degree of freedom (e.g., rotation) and one concomitant phenomena (e.g., resistance). The haptic device can include an interface (e.g., knob) that controls or emulates interaction of the screw (or accessory) being manipulated by the robotic arm 20 and/or surgical tool 30. In some instances, the resistance of the interface is modulated or amplified and can dynamically change depending on interaction between the screw and the surrounding tissue into which the screw is inserted. In some instances, when the user manipulates the interface, the robot turns and advances the screw. The robotic surgical system captures the screw insertion process parameters through adequate sensors. The sensor information is then transformed and used to modulate the feedback to the interface giving the surgeon enhanced sensory acuity that helps the surgeon understand the consistency of the tissue in which the screw is being inserted and the quality of grip of the form fit between the screw and the tissue. In turn, the haptic techniques described herein increase surgeon confidence, reduce emotional stress, increase procedural efficacy, and provide the surgeon with the ability to perceive and react to unforeseen circumstances that are not otherwise captured by the robotic solution.

The haptic techniques described herein may be used in a variety of medical applications. For instance, although the haptic techniques relate to a screw insertion process, the haptic techniques may also be used in a variety of other medical applications. As an example, during a procedure including a scalpel or syringe, an interface of the haptic device may provide haptic feedback to emulate a force applied by the scalpel or the syringe as the scalpel or syringe progresses through different tissues. The haptic techniques may be used in procedures involving soft tissue to prevent damage to soft tissue. For example, during a procedure where a distractor separates soft tissue, an interface of the haptic device may provide haptic feedback to emulate a force applied to soft tissues by the distractor (or a tension applied by soft tissues on the distractor) as the distractor separates soft tissue at a wound site, at a surgical opening, between bones in joint space, or between bones during a bone growth procedure (e.g. mandibular distraction). As another example, during a procedure including a tourniquet, an interface of the haptic device may provide haptic feedback to emulate a pressure applied to soft tissue by the tourniquet. As yet another example, during a procedure including a jack for opening a joint space, an interface of the haptic device may provide haptic feedback to emulate a force applied to ligaments by the jack (or a tension by ligaments on the jack) to aid a ligament balancing process.

A. Haptic Device

Figure 10:
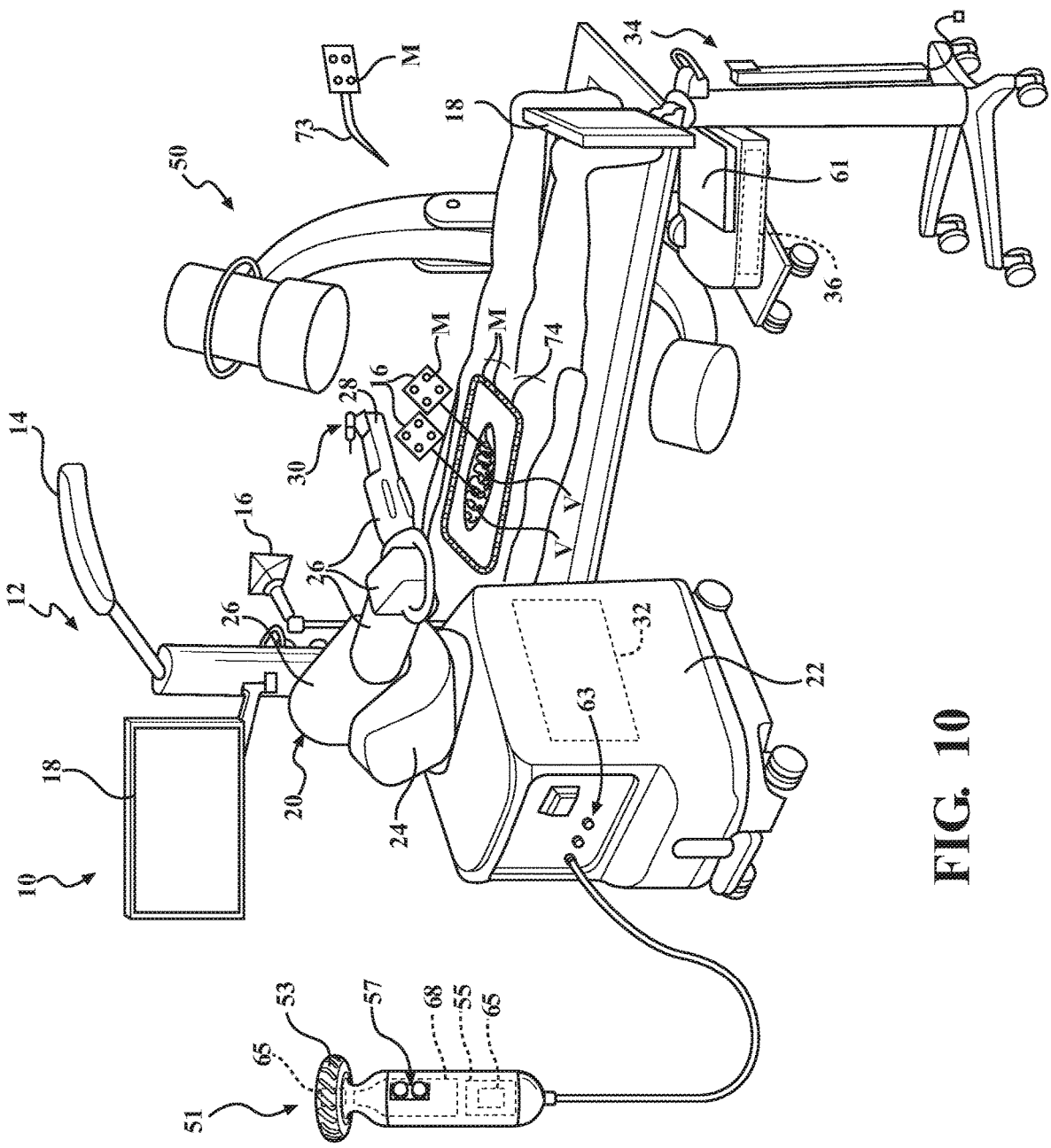
FIG. 10 is a perspective view of an instance of the robotic surgical system of FIG. 1 wherein the robotic surgical system includes a haptic device.

With reference to one example, as shown in FIG. 10, the robotic surgical system 10 includes a haptic device 51 for controlling the surgical tool 30. The haptic device 51 may include an interface 53 that may be manually manipulatable by a hand of the operator. In one non-limiting example, the haptic device 51 may be a hand-held pendant. Alternatively, the haptic device 51 may comprise a unit that can be rested on a surface, a haptic glove, or a physical design mimicking a tool (e.g., screwdriver) utilized in manual surgical procedures. The haptic device 51 may be any other device configured to provide the surgeon with the capabilities described herein.

The term "device" in haptic device is not limited to any specific embodiment(s) described herein. Indeed, the haptic device may comprise any device configured to provide a haptic (feel) to the operator wherein the haptic response emulates a condition occurring at an environment remote from the haptic device. This device may be comprised of any one or more of the following components to provide the appropriate haptic: mechanical components, electrical components, electro-mechanical components, software, controller(s), pneumatic components, hydraulic components.

In FIG. 10, the haptic device 51 is directly attached to the robotic manipulator or the surgical tool 30 via the base 22. In other instances, the haptic device 51 may be attached to any other suitable component of the robotic surgical system 10, such as the computer cart assembly 34 or the navigation system 12. In yet another example, the haptic device 51 may be coupled directly to the robotic arm 20 or the surgical tool 30 such that the haptic device 51 need not be held by the operator. The haptic device 51 may also remotely spaced apart from the robotic manipulator and the surgical tool 30, as shown in FIG. 10. In such instances, the haptic device 51 may be wirelessly coupled to the robotic surgical system 10. Alternatively, the haptic device 51 may be powered with a cord connected to the system 10 as shown in FIG. 10. In still other instances, the haptic device 51 may be used as a standalone device not necessarily attached to the robotic surgical system 10. For example, the haptic device 51 may be used with a surgical system that does not include the robotic manipulator and/or the navigation system 12.

The interface 53 of the haptic device 51 can move in a degree of freedom relative to the haptic device 51. In one example, the interface 53 is a rotational interface which can move in a rotational degree of freedom relative to the haptic device 51. In some examples, the rotational interface 53 may be a rotational knob, as shown in FIG. 10. The rotational interface 53 could also be a rotatable dial, ball, or wheel. The interface 53 may have configurations other than those specifically shown in the drawings or described herein.

The rotational interface 53 may be desired to enable the operator to associate the rotational degree of freedom of the rotational interface 53 to the rotational degree of freedom about which the screw or tool rotates. However, it is possible to realize the interface 53 of the haptic device 51 utilizing configurations other than the rotational interface 53. For example, the haptic device 51 may include a linear interface 53 that may be manually manipulatable by a hand of the operator. In some instances, the linear interface 53 may be a pivoting lever, push button, palm or finger trigger, spring switch, plunger, a compliant pad, or a slider. Furthermore, the one or more controllers 33 may control the actuator 55 of the haptic device 51 to enable the linear interface 53 to emulate a present interaction between the screw and the target site. For example, in an instance where the linear interface 53 is a push button, the one or more controllers 33 may control the actuator 55 such that the operator applies a greater or lesser force to depress the push button depending on the present interaction. In another example, where the linear interface 53 is a switch or plunger, the one or more controllers 33 may control the actuator 55 of the haptic device 51 such that the operator applies a greater or lesser force to actuate the switch or plunger. In yet another example, the linear interface 53 is a slider that includes a mechanism configured to slide along a path. The one or more controllers 33 may control the actuator 55 of the haptic device 51 such that the operator applies a greater or lesser force to actuate the slider and/or control the actuator 55 to limit the linear displacement of the slider.

The robotic surgical system 10 provides haptic feedback to the operator via the haptic device 51. As shown in FIG. 10, the haptic device 51 may include an actuator 55, which may be controlled by the one or more controllers 33. The actuator 55 is coupled to the interface 53 and is configured to apply a force to the interface 53. The actuator 55 may include a drive output drive shaft 68 coupled between the actuator 55 and the interface 53. The one or more controllers 33 may control the actuator 55 to enable the interface 53 to emulate a present interaction between the screw and the target site. In some instances, the interface 53 is utilized to directly control the surgical tool 30 and/or the driver 44 for rotating the screw. Direct control via the haptic device 51 can also be combined with the haptic feedback to emulate a present interaction between the screw and the target site. In these examples, the operator, through perception, can associate the degree of freedom of the interface 53 to the degree of freedom about which the screw moves.

The actuator 55 may be implemented as a motor, such as a brushed or brushless motor, a direct drive motor, active actuator, a DC motor, an electric linear motor, linear current control motor, stepper motor, an electric rotary motor, a torquer (motor with limited angular range), a spring-based actuator, a magnetic actuator, hydraulic actuator, pneumatic actuator, manual mechanical actuator, passive actuators, including magnetic particle brakes, friction brakes, damping resistance mechanism, or friction generating mechanism, or any combination thereof.

In some instances, the haptic device 51 may include safety features to prevent unintended use of the robotic surgical system 10 or haptic device 51. For example, the haptic device 51 may include a user interface 57 (dead man switch) that would need to be depressed for the interface 53 to be manipulatable. Similarly, the user interface 57 may need to be depressed for the haptic device 51 to transmit commands to the robotic surgical system 10. In another instance, the interface 53 may need to be depressed and held in a depressed position before being manipulated. In yet another instance, the haptic device 51 may include one or more sensors, such as a force sensor, a temperature sensor, a proximity sensor, an optical sensor, and/or a pressure sensor to enable the one or more controllers 33 to determine whether the operator's hand is contacting the haptic device 51.

The haptic device 51 may be utilized in a variety of operational modes, some of which are described in the table of FIG. 11A (the operation modes are referred to as "Haptic Device Operational Modes"). As shown, these operational modes include, but are not limited to: an "Autonomous Check Mode", a "Manual Control Mode", a "Simulated Autonomous Check Mode", and a "Simulated Manual Control Mode". The names of these modes are provided for simplicity in understanding and description, and hence, may be named in any other appropriate convention. The functions of these modes are fully understood based on the description provided below.

Referring to column B of the table of FIG. 11A, in each of the Haptic Device Operational Modes, the one or more controllers 33 provide haptic feedback to the haptic device 51. In the Autonomous Check Mode and the Manual Control Mode, the haptic device 51 emulates a present interaction between a pedicle screw PS and a target site. In the Simulated Autonomous Check Mode and the Simulated Manual Control Mode, the haptic device 51 emulates a present interaction between a simulated pedicle screw and a simulated target site. Any of these modes may be initiated automatically by the robotic surgical system 10, manually initiated by the operator, or initiated according to any other command.

Furthermore, the screw position and depth could be displayed on the display device for any control mode described herein.

B. Interaction Sensors

For any of the operational modes described herein, the robotic surgical system 10 may include one or more sensors coupled to the one or more controllers 33 to obtain the measurement indicative of the present interaction between an moveable element of the system (such as the implant, screw, and/or tool itself) and the target site. For example, the robotic surgical system 10 may include a position sensor configured to sense a position of the pedicle screw PS relative to the target site and/or a rotary encoder configured to sense rotations of the driver 44 of the surgical tool 30 or rotations of the pedicle screw PS. The robotic surgical system 10 may include a force sensor configured to sense a force imparted on the pedicle screw PS by the target site. The robotic surgical system 10 may include a torque sensor configured to sense a torque imparted on the pedicle screw PS by the target site and/or an electrical parameter sensor configured to sense an electrical parameter generated by an actuator of the surgical tool 30, wherein the electrical parameter is proportional to a torque imparted on the surgical tool 30 by the present interaction between the screw and target site. For example, in such instances an increase in torque may indicate that the pedicle screw PS has contacted or will contact a cortical wall, a quick drop off in torque may indicate that the pedicle screw PS has breached a cortical wall and has bottomed out. The robotic surgical system 10 may also include a proximity sensor configured to sense proximity of the pedicle screw PS relative to a feature of the target site, a depth sensor configured to sense a depth of the pedicle screw PS within the target site, and a displacement sensor configured to sense displacement of the pedicle screw PS relative to a feature of the target site.

In one implementation, the navigation system 12 additionally, or alternatively, determines the present interaction between the pedicle screw PS and the target site. As previously stated, pre-operative imaging and/or intra-operative imaging may be employed to visualize the patient's anatomy. For example, pre-operative images, e.g., X-rays, CT scans, or MRI images, may be used to create an anatomical (virtual) model of the patient's anatomy and, specifically, the target site. The anatomical model of the target site may be registered to the target site using any suitable registration method. The navigation system 12 can track the robot, tool, screw and/or patient and determine a position of the pedicle screw PS relative to the anatomical model of the target site. The navigation system 12 may include predetermined data indicative of expected interactions between the pedicle screw PS and the anatomical model at a plurality of positions of the pedicle screw PS relative to the anatomical model. In one example, the data may be stored in a look-up table in memory for access by the one or more controllers 33. The navigation system 12 may obtain a measurement indicative of the present interaction between the pedicle screw PS and the target site based on the determined state, position, orientation and/or pose of the screw relative to the anatomical model and the predetermined data. The predetermined data may include bone density data of the vertebra V. The navigation system 12 may use the bone density data and the state of the screw relative to the anatomical model of the vertebra V to obtain the measurement indicative of the present interaction between the pedicle screw PS and the vertebra V. e.g., at depth A shown in FIG. 12A. Predetermined data may also include known data about the geometry of the screw, tool, or any other feature relevant to define interaction.

Any combination of the above sensors, including the navigation system 12, may be combined to implement sensing between the moveable element and the target site.

C. Haptic Interaction Feedback

The controller 32 may emulate the present interaction between a pedicle screw PS and a target site by being configured to provide a physical feedback to the haptic device 51. As will be described below, the physical feedback can take various forms.

Any of the control modes described herein, "Autonomous Check Mode", "Manual Control Mode", "Simulated Autonomous Check Mode", and "Simulated Manual Control Mode" can fully utilize any of the haptic interaction feedback techniques described herein.

T0 enable these techniques, the haptic device 51 may be equipped with one or more sensors 65, as shown in FIG. 10, for sensing features of the haptic device 51. For example, the one or more sensors may detect any measurements related to the actuator 55, the interface 53, any combination thereof, or any other features. Such sensors 65 may be implemented as position or displacement sensors, incremental/absolute encoders, angle sensors, potentiometers, hall effect sensors, inductive sensors, capacitive sensors, inertial sensors, such as accelerometers, velocity/speed sensors, inclinometers, gyroscopes, force sensors, torque sensors, strain gage sensors, or any combination or equivalents thereof.

In some implementations, the one or more controllers 33 are configured to modify or limit mechanical motion of the interface 53 utilizing means other than, or in addition to, the actuator 55. For example, to influence of movement of the interface 53, the haptic device 51 may utilize mechanical components including but not limited to, biasing mechanisms, detents, ratchets, and/or gear systems, etc.; electrical components such as but not limited to, inductive, capacitive, and/or resistance elements; magnetic components; electromagnetic components; electro-mechanical components; hydraulic components; and/or pneumatic components.

In some implementations, the one or more controllers 33 are configured to prevent an ability to manually manipulate the interface 53. For example, the one or more controllers 33 may determine that a condition exists during control of the pedicle screw PS and, in response, may provide the operator with haptic feedback regarding the condition by controlling the actuator 55 of the haptic device 51 to prevent an ability to rotate the rotational interface 53. For example, the condition may include an error condition that would prevent an ability to rotate the rotational interface 53. These stopping conditions include the pedicle screw PS reaching a desired depth, the pedicle screw PS being rotated a predetermined number of rotations, a prediction of a contact point between the pedicle screw PS and a bone (as described in U.S. Patent Application Publication No. 2017/0000572 to Moctezuma de la Barrera et al., filed on Jun. 28, 2016, entitled "Robotic surgical systems And Methods For Controlling A Tool Removing Material From A Workpiece," which is hereby incorporated by reference herein), and/or the operator's subjective knowledge to stop (e.g. the operator may set an amount of time to rotate each pedicle screw PS).

Additionally, the condition may include an error condition, such as a fault detected within the robotic surgical system 10. In some instances, instead of preventing rotation of the rotational interface 53, the robotic surgical system 10 may provide the operator haptic feedback via vibrations and/or pulses. For example, the one or more controllers 33 may vibrate the haptic device 51 when the pedicle screw PS has reached a desired depth.

Any of the above haptic techniques can be utilized individually or in combination for any Modes or examples described herein, or equivalents thereof. Furthermore, the one or more controllers 33 may change or modify any of the haptic techniques in response to any condition, such as a reading from the interaction sensors, the sensors 65 of the haptic device 51, changing or initiating a control mode, or based on an input by the operator. Furthermore, any of the techniques described herein may be adapted for a rotational interface or linear interface of the haptic device 51.

1. Haptic Feedback—Resistive Force or Torque

In one example, the physical feedback is a resistive force applied to the interface 53. The actuator 55 can adjust a force or torque required to manipulate the interface 53 by the hand of the operator. The force required to manipulate the rotational interface 53 may reflect a present force required to rotate the screw relative to the target site. Since the interface 53 is coupled to the actuator 55, the actuator 55 can generate the resistive force to resist the motion in the degree of freedom of the interface 53.

For example, referring to FIG. 12A, the present force required to rotate the pedicle screw PS is illustrated as $F_{PS}$, the resistive force provided to the actuator 55 is illustrated as $F_A$, and the force required to rotate the rotational interface 53 is illustrated as $F_{RI}$. $F_{RI}$ is shown as a dotted line because $F_{RI}$ is experienced when the operator manually manipulates rotational interface 53. At various depths along the trajectory LH, a magnitude of the present force $F_{PS}$ varies, causing the resistive force $F_A$ and the force $F_{RI}$ to vary accordingly.

The controller 32 may control the actuator 55 to modulate, modify, amplify or otherwise dynamically change the resistive force. T0 do so, the controller 32 may modify operational voltage, frequency, or current of the actuator 55. The resistive force may be modeled or implemented as a spring force, a damper force, an impulse force, or the like. Furthermore, the resistive force may be based on position, velocity, and/or acceleration parameters.

In some instances, the robotic surgical system 10 may be configured to receive an input from the operator to selectively adjust the resistive force $F_A$ provided to the actuator 55. Additionally, the robotic surgical system 10 may be configured to receive an input from the operator to selectively adjust the sensitivity of the interface's 53 ability to control the surgical tool 30 to rotate the pedicle screw PS. In some instances, the resistive force $F_A$ and the sensitivity of the interface 53 are related. For example, the greater the resistive force $F_A$, the higher the sensitivity of the interface 53 and the smaller the resistive force $F_A$, the lower the sensitivity of the interface 53. Parameters that may be adjustable to modify the sensitivity of the interface 53 include, but are not limited to: spring parameters, damping parameters, force parameters, scaling factors between the rotational ratios of the actuator 55 and the interface 53, actuator parameters, magnitude of force, direction of force, displacement limits or ranges of interface 53 for any given resistive force, resistive force curves or slopes, and the like. For example, in instances where the interface 53 includes a spring and a spring parameter is adjusted, such a spring parameter may be spring rate, wherein a greater spring rate requires a greater force to actuate the interface 53. In such an instance, the spring may be formed of a compliant element such that the spring rate may be modified by changing material properties of the compliant element or by changing geometric properties of the compliant element.

In one example, the resistive force may be a restoring force having a magnitude proportional to a magnitude of the deviation of the interface 53 from a home position (zero detent) defined on the interface 53 or between the interface 53 and the actuator 55. The home position, for instance, may be the position of the interface 53 defined by the controller at the moment the haptic mode is initiated. In one example, the home position is defined at a static location relative to the haptic device 51. In another example, the one or more controllers 33 may dynamically adjust the location of the home position based on any existing condition, such as a reading from the interaction sensors, the sensors 65 of the haptic device 51, changing or initiating a control mode, completion of a task, or based on an input by the operator. Alternatively, the home position may be predefined mechanically, e.g., using physical detents, or the like.

In some implementations, the resistive force may yield to motion of the interface 53. In other words, the resistive force does not seek to restore a position of the interface 53 to any home position. The resistive force may be initially low in magnitude and may be increased in magnitude the further the interface 53 is moved from the home position.

In some instances, the resistive force is increased to a magnitude required to convey to the user that the screw PS has reached a limit relative to the target site. For example, this may be appropriate in situations where the screw may abut an interior cortical wall of the vertebral body, whereby the limit is provided to avoid breaching the cortical wall. In one example, the resistive force may be modeled as a barrier force effect, with a high magnitude of stiffness. Alternatively, in such instances, the controller may control the actuator 55 to apply a mechanical limit on motion of the interface 53.

In many examples, the resistive force is applied to resist rotational motion. However, the resistive force may be applied to resist linear motion. For example, the linear motion may resist linear motion of the interface 53. Such linear motion may be motion of a mechanism for a linear interface 53 such as a slider, push button, etc. Alternatively, or additionally, linear motion may be an example where the rotational interface 53 can be pushed down. The resistive force in such examples may resist the pushing down of the rotational interface 53.

The resistive force may be provided in response to different conditions relating to the present interaction between a pedicle screw PS and a target site. Any of these conditions can be detected by any of the interaction sensors described above.

In one example, a resistive force is applied to the interface 53 in response to rotational position of the pedicle screw PS. The screw PS position relative to a reference point is determined. The resistive force applied to the interface 53 can be progressively increased or decreased until the screw has reached the designated position. In this example, the home position of the interface 53 can be utilized. The interface 53 can be rotated away from the home position to command driving of the screw. While in the non-home position, the resistive force is applied to the interface 53. However, once a certain position is reached, the resistive force can be zeroed, and the interface 53 can spring back to the home position. Alternatively, the resistive force can be progressively decreased (up to zero) as the screw progressively comes closer to reaching the position.

In another example, resistive force is applied to the interface 53 in response to insertion depth of the pedicle screw PS. In this example, the home position of the interface 53 can be utilized. The interface 53 can be rotated away from the home position to command driving of the screw. While in the non-home position, the resistive force is applied to the interface 53. However, once the insertion depth is reached, the resistive force can be zeroed, and the interface 53 can spring back to the home position. Alternatively, the resistive force can be progressively decreased (up to zero) as the screw progressively comes closer to reaching the insertion depth.

In another example, resistive force is applied to the interface 53 in response to rotational velocity of the pedicle screw PS. In this example, the home position of the interface 53 can be utilized. The interface 53 can be rotated away from the home position to command driving of the screw. While in the non-home position, the resistive force can be progressively increased/decreased depending upon the rotational velocity of the screw.

In another example, resistive force is applied to the interface 53 in response to torque applied to the pedicle screw PS by the target site or in response to torque applied by the tool.

In another example, the one or more controllers 33 may also provide the operator haptic feedback via vibrations and/or pulses. For example, the one or more controllers 33 may adjust a frequency and/or amplitude of vibration of the haptic device 51 based on a present force required to rotate the screw relative to the target site. In a more specific example, the amplitude of vibration of the haptic device 51 may increase and the frequency of vibration of the haptic device 51 may decrease as the force required to rotate the screw relative to the target site increase. Similarly, the amplitude of vibration of the haptic device 51 may decrease and the frequency of vibration of the haptic device 51 may increase as the force required to rotate the screw relative to the target site decreases.

The resistive force may be implemented using any combination of the examples described herein, or equivalents thereof.

2. Haptic Feedback-Position

The interface 53 may employ feedback techniques other than resistive force. In one example, the interface 53 position is actively controlled (moved) by the actuator 55 in response to the present interaction between the screw PS and the target site to provide feedback to the operator. Any of these conditions can be detected by any of the interaction sensors described above.

In one example, the interface 53 position is controlled in response to rotational position of the pedicle screw PS. The position of the interface 53 can be actively rotated by the actuator 55 based on the real-time position of the screw. As the screw rotates, so too will the interface 53. In another example, the position of the interface 53 can be moved to a certain fixed position or between to inform the operator about any positional information relating the screw, such as a maximum position or depth of insertion. The interface 53 can include a graphical scale or indicia to correlate interface position to screw position.

In another example, the interface 53 position is controlled in response to torque applied to the pedicle screw PS by the target site or in response to torque applied by the tool. The position of the interface 53 can be actively moved by the actuator 55 to indicate to the operator various torque levels experienced by the screw. The interface 53 can include a graphical scale or indicia to correlate interface position to screw torque.

In yet another example, the interface 53 position is controlled in response to rotational velocity of the pedicle screw PS. The position of the interface 53 can be actively moved by the actuator 55 to indicate to the operator various velocity levels experienced by the screw. The interface 53 can include a graphical scale or indicia to correlate interface position to tool or screw velocity.

3. Haptic Feedback—Range of Motion

In another example, the interface 53 position is controlled to be limited in response to the present interaction between the screw PS and the target site to provide feedback to the operator. Any of these conditions can be detected by any of the interaction sensors described above.

In one example, the interface 53 is limited such that it is only allowed to rotate an amount that relates to the amount that the screw has turned. In another example, the interface 53 is limited such that it is only allowed to rotate an amount that relates to the depth that the screw has been inserted. In another example, the interface 53 is limited such that it is only allowed to rotate an amount that identifies where the screw has reached a physical or virtual boundary.

In another implementation, when the interface 53 is rotational, its range of motion may be controlled to allow to continuous rotation, e.g., any number of full 360 degree turns. This may be appropriate in certain control modes, as described below, such as when the haptic device 51 is utilized for allowing the user to manually control screw insertion by controlling the rotational interface 53 reach a velocity or force/torque for input control.

D. Autonomous Check Mode

One mode of the haptic device 51 is the Autonomous Check Mode. During the Autonomous Check Mode, the robotic surgical system 10 provides haptic feedback to the operator to emulate a present interaction between pedicle screws PS and a target site pursuant to autonomous insertion of the screw PS by the robotic surgical system 10. During the Autonomous Check Mode, the rotational interface 53 is manually manipulatable according to the force $F_{RI}$ to provide the operator with haptic feedback reflecting the present force $F_{PS}$ required to rotate the pedicle screw PS relative to the vertebra V. In other words, the Autonomous Check Mode enables the operator to "feel" the screw interaction at any given time before, during, or after autonomous screw insertion.

As indicated in columns B and D of the table of FIG. 11A, haptic feedback is provided to the haptic device 51 for the check, but the haptic device 51 does not control the surgical tool 30 or the driver 44 to insert pedicle screws PS during the Autonomous Check Mode since the screw is autonomously being inserted by the robotic surgical system 10 (See Column D, FIG. 11A).

FIG. 12A provides an example of the pedicle screw PS interacting with a target site, the vertebra V, during the Autonomous Check Mode. In FIG. 12A, the one or more controllers 33 autonomously control the insertion of the pedicle screw PS along the planned trajectory LH. In this case, the screw is self-tapping. Meanwhile, the one or more controllers 33 control the haptic device 51 to emulate the present interaction between the pedicle screw PS and the vertebra V. For example, when the pedicle screw PS is inserted to depth A along the planned trajectory LH, the one or more controllers 33 control the haptic device 51 to emulate the present interaction between the pedicle screw PS and the vertebra V at depth A. Hence, the robotic surgical system 10 provides the operator with a haptic sensation to experience screw PS insertion being performed by the robotic surgical system 10.

In one example, as outlined in column F in the table of FIG. 11A, the Autonomous Check Mode can be executed concurrently/during active and autonomous screw insertion by the robotic surgical system 10. In such an instance, by initiating the Autonomous Check Mode, the rotational interface 53 is controlled to be manually manipulatable such that the operator may receive haptic feedback from the robotic surgical system 10 via the rotational interface 53 as the screw is being autonomously inserted. In this example, autonomous screw insertion does not stop for the haptic check. As the screw PS continues to be autonomously inserted, the present interaction between the pedicle screw PS and the vertebra as the depth of insertion changes continuously. Accordingly, in this example, the resistive feedback to rotational interface 53 can be changed to reflect near-real time present interaction between the pedicle screw PS and the vertebra. Updates to the resistive force can be set according to any suitable time step, such as updated each N second, each N degree rotation of the screw, each N mm of screw displacement, etc.

Alternatively, as outlined in column F in the table of FIG. 11A, the Autonomous Check Mode may be initiated after the one or more controllers 33 stop or pause autonomously controlling the surgical tool 30 to stop rotation of the pedicle screw PS. In one example, the robotic surgical system 10 stops or pauses autonomously control in response to the operator triggering the Autonomous Check Mode. Alternatively, the robotic surgical system 10 stops or pauses autonomously control in response to any other system command, such as the user-initiated stopping of autonomous motion. In either instance, the system 10 controls the haptic device 51 to emulate the interaction between the pedicle screw PS and the vertebra present at the time when the system 10 was stopped or paused. After the Autonomous Check Mode is performed, the operator may reinitiate autonomous control of the robotic surgical system 10 to continue screw insertion.

In another example, as outlined in column F in the table of FIG. 11A, the robotic surgical system 10 may initiate the Autonomous Check Mode prior to the one or more controllers 33 autonomously controlling the surgical tool 30 to insert the pedicle screw PS. For example, the operator may be interested in the haptic feedback of the pedicle screw PS prior to the one or more controllers 33 autonomously controlling the surgical tool 30 to insert the pedicle screw PS. In such instances, the screw PS may be partially implanted according to manual insertion by the surgeon, with autonomous insertion to later follow. The existing interaction between the partially implanted screw PS and the target site can be reflected to the haptic device 51 for the surgeon to check before initiating autonomous insertion.

In some examples, initiation of the Autonomous Check Mode automatically initiates autonomous control of the surgical tool 30 by the one or more controllers 33. Similarly, when the Autonomous Check Mode is deactivated, the one or more controllers 33 may cease autonomous control of the surgical tool 30. Alternative instances of the Autonomous Check Mode, and capabilities and uses thereof are contemplated.

E. Manual Control Mode

In the Manual Control Mode, the operator utilizes the haptic device 51 to control the surgical tool 30 for purposes such as, but not limited to, inserting the pedicle screw PS. During the Manual Control Mode, the one or more controllers 33 do not autonomously control insertion of the pedicle screw PS (as shown in column D of FIG. 11A). Instead, the interface 53 of the haptic device 51 is manipulated to provide input to the one or more controllers 33 to control pedicle screw PS insertion. In response to control input from the haptic device 51, the one or more controllers 33 control the surgical tool to rotate the screw at the rotational rate about the rotational axis R and to linearly advance the screw at the advancement rate along the planned trajectory LH.

The manual control mode can be utilized before or after any of the other haptic device modes described herein. In one example, the robot can insert the screw autonomously to a desired or predetermined torque peak, depth of insertion, or number of screw rotations. Thereafter, the manual control mode may be utilized to complete the remainder of the task.

1. Manual Control Input

Referring to column G of the table of FIG. 11A for Manual Control Mode, the one or more controllers 33 may be configured to determine or receive an input control technique defining how the haptic device 51 can be utilized as an input.

Referring to the table of FIG. 11B, examples of these input control techniques include but are not limited to utilizing the haptic device 51 as a force or torque input, a rotation position input, or a rotational velocity input. The input control technique can be set according to surgeon preference, designated by the system, or any combination thereof. The operator may select the input control technique using the user interface 57 (shown in FIG. 10) of the haptic device 51 or any by other method, such as input into the display device 18.

In the manual control mode, the tool is controlled for inserting the screw responsive to the input from the haptic device 51. As will be described below, there are also various output techniques for controlling the screw that may be the same as, or different than, the technique utilized for input control.

a. Force or Torque Input from Haptic Device

Referring to FIG. 11B, one example input provided by the haptic device 51 is a force or torque input exerted on the interface 53 by the operator. As shown in FIG. 12B, the operator may apply a force Fin to manually manipulate the interface 53. This force Fin can also be an applied torque. The one or more controllers 33 may obtain a measurement of a force applied to the interface 53 to determine a desired force for inserting the pedicle screw PS and control insertion of the pedicle screw PS based on the desired force. The force or torque applied can be representative of the force or torque that the operator desires for between the screw PS and the target site.

For instance, the one or more controllers 33 may determine the desired force for inserting the pedicle screw PS based on the force $F_{in}$ used to manually manipulate the rotational interface 53 from the home position $P_0$ to a non-home position $P_1$, as shown in FIG. 11C. In each of these examples, the position $P_1$ is shown only as one possible example of many positions that the interface 53 may be in relative to the home position. In one example, the one or more controllers 33 may be configured to obtain a measurement of the force $F_{in}$ by measuring or calculating a torque applied to the rotational interface 53 when the operator applies the force $F_{in}$. In another example, the one or more controllers 33 may be configured to obtain a measurement of the force $F_{in}$ by determining an acceleration of the rotational interface 53 when the operator applies the force $F_{in}$.

In an instance where the robotic surgical system 10 includes the surgical tool 30 having a trigger 49 shown in FIGS. 4-6, the operator may control the insertion of a pedicle screw PS by manually manipulating the trigger 49 instead of the rotational interface 53 of the haptic device 51. In such an instance, the operator may depress the trigger 49 with a force $F_{in}$ and the trigger 49 may communicate signals to the one or more controllers 33 indicative of an operator's input.

The interface 53 may comprise a zero detent (home position $P_0$) so that the interface 53 returns to the home position when released by the operator after applying force. As such, the operator may apply a sequence of forces $F_{in}$ to the rotational interface 53 without moving their hand unnecessarily. In another example, the interface 53 can continue to rotate in the degree of freedom unimpeded to allow enough rotation of the interface 53 to achieve the desired force. As such, the rotational interface 53 provides a full 360-degree range of motion, allowing the operator to simulate rotating a screw with their hand.

b. Position Input from Haptic Device

In another example, the one or more controllers 33 may obtain a measurement of a position (or change of position) of the interface 53 to provide a control input. For example, in an instance where the operator manually manipulates the rotational interface 53 to the position $P_1$ from the home position $P_0$, the one or more controllers 33 may determine the desired rotational position of the pedicle screw PS based on the location of position $P_1$ relative to the location of the home position $P_0$. In some instances, the one or more controllers 33 may obtain a measurement of an angle of rotation of the rotational interface 53 at position $P_1$ relative to the home position $P_0$. The position may be determined using any suitable sensor, such as an incremental or absolute encoder coupled to the interface 53 and/or actuator 55. Displacement of the interface 53 relative to the home position $P_0$ can also be utilized to provide input. Alternatively, the position of the interface 53 relative to the full degree of motion (e.g., 360 degrees) of the interface 53 can be utilized as input regardless of the home position. Position may also consider a cumulative rotational count of the interface 53 relative to the full degree of motion (e.g., 1 and ½ turns or 540 degrees).

In one example, the interface 53 may comprise a zero detent (home position $P_0$) so that the interface 53 returns to the home position when released by the operator at the desired position. In another example, the interface 53 can continue to rotate in the degree of freedom unimpeded to allow enough rotation of the interface 53 to achieve the desired position.

c. Velocity Input from Haptic Device

In yet another example, input provided by the haptic device 51 is a velocity experienced by the interface 53 in response the operator manipulation. The one or more controllers 33 may obtain a measurement of a velocity of the interface 53 using any suitable sensing devices, such as inertial sensors, encoders, hall effect sensors, or the like. For example, as shown in FIG. 11B. assume the interface 53 is at home position $P_0$ at time $T_0$ and the operator manually manipulates the interface to move to position $P_1$ at time $T_1$. The one or more controllers 33 may determine the distance or displacement between $P_1$ and $P_0$ relative to the change in time $T_1$-$T_0$ to determine the velocity of the interface 53. This distance or displacement may be linear or angular. The one or more controllers 33 may utilize any suitable software or logic for computing velocity based on sensed readings, such as integrators, differentiators, look up tables or the like.

In one example, the interface 53 may comprise a zero detent (home position $P_0$) so that the interface 53 returns to the home position when released by the operator. In another example, the interface 53 can continue to rotate in the degree of freedom unimpeded to allow enough rotation of the interface 53 to achieve the desired velocity input.

The input control from the haptic device 51 may be any combination of force, position, and/or velocity.

2. Manual Control Output

In response to the control input from the haptic device 51 utilizing any of the input technique described above (force, position, velocity), the robotic surgical system 10 is configured to control insertion of the screw. Referring to FIG. 11B, the tool can be controlled to drive the screw according to various output control techniques. These output control techniques include force, rotational position, depth of insertion, and velocity. These output control techniques are described in greater detail below, and the output control techniques can be utilized in response to any input technique (force, position, velocity).

The one or more controllers 33 may be configured to determine or receive the output control technique defining how the tool should be operated in the manual control mode (i.e., force, rotational position, depth of insertion, and velocity). The output control technique can be set according to surgeon preference, designated by the system, or any combination thereof. The operator may select the output control technique using the user interface 57 (shown in FIG. 10) of the haptic device 51 or any by other method, such as input into the display device 18.

In all instances of the manual control mode output, the screw rotation and advancement rate are tied by the thread pitch according to the techniques described herein. Furthermore, the sensitivity of the interface 53 to cause control of the tool can be changed for any of the examples described herein. The sensitivity of the interface 53 can be manually or automatically updated to consider bone density.

a. Force Output Control of Tool

In response to any input technique (force, position, velocity), the one or more controllers 33 may operate to the tool to drive the screw PS based on force control.

In one example, the input position of the interface 53 determines the force output to the screw by the tool 30. The force output can be a torque. In one example, the input position of the interface 53 can determine a specific force or torque level the tool should apply to the screw and the tool 30 is controlled to apply the specified force or torque. In another example, the position of the interface 53 can determine a maximum force or torque level the tool should apply to the screw and the robot and tool 30 continue to insert the screw until the maximum force or torque is achieved. In these examples, the interface 53 may comprise a zero detent (home position $P_0$) so that the interface 53 returns to the home position when released by the operator.

In one example, the input velocity of the interface 53 determines the force output to the screw by the tool 30. For example, increases/decreases to the velocity of interface 53 can cause increases/decreases to the torque applied to the screw by the tool. In this example, the user may need to turn the interface 53 faster and faster to achieve the full screw insertion.

In yet another example, the input force or toque applied to the interface 53 causes the tool to apply a force or torque output to drive the screw. In one example, the input force or torque of the interface 53 can determine a specific force or torque level the tool should apply to the screw and the tool 30 is controlled to apply the specified force or torque. The input force or torque of the interface 53 can alternatively determine a maximum force or torque level the tool should apply to the screw and the robot and tool 30 continue to insert the screw until the maximum force or torque is achieved.

b. Rotational Position Output Control of Tool

In response to any input technique (force, position, velocity), the one or more controllers 33 may operate to the tool to drive the screw PS based on rotational position control. The rotational position can be defined as a rotational angle of the screw relative to a reference angle.

In one example, the input position of the interface 53 causes the tool to rotate the screw PS to a position. Alternatively, the displacement of the interface 53 causes the tool to rotate the screw PS according to a displacement.

In another example, the velocity input of the interface 53 causes the tool to rotate the screw PS to a position. Increases/decreases in input velocity of the interface 53 can also cause changes in output position control. In this example, the user may need to turn the interface 53 faster and faster to achieve the full screw insertion.

In another example, the force or torque input of the interface 53 causes the tool to rotate the screw PS to a position. In one example, the input force or torque of the interface 53 can determine a specific position to which the tool should drive to the screw. The input force or torque of the interface 53 can alternatively determine a maximum position to which the tool should drive the screw and the robot and tool 30 continue to insert the screw until the maximum position is achieved.

c. Depth of Insertion Output Control of Tool

In response to any input technique (force, position, velocity), the one or more controllers 33 may operate to the tool to drive the screw PS to a specific depth of insertion within the target site.

In one example, the input position of the interface 53 causes the tool to rotate the screw PS to a specific depth of insertion. Alternatively, the displacement of the interface 53 causes the tool to rotate the screw PS according to a depth of insertion.

In another example, the velocity input of the interface 53 causes the tool to rotate the screw PS to a specific depth of insertion. Increases/decreases in input velocity of the interface 53 can also cause changes in the depth of insertion. In this example, the user may need to turn the interface 53 faster and faster to achieve the full depth of insertion.

In another example, the force or torque input of the interface 53 causes the tool to rotate the screw PS to a specific depth of insertion. In one example, the input force or torque of the interface 53 can determine a specific depth of insertion to which the tool should drive to the screw. The input force or torque of the interface 53 can alternatively determine a maximum specific depth of insertion to which the tool should drive the screw and the robot and tool 30 continue to insert the screw until the specific depth of insertion is achieved.

d. Velocity Output Control of Tool

In response to any input technique (force, position, velocity), the one or more controllers 33 may operate to the tool to drive the screw PS based on velocity control. The velocity can be defined by the change with respect to time of: the rotational angle of the screw, linear insertion rate of the screw, rotational velocity of the tool, or any combination thereof.

In one example, the input velocity of the interface 53 causes the tool to rotate the screw PS according to a related velocity. Alternatively, the displacement of the interface 53 causes the tool to rotate the screw PS according to a related velocity.

In another example, the velocity input of the interface 53 causes the tool to rotate the screw PS according to a related velocity. Increases/decreases in input velocity of the interface 53 can also cause changes in output velocity control. In this example, the user may need to turn the interface 53 faster and faster to achieve a certain velocity.

In another example, the force or torque input of the interface 53 causes the tool to rotate the screw PS according to a related velocity. In one example, the input force or torque of the interface 53 can determine a specific velocity to which the tool should drive to the screw. The input force or torque of the interface 53 can alternatively determine a maximum velocity for which the tool should drive the screw and the robot and tool 30 continue to insert the screw until the maximum velocity is achieved.

c. Relationship Between Input and Output

Described above are various input control techniques provided by the haptic device 51 as well as various output control techniques for driving the tool. The relationship between the input of the haptic device 51 and the output to the tool can be defined according to various configurations, which are described below. The relationship between the input of the haptic device 51 and the output to the tool can be defined according to any combination of the various configurations described below.

The one or more controllers 33 may map the input of the haptic device 51 to a predetermined output to the tool, which may correspond to default settings for the tool. For example, a memory of the one or more controllers 33 may include a lookup table wherein inputs of the haptic device 51 correspond to predetermined default outputs to the tool. In one such instance, the one or more controllers 33 may obtain a measurement that the interface 53 is rotated 30 degrees. The one or more controllers 33 may then determine, based on a lookup table, that pedicle screw PS should be rotated with a rotational velocity of 1.5 rotations/sec.

The one or more controllers 33 may map the input of the haptic device 51 to a predetermined output to the tool, which may be based on a variety of variables. For example, the predetermined output to the tool may be based on conditions of the haptic device 51 that can be detected by any of the interaction sensors described above or the sensors 65. For instance, the predetermined output may be based on an insertion depth of the pedicle screw PS, the present force $F_{PS}$ required to rotate the pedicle screw PS, and/or bone density data of the vertebra V. As another example, the predetermined output to the tool may be based on a reading sensed by the sensors 65 of the user interface 57 of the haptic device 51. For instance, the user interface 57 may include a push button which may be depressed for "sensitive" control or a slider which may be actuated to indicate a desired sensitivity of control. The predetermined output may be based on a desired sensitivity of control, as sensed by the sensors 65.

The one or more controllers 33 may map the relationship between the input and output based on any suitable mathematical function such as monotonic, linear (e.g. proportional), exponential, logarithmic, polynomial, root, power, and rational functions. In one instance, the one or more controllers 33 may map the measured position to the desired insertion depth based on a linear function such that an amount of degrees that the rotational interface 53 is rotated is proportional to the desired insertion depth. For instance, for each degree that the rotational interface 53 is rotated, the one or more controllers 33 increases the desired insertion depth by ⅟₆₀th of a millimeter. In another instance, the one or more controllers 33 may map the measured position to the rotational velocity based on a piecewise constant function (i.e. a floor function). In such an instance, the one or more controllers 33 may map the measured position to the desired rotational velocity such that, when the rotational interface 53 is rotated between 1 and 180 degrees (inclusive), the one or more controllers 33 determines the desired rotational velocity to be 1 rotation/sec and when the rotational interface 53 is rotated between 181 and 360 degrees (inclusive), the one or more controllers 33 determines the desired rotational velocity to be 2 rotation/sec.

The one or more controllers may map any input technique (force, position, velocity) to an output control of the tool (force, rotational position, depth of insertion, velocity) based on a mapping relationship between the input of the haptic device 51 and the output to the tool.

As shown in column D of FIG. 11B, a force input may be mapped to a rotational position output, a depth of insertion output, a force output, or a velocity output. For instance, the force input may be linearly mapped to the rotational position output such that a measurement of the force input (a measurement of $F_{in}$) may be mapped to a proportional degrees of screw rotation. Similarly, the force input may be linearly mapped to the depth of insertion output, the force output, and the velocity output such that the force input may be mapped to a proportional depth of screw insertion, a proportional torque applied to the pedicle screw PS, and a proportional velocity of the screw insertion.

As shown in column D of FIG. 11B, a position input may be mapped to a rotational position output, a depth of insertion output, a force output, or a velocity output. For instance, the position input may be linearly mapped to the rotational position output such that a measurement of the position input (a measurement of position $P_1$ or a measurement of a displacement between position $P_1$ and $P_0$) may be mapped to a proportional degrees of screw rotation. Similarly, the position input may be linearly mapped to the depth of insertion output, the force output, and the velocity output such that the measurement of position $P_1$ relative to the home position $P_0$ may be mapped to a proportional depth of screw insertion, a proportional maximum torque level that should be applied the pedicle screw PS, and a proportional velocity of the screw insertion.

As shown in column D of FIG. 11B, a velocity input may be mapped to a rotational position output, a depth of insertion output, a force output, or a velocity output. For instance, the velocity input may be linearly mapped to the rotational position output such that a measurement of the velocity input (a measurement of a displacement between $P_1$ and $P_0$ relative to a change in time $T_1$-$T_0$) may be mapped to a proportional degree of screw rotation. Similarly, the velocity input may be linearly mapped to the depth of insertion output, the force output, and the velocity output such that the velocity input may be mapped to a proportional depth of screw insertion, a proportional torque applied to the pedicle screw PS, and a proportional velocity of the screw insertion.

F. Simulated Modes

The techniques relating to the haptic device 51 described above have been related to intraoperative techniques utilizing physical robot control and/or driving to the tool. However, it is contemplated to utilize the haptic device 51 to perform simulations in order to provide training or greater confidence to the operator in using the robotic surgical system prior to executing the actual surgical procedure. With reference to the table of FIG. 11A, and FIGS. 14A-14C, there are various simulated modes that can be utilized with the haptic device 51. These modes include a Simulated Autonomous Check Mode and a Simulated Manual Control Mode, and these modes are described in detail below.

The Simulation Modes may simulate the entire operation room condition that may exist intraoperatively, including but not limited to, the patient, robotic surgical system, robotic manipulator, patient table, navigation system, tool, screw. The simulation may alternatively simulate: the screw and target site; the tool, screw and target site; or the robotic manipulator, tool, screw, and target site. Furthermore, the surgical plan including target trajectory and depths of insertion can be provided in the simulation for reference.

The simulations can be executed on any suitable graphical display device, such as, but not limited to one or more of the displays 18 of the robotic surgical system 10, or a display that is outside of the operating room. The one or more controllers 33 may execute the simulations. Alternatively, the haptic device 51 can be connected to a simulation system separate from the robotic surgical system 10 where the simulation system has its own control system.

The Simulated Modes described herein may be executed pre-operatively or intraoperatively. For example, the surgeon can perform the simulation in the operating room just moments before commanding performance of physical robotic control. Alternatively, the simulation can be performed prior to surgery. In either instance, the surgeon may set, confirm or modify any operational parameters of the robotic surgical system 10 that are experienced during the simulation. For example, the surgeon may set, confirm, or modify: the surgical plan, such as pedicle screw size, depth of insertion, pedicle entry point location; haptic device operation or sensitivity; preferred control input technique (force/torque, position, velocity) of the haptic device; tool operation, feed rate, linear advancement rate, rotational speed, or sensitivity; preferred control output technique for the tool (force/torque, position, velocity); robotic parameters such as pose or orientation, and the like.

As previously stated, pre-operative imaging and/or intraoperative imaging may be employed to visualize the patient's anatomy. For example, pre-operative images, e.g., X-rays, CT scans, or MRI images, may be used to create an anatomical model of the patient's anatomy and, specifically, the target site. This virtual anatomical model can be utilized in the simulations. Additionally, once the thread geometry of the pedicle screw PS is stored in a memory of the robotic surgical system 10, the selected pedicle screw PS may be presented virtually within the simulation.

During execution of the Simulated Modes, the one or more controllers 33 provide haptic feedback to the haptic device 51. The one or more controllers 33 are configured to control the actuator 55 of the haptic device 51 to enable the rotational interface 53 to emulate a simulated present interaction between the pedicle screw PS and the target site. Referring to FIGS. 14B and 14C, the one or more controllers 33 may emulate the simulated present interaction by being configured to provide a resistive force $F_A$ to the actuator 55 to adjust a force $F_{RI}$ required to rotate the rotational interface 53 by the hand of the operator, wherein the force required to rotate the rotational interface 53 reflects a simulated present force, illustrated as $F_{SPS}$ in FIG. 14C, required to rotate the pedicle screw PS relative to the vertebra V (the target site). Of course, the haptic device 51 can be controlled to provide haptic feedback using any technique other than resistive feedback, such as force, position, or range of motion feedback techniques described above.

During execution of the Simulated Modes the one or more controllers 33 may be configured to obtain a simulated present interaction between the (simulated) pedicle screw PS and the (simulated) target site using a variety of methods. For example, the one or more controllers 33 may obtain a virtual measurement corresponding to the simulated present interaction in a coordinate system of the simulation. The simulation system can track the simulated robot, tool, screw and/or patient and determine a position of the simulated pedicle screw PS relative to the anatomical model of the target site. The simulation system may include predetermined data indicative of expected interactions between the simulated pedicle screw PS and the anatomical model at a plurality of positions of the simulated pedicle screw PS relative to the anatomical model. In one example, the data may be stored in a look-up table in memory for access by the one or more controllers 33. The simulation system may compute parameters indicative of the simulated present interaction between the pedicle screw PS and the target site based on the determined state, position, orientation and/or pose of the screw relative to the anatomical model and the predetermined data. The predetermined data may include bone density data of the vertebra V. The simulation system may use the bone density data and the state of the screw relative to the anatomical model of the vertebra V to compute or obtain parameters indicative of the simulated present interaction between the pedicle screw PS and the vertebra V at various depths. Predetermined data may also include known data about the geometry of the screw, tool, or any other feature relevant to define interaction.

1. Simulated Autonomous Check Mode

In one sense, the Simulated Autonomous Check Mode is a simulated version of the Autonomous Check Mode. Hence, any description of the Autonomous Check Mode above can be incorporated herein to understand the Simulated Autonomous Check Mode. During the Simulated Autonomous Check Mode, the one or more controllers 33 (graphically) simulate autonomously controlling the surgical tool 30 and the operator can use the haptic device 51 to haptically sense simulated autonomous insertion. The one or more controllers 33 simulate autonomously controlling the surgical tool 30 by simulating rotating the pedicle screw PS at the rotational rate about the rotational axis R and by simulating linearly advancing the pedicle screw PS at the advancement rate along the planned trajectory LH. However, the robotic surgical system is not physically controlling operation of the tool. Instead, the one or more controllers 33 simulate autonomous control of the surgical tool 30 (as shown in column E of FIG. 11A) to simulate autonomously inserting the pedicle screw PS. During the Simulated Autonomous Check Mode, the rotational interface 53 may be manually manipulated according to the adjusted force $F_{RI}$, but without an ability to control the simulated surgical tool 30 to rotate the pedicle screw PS and without an ability to control the simulated autonomous control of the surgical tool 30. Just like the Autonomous Check Mode, the Simulated Autonomous Check Mode may be performed before, during, or after stopping/pausing the simulation of autonomous screw insertion.

2. Simulated Manual Control Mode

In one sense, the Simulated Manual Control Mode is a simulated version of the Manual Control Mode. Hence, any description of the Manual Control Mode above can be incorporated herein to understand the Simulated Manual Control Mode. In contrast to the Manual Control Mode, during the Simulated Manual Control Mode, the interface 53 is manually manipulatable without an ability to control the (physical) surgical tool 30. Instead, the one or more controllers 33 simulate manual control of the surgical tool 30 in response to the operator manually manipulating the interface 53 of the haptic device 51 (as shown in column E of FIG. 11A). During the Simulated Manual Control Mode, the one or more controllers 33 simulate manually controlling the surgical tool 30 responsive to input from the haptic device 51. During the Simulated Manual Control Mode, the one or more controllers 33 simulate controlling one of the rotational rate or the advancement rate of the pedicle screw PS. The operator manually manipulates the haptic device 51 and, in response, the one or more controllers 33 may simulate control one of the rotational rate or the advancement rate of the pedicle screw PS (as shown in column G of FIG. 11A). For example, the operator may manually manipulate the interface 53 using any input technique described above. In response to the control input, the one or more controllers 33 control output of the simulated tool based on any suitable output technique, such as force, position or velocity for simulated insertion of the pedicle screw PS. In the example, as shown in FIG. 14C, the user applies an input force $F_{in}$ to the interface 53 to effect simulated manual control of screw insertion on the display 18. The input force is resisting the (resistive) force $F_{RI}$ outputted by the actuator 55.

III. Methods of Controlling the Robotic Surgical System

Referring now to FIG. 15A, a flowchart illustrates one example of a method of controlling the robotic surgical system 10. As shown, the flowchart illustrates operation of the various Haptic Device Operational Modes during a procedure.

The flowchart illustrates the method of controlling the robotic surgical system 10 to insert or simulate inserting a pedicle screw PS. The method starts at step 200 and proceeds directly to step 202 of preparing the anatomy for receiving the pedicle screw PS. During step 202, a variety of steps may be executed to prepare the anatomy for inserting a pedicle screw PS. These steps may include a step (1) of forming an incision in the patient, a step (2) of retracting tissue with a tissue retractor; a step (3) of placing a cannula in the retracted tissue, a step (4) of drilling a pilot hole 102 in the anatomy, and a step (5) of tapping threads into the anatomy. It should be noted that step 202 need not include the above steps (1)-(5). For example, in alternative instances, the step (4) and (5) may be excluded as the drilling of pilot holes 102 and the tapping of threads into the anatomy may be excluded. For example, such instances include instances where a self-drilling, self-tapping bone screw is employed.

The method then proceeds to step 204 where a pedicle screw PS is interacted with by the surgical tool 30. In some implementations, the tool 30 is coupled to the screw PS before interacting with the anatomy. Alternatively, the pedicle screw PS may be seated partially into the anatomy at the target site using any technique, including manual or robotic insertion, and thereafter, the tool 30 interacts with the partially seated screw PS. More likely, the pedicle screw PS is attached to a distal end of the driver 44 for placement in one of the pilot holes 102. The original line haptic object could be used for inserting the pedicle screw PS or a new line haptic object, with new starting point, target point, and exit point, could be created upon attaching the driver 44 and/or pedicle screw PS. In this case, the drill 42 and/or driver 44 could have RFID tags or other identification devices so that the one or more controllers 33 are able to identify which accessory is connected to the housing 45. The housing 45 may have a corresponding RFID reader, etc. in communication with the one or more controllers 33 to read the tag and determine which accessory is attached. Based on this information, the controller may then create, access, or otherwise determine a new line haptic object. Similarly, the pedicle screws PS could also be outfitted with RFID tags and the driver 44 may have a similar reader so that the one or more controllers 33 can also determine which size/type of pedicle screw PS is attached. Accordingly, the line haptic object can be based on the driver 44 and/or the pedicle screw PS so that the robotic arm 20 is controlled precisely to place that particular pedicle screw PS to a desired location, e.g., a desired orientation and depth with respect to the patient's anatomy.

Additionally, with automatic detection of the accessory, either via the RFID tags, or other detection devices, such as a vision camera, the control system is able to advance any surgical procedure software utilized with the robotic surgical system 10 to the next screen associated with the driver 44, which may have different prompts, instructions, etc. for the operator now that the driver 44 is connected. Voice recognition, gesture sensing, or other input devices may be used to advance the software and/or to change to the next vertebra 100 to be treated and/or to change a side of the vertebral body 100 in which the operation is being carried out. This could also be based on the location of the surgical tool 30. For example, if the TCP of the attached accessory is manually placed by the operator closer to one side of a vertebra V than another, the software may automatically advance to correspond to that side of the vertebra V. The selected vertebra V and side of operation can be confirmed visually with the displays 18 or through audio input/output.

In some procedures, the rotational axis R may be moved off the desired trajectory between drilling the pilot holes 102 and inserting the pedicle screws PS, such as when all the pilot holes 102 are drilled first, and then later, all the pedicle screws PS are inserted into their desired location. In such a case, before placing each of the pedicle screws PS, the robotic surgical system 10 may first control movement of the surgical tool 30 to place the rotational axis R along the desired trajectory by autonomously aligning the rotational axis R of the surgical tool 30 with the desired trajectory for each of the pedicle screws PS in the manner previously described.

The method proceeds to step 208 where the one or more controllers 33 determine which Haptic Device Operational Mode is selected, if the operator does not end operation of the procedure during step 206 (step 206 will be described in greater detail below). The Haptic Device Operational Mode may be selected in response to any condition or a command. During step 210, the method determines whether the selected Haptic Device Operation Mode is currently being executed by the one or more controllers 33. If the selected Haptic Device Operation Mode is not being executed by the one or more controllers 33, then the method first proceeds to step 212 where the one or more controllers 33 end the Haptic Device Operation Mode that is being executed if a Haptic Device Operation Mode is being executed. In response, the method proceeds to one of the Autonomous Check Mode, the Manual Control Mode, the Simulated Autonomous Check Mode, or the Simulated Manual Control Mode based on the selected Haptic Device Operation Mode. If the selected Haptic Device Operation Mode is already being executed, the method continues executing the selected Haptic Device Operation Mode. As such, during steps 208 and 210, the one or more controllers 33 determine if a condition prompts initiating of a Haptic Device Operational Mode or if the operator commands initiating of a Haptic Device Operational Mode.

As such, any Haptic Device Operation Mode may be initiated at any suitable time in response to a condition or a command. For example, in response to a condition or a command, the one or more controllers 33 may be configured to initiate the Manual Control Mode after stopping or pausing autonomously controlling the surgical tool 30 to stop rotation of the pedicle screw PS (also indicated in column F of FIG. 11A). As another example, in response to a condition or a command, the one or more controllers 33 may be configured to initiate the Manual Control Mode prior to autonomously controlling the surgical tool 30 (also indicated in column F of FIG. 11A). In such instances, the one or more controllers 33 may switch from the Manual Control Mode to resuming autonomously controlling the surgical tool to rotate the screw after autonomous control of the surgical tool 30 to is stopped or paused. Yet another example, in response to a condition or a command, the one or more controllers 33 may be configured to initiate the Simulated Autonomous Check Mode prior to or after stopping or pausing autonomous control of the surgical tool (also indicated in column F of FIG. 11A). As still yet another example, in response to a condition or a command, the one or more controllers 33 may be configured to initiate the Simulated Manual Control Mode prior to or after stopping or pausing autonomous control of the surgical tool (also indicated in column F of FIG. 11A).

The ability to initiate any Haptic Device Operation Mode at any suitable time provides the operator the ability to customize a procedure based on their preferences. For example, in one configuration where the one or more controllers 33 initiate the Manual Control Mode after stopping or pausing autonomously controlling the surgical tool 30, the one or more controllers 33 may initially insert the pedicle screws PS autonomously to an initial depth before the operator implants the pedicle screw PS to a final depth during the Manual Control Mode (or vice versa). In such a configuration, the pedicle screws PS may be placed autonomously until the pedicle screws PS are within a predefined distance of the final depth (as determined by the navigation system 12). At this point, the operator may either finish implanting the pedicle screw PS manually with the surgical tool 30 so that the operator is able to more actively feel tightening of the pedicle screws PS. The operator may also elect to use a separate tool (powered or manual) to complete placement of the pedicle screw PS during the Manual Control Mode than is used during autonomous control.

Other configurations also illustrate the operator's ability to customize a procedure based on their preferences. For example, in another configuration, the one or more controllers 33 initiate the Simulated Autonomous Check Mode prior to autonomously controlling the surgical tool 30. In such a configuration, the operator may visualize a simulation of an autonomous control of the surgical tool 30 on the display 18 before the one or more controllers 33 initiate the autonomous control to insert the pedicle screw PS. In another configuration, the one or more controllers 33 initiate the Simulated Manual Control Mode prior to initiating the Manual Control mode to control the surgical tool 30. In such a configuration, the operator may visualize a simulation of a manual control of the surgical tool 30 on the display 18 before the one or more controllers 33 initiate the Manual Control Mode to manually control to insert the pedicle screw PS.

Furthermore, the ability to initiate any Haptic Device Operation Mode in response to a condition or a command eliminates potential errors (e.g. collisions with the spinal cord 103) and provides the operator on-the-fly control of the procedure. For example, in the above described configuration where the one or more controllers 33 initially insert the pedicle screws PS autonomously to an initial depth before the operator implants the pedicle screw PS to a final depth during the Manual Control Mode, the one or more controllers 33 may initiate the Manual Control Mode in response to a condition or a command. In an instance where initiation of the Manual Control Mode and stopping of autonomous control is prompted by a condition, the one or more controllers 33 may detect that the pedicle screws PS are within the predefined distance of the final depth during autonomous control and transmit the condition to the one or more controllers 33. The one or more controllers 33 are then prompted to initiate the Manual Control Mode and stop the autonomous control such that the operator may manually complete placement of the pedicle screw PS. The predefined distance of the final depth may be predetermined such that the pedicle screw PS does not contact the spinal cord 103. In an instance where initiation of the Manual Control Mode is commanded by a command, the operator may be instructed by the navigation system 12 of a status of the autonomous control. For example, the displays 18 may indicate how many turns remain before the pedicle screw PS has reached full depth, and/or the displays 18 may graphically represent the pedicle screws PS, anatomy, and/or the target point so that the operator is able to easily visualize how much further insertion of the pedicle screw PS is required. The one or more controllers 33 may also provide the operator haptic feedback via the haptic device 51 (e.g. vibrations or pulses) to notify the operator that the pedicle screw PS has reached predetermined depth. Once the operator determines that the pedicle screw PS is within the predefined distance of the final depth, the operator may command the one or more controllers 33 to initiate the Manual Control Mode and stop autonomous control such that the operator may manually complete placement of the pedicle screw PS.

Some example conditions that may prompt initiating of a Haptic Device Operational Mode may include the pedicle screw PS reaching a desired depth, the pedicle screw PS potentially colliding with the spinal cord 103, and the pedicle screw PS being rotated a predetermined number of rotations. In such instances, the one or more controllers 33 may be configured to automatically select one of the Autonomous Check Mode, the Manual Control Mode, the Simulated Autonomous Check Mode, or the Simulated Manual Control Mode. In one such example, after the one or more controllers 33 have autonomously controlled the surgical tool 30 to rotate the pedicle screw PS a predetermined number of rotations, the one or more controllers 33 may be configured to automatically select the Manual Control Mode to allow the operator to manually complete insertion of the pedicle screw PS.

The robotic surgical system 10 may include a variety of components for commanding the initiating of a Haptic Device Operation Mode. For example, the operator may command the initiating of a Haptic Device Operation Mode using the haptic device 51. As shown in FIG. 10, the haptic device 51 may include a user interface 57. The operator may select the Haptic Device Operation Mode using the user interfaces 57 by actuating the user interface 57 to transmit a command to the one or more controllers 33. Alternatively, in some instances, the operator may depress the rotational interface 53 to select the Haptic Device Operation Mode. In instances where the robotic surgical system 10 includes the surgical tools 30 of FIGS. 4-6, the operator may select the Haptic Device Operation Mode using the trigger 49 or a user interface 59 of the surgical tool 30. In other instances, the operator may select the Haptic Device Operation Mode via a user interface of the computer cart assembly 34, such as the keyboard 61 of the computer cart assembly 34. The operator may also select the Haptic Device Operation Mode via a user interface 63 of the base 22. It is contemplated that an individual other than the operator may command the initiating of a Haptic Device Operation Mode. For example, the initiating of a Haptic Device Operation Mode may be commanded by a remote user from a remote location using a remote user interface.

FIG. 15B illustrates example steps of the Autonomous Check Mode. As shown, the Autonomous Check Mode includes a step 304 of obtaining a measurement indicative of a present interaction between the pedicle screw PS and the target site; a step 306 of controlling the actuator of the haptic device based on the obtained measurement to enable a rotational interface 53 of a haptic device 51 to emulate the present interaction between the pedicle screw PS and the target site, which includes a step 308 of providing a resistive force $F_A$ to an actuator 55 of the haptic device 51 to adjust a force $F_{RI}$ required to rotate the rotational interface 53 by the hand of the operator, wherein the force $F_{RI}$ required to rotate the rotational interface 53 reflects a present force $F_{PS}$ required to rotate the pedicle screw PS relative to the target site; and a step 310 of manually manipulating the rotational interface 53 according to the adjusted force $F_{RI}$ to provide the operator with haptic feedback reflecting the present force $F_{PS}$ required to rotate the pedicle screw PS relative to the target site without an ability to control the surgical tool 30.

FIG. 15C illustrates example steps of the Manual Control Mode. As shown, the Manual Control Mode includes a step 300 of manually manipulating the rotational interface 53 with an ability to control one of a rotational rate of the pedicle screw PS or an advancement rate of the pedicle screw PS based on the operator manually manipulating the rotational interface 53; a step 302 of controlling the surgical tool 30 to rotate the pedicle screw PS at the rotational rate about the rotational axis and to linearly advance the pedicle screw PS at the advancement rate along the planned trajectory in response to the rotational interface being manually manipulated to control one of the rotational rate of the pedicle screw PS or the advancement rate of the pedicle screw PS; the previously-described steps 304, 306, and 308; and a step 311 of manually manipulating the rotational interface 53 according to the adjusted force $F_{RI}$ to provide the operator with haptic feedback reflecting the present force $F_{PS}$ required to rotate the pedicle screw PS relative to the target site.

FIG. 15D illustrates example steps of the Simulated Autonomous Check Mode. As shown, the Simulated Autonomous Check Mode includes a step 312 of simulating autonomously controlling the surgical tool 30 by simulating rotating the pedicle screw PS at a rotational rate about the rotational axis R and linearly advancing the screw at an advancement rate along the planned trajectory LH; a step 314 of displaying the simulated autonomous control of the surgical tool 30 on the display 18; an instance of step 304 (illustrated as step 304') of obtaining a measurement indicative of a simulated present interaction between the pedicle screw PS and the target site; an instance of the step 306 (illustrated as step 306') of controlling the actuator of the haptic device based on the obtained measurement to enable a rotational interface 53 of a haptic device 51 to emulate the simulated present interaction between the pedicle screw PS and the target site, which includes an instance of the step 308 (illustrated as step 308') of providing a resistive force $F_A$ to the actuator 55 to adjust a force $F_{RI}$ required to rotate the rotational interface 53 by the hand of the operator, wherein the force $F_{RI}$ required to rotate the rotational interface 53 reflects a simulated present force $F_{SPS}$ required to rotate the pedicle screw PS relative to the target site; and a step 316 of manually manipulating the rotational interface 53 according to the adjusted force $F_{RI}$ to provide the operator with haptic feedback reflecting the simulated present force $F_{SPS}$ without an ability to control the surgical tool 30 to rotate the pedicle screw PS and without an ability to control the simulated autonomous control of the surgical tool 30.

FIG. 15E illustrates example steps of the Simulated Autonomous Check Mode. As shown, the Simulated Autonomous Check Mode includes a step 318 of manually manipulating the rotational interface 53 without an ability to control the surgical tool 30 to rotate the pedicle screw PS and with an ability to control one of the rotational rate of the pedicle screw PS or the advancement rate of the pedicle screw PS based on the operator manually manipulating the rotational interface 53; a step 320 of simulating manually controlling the surgical tool 30 by rotating the pedicle screw PS at the rotational rate about the rotational axis R and linearly advancing the pedicle screw PS at the advancement rate along the planned trajectory LH in response to the rotational interface 53 being manually manipulated to control one of the rotational rate of the pedicle screw PS or the advancement rate of the pedicle screw PS; a step 322 of displaying the simulated manual control of the surgical tool 30 on the display 18; the previously-described step 304'; the previously described step 306', which includes the previously described step 308'; and a step 324 of manually manipulating the rotational interface 53 according to the adjusted force $F_{RI}$ to provide the operator with haptic feedback reflecting the simulated present force $F_{SPS}$ without an ability to control the surgical tool 30 to rotate the pedicle screw PS.

Referring to FIG. 15A, a dashed line box illustrates a step 214 of autonomously controlling the surgical tool 30 to insert the pedicle screw PS. After the step 202 of preparing the anatomy and step 204 of placing the pedicle screw PS on the surgical tool 30, step 214 may occur concurrent to any of the steps 206 208, 210, and the Autonomous Check Mode. As previously stated, during the Manual Control Mode, the Simulated Autonomous Check Mode, and the Simulated Manual Control Mode, the one or more controllers 33 are not autonomously controlling the surgical tool 30. As such, if the one or more controllers 33 initiate any one of the Manual Control Mode, the Simulated Autonomous Check Mode, and the Simulated Manual Control Mode, the one or more controllers 33 cease execution of step 214 and stops autonomous control of the surgical tool 30 (if the one or more controllers 33 are autonomously controlling the surgical tool 30). However, at any time during any of the steps 206, 208, 210, or during the Autonomous Check Mode, step 214 may be executed and the one or more controllers 33 may concurrently initiate autonomous control of the surgical tool 30.

Step 214 of autonomously controlling the surgical tool 30 is further illustrated in FIG. 15G. As shown, the method comprises a step 400 of tracking a position of the target site; a step 402 of placing the rotational axis R along the desired trajectory; a step 404 of controlling movement of the robotic manipulator to maintain the rotational axis R of the surgical tool 30 along a planned trajectory LH with respect to the target site based on the tracked position of the target site; and a step 406 of autonomously control the surgical tool 30 to rotate the pedicle screw PS at a rotational rate about the rotational axis R and to linearly advance the pedicle screw PS at an advancement rate along the planned trajectory LH wherein the rotational rate and the advancement rate are predetermined and proportional to a known thread geometry of the pedicle screw PS.

During step 400, the position of the target site is tracked. An ultrasound transducer (not shown) could be mounted on the back of the patient's skin to generate real-time images of the patient's anatomy and progress of the surgical procedure. The intra-operative images could be used to determine that the pedicle screw PS follows the planned desired trajectory or to determine if the drill 42 or pedicle screw PS, is getting close to any critical structures including a nerve and medial or lateral cortical boundary.

During step 402, the rotational axis R is aligned with the planned trajectory LH. If the rotational axis R is not yet aligned with the planned trajectory LH, as in FIG. 9, according to the surgical plan, or if the rotational axis R has been moved away from the desired trajectory for other reasons, the rotational axis R is aligned in step 402. Specifically, in step 402, the robotic surgical system 10 controls movement of the surgical tool 30, to place the rotational axis R along the desired trajectory. This may comprise the robotic surgical system 10 causing autonomous movement of the surgical tool 30, to place the rotational axis R along the desired trajectory. Alternatively, the robotic surgical system 10 may enable the operator to move the surgical tool 30 by applying force/torque in a manual mode until the rotational axis R is placed along the planned trajectory LH. The robotic surgical system 10 can generate feedback (visual, audible, and/or haptic) to the operator to indicate proper alignment. In some examples, attractive haptics may be utilized to pull the tool 30 toward the planned trajectory LH as the position of the tool is near the planned trajectory LH by a threshold distance defined by the attractive haptics.

During step 406, the robotic surgical system 10 causes autonomous movement of the surgical tool 30 to simultaneously control the autonomous advancement of the tool linearly along the planned trajectory LH, while also controlling the autonomous rotation of the surgical tool about the rotational axis R. The autonomous control of the advancement and the rotation is related to the thread pitch defined by the equation Eq. 1, described above. The autonomous control dictated by the thread pitch ensures proper installation of the pedicle screw to avoid causing damage to surrounding bone tissue.

Step 214 may be commanded by the operator in multiple alternatives. In a first example, the robotic surgical system 10 may be configured to execute in complete autonomy. That is, once the operator has commanded the robotic surgical system 10 to perform autonomous control of the surgical tool 30, the robotic surgical system 10 performs the autonomous control with no further operator input until the operation completes. In an alternative instance, the operator may initiate the autonomous execution of the operation and then provide the continuing input such as by pressing and holding a button, by pressing and holding a foot switch, or other continuous input control so that if the input ceases, e.g. the button or footswitch is released, then the robotic surgical system 10 pauses execution of the operation. In cooperation with the autonomous control, the operator may modulate the velocity at which the operation executes. In addition to a button or footswitch, an additional control may be provided so that the operator can command an increase or decrease in the robot velocity in a step-wise function with multiple discrete velocities. The additional velocity control may include a set of buttons, selectors, dials, or other suitable control.

Referring to FIG. 15A, if, during step 206, the robotic surgical system 10 determines whether the operation has ended. The operation may be determined to have ended using a variety of methods. For example, if the operator determines that all the pedicle screws PS are implanted to a desired depth, the operator may command the end of the operation. As another example, if the operator subjectively determines that the operation has ended, the operator may command the end of the operation. Yet another example, if the one or more controllers 33 determine that all the pedicle screws PS are inserted to a desired depth, the one or more controllers 33 may trigger the end of the operation. However, in some instances, after a pedicle screw PS is implanted to a desired depth, the operation has not ended. In such instances, the method may repeat steps of the method of FIG. 15A for another pedicle screw PS and continue until all pedicle screws PS are implanted.

If the robotic surgical system 10 determines that the operation has ended during step 206, the method proceeds to a step 216 of determining whether the surgical tool 30 is inserted at the target site. During step 216, the one or more controllers 33 may determine the position of the surgical tool 30 and whether the surgical tool 30 is inserted at the target site. If the robotic surgical system 10 determine that the surgical tool 30 is not inserted, the method proceeds to step 218, the end of the operation. If the robotic surgical system 10 determines that the surgical tool 30 is inserted, the method proceeds to a step 220 of withdrawing the tool before proceeding to the end of the step 218.

During step 220 the surgical tool 30 is withdrawn from the implant. As with advancing the pedicle screw PS into the bone, the operator may input a force at the surgical tool 30 in the direction away from the vertebra V to command the withdrawal of the surgical tool 30. Alternatively, the robotic surgical system 10 may autonomously withdraw the surgical tool 30 without further input from the operator once the implant is placed.

A partial facetectomy may be carried out with the surgical tool 30 to provide a smooth bony surface for final receipt of a head of the pedicle screw PS. The resection volume can be defined based on the operator's plan, i.e., by determining a location of the head in the 3-D model. A bur or pre-shaped reamer 70 that corresponds to the head shape can be used to remove the material. In some cases, the drill 42 may incorporate the reamer therein to avoid separate tools so that the drill 42 has a smaller profile drilling shaft to create the pilot hole and more proximally located is the reamer 70 to create the seat 72 for the head of the pedicle screw PS-thus at least part of the pilot hole 102 and the seat 72 can be formed simultaneously. In the instance shown, the drill 42 has a drilling shaft with proximal and distal ends and a drill tip at the distal end. The reamer 70 is spaced proximally from the drill tip so that the reamer 70 is located near a facet once the drill 42 has been inserted to the desired depth in the target vertebral body. Any suitable drill and/or reamer cutting features may be employed to form the hole, e.g., to form the pilot hole and the seat in the spine of the patient to receive the implant.

It should be appreciated that the systems and methods described herein can be employed to place pedicle screws PS, other screws, fasteners, or other implants into a patient. So, even though pedicle screws PS are referenced throughout as one example, the same systems and methods described herein could be utilized for treating any anatomy of the patient and/or for placing any implants into the patient, e.g., in the hip, knee, femur, tibia, face, shoulder, spine, etc. For instance, the robotic arm 20 may also be used to place a cage for a spine implant, to place rods, to drive pins, to implant a threaded cup, or to place other components, and could be used for hip replacement, discectomy, or other procedures. Different end effectors could also be attached to the robotic arm 20 for other procedures. In some cases, the end effector may also have an articulating arm to facilitate implant insertion, i.e., placing the implant in a desired pose. The articulating arm of the end effector could simply be a miniature version of the robotic arm 20 controlled in the same manner to place the implant or could be another mechanism controlled to position the implant.

The navigation system 12 may comprise an optical navigation system with optical-based trackers, but could additionally or alternatively employ other modalities, such as ultrasound navigation systems that track objects via ultrasound, radio frequency navigation systems that track objects via RF energy, and/or electromagnetic navigation systems that track objects via electromagnetic signals. Other types of navigation systems are also contemplated. It should also be appreciated that the models described herein may comprise triangulated meshes, volumetric models using voxels, or other types of 3-D and/or 2-D models in some cases.

Several instances have been discussed in the foregoing description. However, the instances discussed herein are not intended to be exhaustive or limit the disclosure to any particular form. The terminology which has been used is intended to be in the nature of words of description rather than of limitation. Many modifications and variations are possible in light of the above teachings and the disclosure may be practiced otherwise than as specifically described.

What is claimed is:

1. A robotic surgical system comprising:
a robotic manipulator;
a surgical tool coupled to the robotic manipulator and configured to interface with a screw and to rotate the screw about a rotational axis;
a hand-held pendant remotely spaced apart from the robotic manipulator and the surgical tool and comprising an actuator and a rotational interface coupled to the actuator and the rotational interface being configured to be manually manipulatable by a hand of an operator;
a navigation system configured to track a position of a target site;
a memory comprising computer-readable instructions; and
one or more controllers coupled to the memory, the robotic manipulator, the hand-held pendant and the navigation system, and the one or more controllers configured to implement the computer-readable instructions to:
control movement of the robotic manipulator to maintain the rotational axis of the surgical tool along a planned trajectory with respect to the target site based on the tracked position of the target site;
obtain a known thread geometry of the screw;
autonomously control the surgical tool to rotate the screw at a rotational rate about the rotational axis and to linearly advance the screw at an advancement rate along the planned trajectory, wherein the rotational rate and the advancement rate are predetermined and proportional to the known thread geometry of the screw;
obtain a measurement indicative of a present interaction between the screw and the target site; and
based on the obtained measurement, control the actuator of the hand-held pendant to enable the rotational interface to emulate the present interaction between the screw and the target site.

2. The robotic surgical system of claim 1, wherein the one or more controllers further emulate the present interaction between the screw and the target site by being configured to provide a resistive force to the actuator to adjust a force required to rotate the rotational interface by the hand of the operator, wherein the force required to rotate the rotational interface reflects a present force required to rotate the screw relative to the target site.

3. The robotic surgical system of claim 2, wherein the one or more controllers are further configured to initiate an autonomous check mode, wherein the rotational interface is manually manipulatable:
according to the adjusted force to provide the operator with haptic feedback reflecting the present force required to rotate the screw relative to the target site; and
without an ability to control the surgical tool to rotate the screw; and
wherein, in response to a condition or a command, the one or more controllers are further configured to:
initiate the autonomous check mode concurrent to autonomously controlling the surgical tool;
initiate the autonomous check mode after stopping or pausing autonomously controlling the surgical tool to stop rotation of the screw; and
resume autonomously controlling the surgical tool to rotate the screw after autonomous control of the surgical tool is stopped or paused to stop rotation of the screw.

4. The robotic surgical system of claim 2, wherein:
the one or more controllers are further configured to initiate a manual control mode, wherein the rotational interface is manually manipulatable with an ability to control one of the rotational rate of the screw or the advancement rate of the screw based on the operator manually manipulating the rotational interface;
the one or more controllers are configured to control the surgical tool to rotate the screw at the rotational rate about the rotational axis and to linearly advance the screw at the advancement rate along the planned trajectory in response to the rotational interface being manually manipulated to control one of the rotational rate of the screw or the advancement rate of the screw; and
the rotational interface is manually manipulatable according to the adjusted force to provide the operator with haptic feedback reflecting the present force required to rotate the screw relative to the target site; and
wherein, in response to a condition or a command, the one or more controllers are further configured to:
initiate the manual control mode after stopping or pausing autonomously controlling the surgical tool to stop rotation of the screw; and
switch from the manual control mode to resuming autonomously controlling the surgical tool to rotate the screw.

5. The robotic surgical system of any one of claim 4, wherein the one or more controllers are configured to:
determine that a condition exists during control of the screw; and
in response to determining that the condition exists, provide the operator with haptic feedback regarding the condition by controlling the actuator of the hand-held pendant to prevent an ability to rotate the rotational interface.

6. The robotic surgical system of claim 1, wherein the navigation system is further configured to:
determine a position of the screw relative to an anatomical model of the target site that is registered to the target site, the navigation system including predetermined data indicative of expected interactions between the screw and the anatomical model at a plurality of positions of the screw relative to the anatomical model; and obtain the measurement indicative of the present interaction between the screw and the target site based on the determined position of the screw relative to the anatomical model and the predetermined data.

7. The robotic surgical system of claim 1, wherein the rotational rate and the advancement rate are proportional to the known thread geometry according to a relationship $$\frac{\delta\theta}{\delta t} = \frac{\delta D}{\delta t} * \frac{Pitch}{2\pi},$$

wherein $$\frac{\delta\theta}{\delta t}$$

is the rotational rate, $$\frac{\delta D}{\delta t}$$

is the advancement rate, and Pitch is a number of threads per unit length of the screw.

8. The robotic surgical system of claim 1, wherein the one or more controllers are further configured to receive an input from the operator to selectively adjust one or more of:

a resistive force provided to the actuator; and a sensitivity of the rotational interface's ability to control the surgical tool to rotate the screw.

9. The robotic surgical system of claim 1, wherein the robotic surgical system further comprises a display, and wherein the one or more controllers are further configured to initiate a simulated autonomous check mode, wherein the one or more controllers are configured to:

simulate autonomously controlling the surgical tool by rotating the screw at the rotational rate about the rotational axis and linearly advancing the screw at the advancement rate along the planned trajectory;

display the simulated autonomous control of the surgical tool on the display;

obtain a simulated present interaction between the screw and the target site; and based on the simulated present interaction, control the actuator of the hand-held pendant to enable the rotational interface to emulate the simulated present interaction between the screw and the target site; and wherein the one or more controllers are further configured to initiate the simulated autonomous check mode prior to autonomously controlling the surgical tool.

10. The robotic surgical system of claim 1, wherein the robotic surgical system further comprises a display, and wherein the one or more controllers are further configured to initiate a simulated manual control mode, wherein the one or more controllers are configured to:

receive control input in response to the rotational interface being manually manipulated to control one of the rotational rate of the screw or the advancement rate of the screw;

simulate manually controlling the surgical tool by rotating the screw at the rotational rate about the rotational axis and linearly advancing the screw at the advancement rate along the planned trajectory in response to the control input;

display the simulated manual control of the surgical tool on the display;

obtain a simulated present interaction between the screw and the target site; and based on the simulated present interaction, control the actuator of the hand-held pendant to enable the rotational interface to emulate the simulated present interaction between the screw and the target site; and wherein, in response to a condition or a command, the one or more controllers are further configured to initiate the simulated manual control mode after stopping or pausing autonomously controlling the surgical tool to stop rotation of the screw.

11. A method of controlling a robotic surgical system, the robotic surgical system including a robotic manipulator, a surgical tool coupled to the robotic manipulator and configured to interface with a screw and to rotate the screw about a rotational axis, a hand-held pendant remotely spaced apart from the robotic manipulator and the surgical tool and including an actuator and a rotational interface coupled to the actuator and configured to be manually manipulatable by a hand of an operator, a navigation system configured to track a position of a target site, a memory including computer-readable instructions, and one or more controllers coupled to the memory, the robotic manipulator, the hand-held pendant, and the navigation system, the method comprising:

controlling, with the one or more controllers, movement of the robotic manipulator to maintain the rotational axis of the surgical tool along a planned trajectory with respect to the target site based on the tracked position of the target site;

implementing, with the one or more controllers, the computer-readable instructions to obtain a known thread geometry of the screw;

autonomously controlling, with the one or more controllers, the surgical tool to rotate the screw at a rotational rate about the rotational axis and to linearly advance the screw at an advancement rate along the planned trajectory, wherein the rotational rate and the advancement rate are predetermined and proportional to the known thread geometry of the screw;

obtaining, with the one or more controllers, a measurement indicative of a present interaction between the screw and the target site; and controlling, with the one or more controllers and based on the obtained measurement, the actuator of the hand-held pendant to enable the rotational interface to emulate the present interaction between the screw and the target site.

12. The method of claim 11, wherein controlling the actuator of the hand-held pendant to enable the rotational interface to emulate the present interaction between the screw and the target site based on the obtained measurement includes providing, with the one or more controllers, a resistive force to the actuator to adjust a force required to rotate the rotational interface by the hand of the operator, wherein the force required to rotate the rotational interface reflects a present force required to rotate the screw relative to the target site.

13. The method of claim 12, further comprising:

initiating, with the one or more controllers, an autonomous check mode, wherein the rotational interface is manually manipulatable:

according to the adjusted force to provide the operator with haptic feedback reflecting the present force required to rotate the screw relative to the target site; and without an ability to control the surgical tool to rotate the screw; and initiating, with the one or more controllers, the autonomous check mode concurrent to autonomously controlling the surgical tool in response to a condition or a command;

initiating, with the one or more controllers, the autonomous check mode after stopping or pausing autonomously controlling the surgical tool to stop rotation of the screw in response to a condition or a command; and resuming, with the one or more controllers, autonomously controlling the surgical tool to rotate the screw after autonomous control of the surgical tool is stopped or paused to stop rotation of the screw and in response to a condition or a command.

14. The method of claim 12, further comprising:

initiating, with the one or more controllers, a manual control mode, wherein the rotational interface is manually manipulatable with an ability to control one of the rotational rate of the screw or the advancement rate of the screw based on the operator manually manipulating the rotational interface; and controlling, with the one or more controllers, the surgical tool to rotate the screw at the rotational rate about the rotational axis and to linearly advance the screw at the advancement rate along the planned trajectory in response to the rotational interface being manually manipulated to control one of the rotational rate of the screw or the advancement rate of the screw; and wherein the rotational interface is manually manipulatable according to the adjusted force to provide the operator with haptic feedback reflecting the present force required to rotate the screw relative to the target site.

15. The method of claim 14, further comprising:

initiating, with the one or more controllers, the manual control mode after stopping or pausing autonomously controlling the surgical tool to stop rotation of the screw in response to a condition or a command; and switching, with the one or more controllers, from the manual control mode to resuming autonomously controlling the surgical tool to rotate the screw in response to a condition or a command.

16. The method of claim 14, further comprising:

determining, with the one or more controllers, that a condition exists during control of the screw; and providing, with the one or more controllers, haptic feedback regarding the condition by controlling the actuator of the hand-held pendant to prevent an ability to rotate the rotational interface in response to determining that the condition exists.

17. The method of claim 11, further comprising receiving, with the one or more controllers, an input from the operator to selectively adjust one or more of:

a resistive force provided to the actuator; and a sensitivity of the rotational interface's ability to control the surgical tool to rotate the screw.

18. The method of claim 11, wherein the robotic surgical system further includes a display, the method further comprising:

initiating, with the one or more controllers, a simulated autonomous check mode comprising the one or more controllers:

simulating autonomously controlling the surgical tool by rotating the screw at the rotational rate about the rotational axis and linearly advancing the screw at the advancement rate along the planned trajectory;

displaying the simulated autonomous control of the surgical tool on the display;

obtaining a simulated present interaction between the screw and the target site; and based on the simulated present interaction, controlling the actuator of the hand-held pendant to enable the rotational interface to emulate the simulated present interaction between the screw and the target site; and initiating, with the one or more controllers, the simulated autonomous check mode prior to autonomously controlling the surgical tool.

19. The method of claim 11, wherein the robotic surgical system further includes a display, the method further comprising initiating, with the one or more controllers, a simulated manual control mode comprising the one or more controllers:

receiving control input in response to the rotational interface being manually manipulated to control one of the rotational rate of the screw or the advancement rate of the screw;

simulating manually controlling the surgical tool by rotating the screw at the rotational rate about the rotational axis and linearly advancing the screw at the advancement rate along the planned trajectory in response to the control input;

displaying the simulated manual control of the surgical tool on the display;

obtaining a simulated present interaction between the screw and the target site;

based on the simulated present interaction, controlling the actuator of the hand-held pendant to enable the rotational interface to emulate the simulated present interaction between the screw and the target site; and initiating, with the one or more controllers, the simulated manual control mode after stopping or pausing autonomously controlling the surgical tool to stop rotation of the screw in response to a condition or a command.

* * * * *